United States Patent

Marchosky et al.

[11] Patent Number: 5,197,466
[45] Date of Patent: * Mar. 30, 1993

[54] METHOD AND APPARATUS FOR VOLUMETRIC INTERSTITIAL CONDUCTIVE HYPERTHERMIA

[75] Inventors: J. Alexander Marchosky, Creve Coeur; Christopher J. Moran, Town and Country, both of Mo.; Neal E. Fearnot, West Lafayette, Ind.

[73] Assignee: MED Institute Inc., West Lafayette, Ind.

[*] Notice: The portion of the term of this patent subsequent to Oct. 9, 2007 has been disclaimed.

[21] Appl. No.: 818,738

[22] Filed: Jan. 7, 1992

Related U.S. Application Data

[60] Division of Ser. No. 593,103, Oct. 5, 1990, abandoned, which is a division of Ser. No. 193,167, May 2, 1988, Pat. No. 4,961,422, which is a continuation of Ser. No. 112,628, Oct. 22, 1987, abandoned, which is a continuation-in-part of Ser. No. 697,697, Feb. 4, 1985, Pat. No. 4,719,919, which is a continuation of Ser. No. 459,708, Jan. 21, 1983, abandoned.

[51] Int. Cl.⁵ .............................................. A61F 7/12
[52] U.S. Cl. ..................................... 128/399; 128/401; 128/784; 606/13; 606/27
[58] Field of Search ............... 128/399, 400, 401, 402, 128/784, 804; 606/27, 31, 32, 41, 42

[56] References Cited

U.S. PATENT DOCUMENTS

| | | | |
|---|---|---|---|
| 2,777,445 | 1/1957 | Hart | 128/303.12 |
| 3,088,027 | 4/1963 | Graham | 378/163 |
| 3,170,465 | 2/1965 | Henney et al. | 128/303.1 |
| 3,231,834 | 1/1966 | Watanabe | |
| 3,369,549 | 2/1968 | Armao | 128/303.1 |
| 3,404,678 | 10/1968 | Von Ardenne | |
| 3,453,546 | 7/1969 | Fryer | |
| 3,508,552 | 4/1970 | Hainault | 128/303 B |
| 3,698,394 | 10/1972 | Piper et al. | 128/303.1 |
| 3,714,428 | 1/1973 | Gasaway | 378/163 |
| 3,717,140 | 2/1973 | Greenwood | 128/2.05 T |
| 3,817,249 | 6/1974 | Nicholson | 606/129 |
| 3,901,224 | 8/1975 | Buçalo | 128/82.1 |
| 3,938,526 | 2/1976 | Anderson et al. | 128/303.1 |
| 3,942,535 | 3/1976 | Schulman | 128/419 PS |
| 3,949,388 | 4/1976 | Fuller | 340/189 M |
| 3,972,320 | 8/1976 | Kalman | 128/2.1 A |
| 3,991,770 | 11/1976 | LeVeen | 128/413 |
| 4,016,886 | 4/1977 | Doss et al. | 128/399 |
| 4,046,139 | 9/1977 | Horn | 128/2 H |
| 4,119,102 | 10/1978 | LeVeen | 128/413 |
| 4,121,592 | 10/1978 | Whalley | 128/413 |

(List continued on next page.)

FOREIGN PATENT DOCUMENTS

| | | | |
|---|---|---|---|
| 0048402 | 3/1982 | European Pat. Off. | 128/303.1 |
| WO84/02839 | 8/1984 | PCT Int'l Appl. | |
| 88/03676 | 10/1988 | PCT Int'l Appl. | |

OTHER PUBLICATIONS

Hornback, Ned B., "Hyperthermia and Cancer," (CRC Press, Boca Raton, Fla., 1984), vol. II, Chapter I.

(List continued on next page.)

Primary Examiner—Jessica J. Harrison
Attorney, Agent, or Firm—Richard J. Godlewski

[57] ABSTRACT

A system and method for producing volumetric conductive hyperthermia for the treatment of a cancerous tumor in a patient. The location and volume of the tumor are determined with the aid of a CT scanning system, and an array of probes each containing a heat-emitting element is formed by interstitial implantation in the tumor in a predetermined pattern for volumetric heating using a template for guiding the probes into parallel alignment in the tumor. The template is affixed with respect to the patient's body and with respect to the imaging plane of the CT scanning system. After implantation, the probes are connected to a manifold which is in turn connected to an external control system capable of independently controlling the probes while monitoring various analog and digital values representative of system performance.

29 Claims, 26 Drawing Sheets

U.S. PATENT DOCUMENTS

| | | | |
|---|---|---|---|
| 4,127,110 | 11/1978 | Bullara | 128/2 P |
| 4,142,529 | 3/1979 | Latenser et al. | 128/401 |
| 4,146,029 | 3/1979 | Ellinwood | 128/260 |
| 4,166,451 | 9/1979 | Salera | 128/736 |
| 4,181,132 | 1/1980 | Parks | 128/399 |
| 4,182,313 | 1/1980 | Aslan | 128/736 |
| 4,186,729 | 2/1980 | Harrison | 128/1.3 |
| 4,204,549 | 5/1980 | Paglione | 128/784 |
| 4,210,152 | 7/1980 | Berry | 128/422 |
| 4,223,678 | 9/1980 | Langer et al. | 128/419 D |
| 4,227,535 | 10/1980 | Connor | 128/401 |
| 4,232,679 | 11/1980 | Schulman | 128/419 PG |
| 4,237,900 | 12/1980 | Schulman et al. | 128/630 |
| 4,275,738 | 6/1981 | McDonald et al. | 128/419 PG |
| 4,298,006 | 11/1981 | Parks | 128/399 |
| 4,312,364 | 1/1982 | Convert et al. | 128/804 |
| 4,331,161 | 5/1982 | Patel | 128/736 |
| 4,333,469 | 6/1982 | Jeffcoat et al. | 128/419 F |
| 4,341,220 | 7/1982 | Perry | 128/303 B |
| 4,346,725 | 8/1982 | Gammell | 128/784 |
| 4,352,960 | 10/1982 | Dormer et al. | 179/107 BC |
| 4,360,028 | 11/1982 | Barbier et al. | 128/659 |
| 4,427,005 | 1/1984 | Tener | 606/130 |
| 4,448,198 | 5/1984 | Turner | 128/804 |
| 4,465,069 | 8/1984 | Barbier et al. | 128/659 |
| 4,475,550 | 10/1984 | Bremer et al. | 128/303 B |
| 4,483,341 | 11/1984 | Witteles | 128/402 |
| 4,580,561 | 4/1986 | Williamson | 128/303 B |
| 4,586,490 | 5/1986 | Katz | 604/173 |
| 4,612,940 | 9/1986 | Kasevich et al. | 128/804 |
| 4,618,978 | 10/1986 | Cosman | 378/162 |
| 4,638,436 | 1/1987 | Badger et al. | 128/401 |
| 4,669,475 | 6/1987 | Turner | 128/399 |
| 4,679,561 | 7/1987 | Doss | 128/422 |
| 4,691,333 | 9/1987 | Gabriele et al. | 128/303 B |
| 4,695,709 | 9/1987 | Sachs et al. | 128/303.18 |
| 4,712,559 | 12/1987 | Turner | 128/399 |
| 4,719,919 | 1/1988 | Marchosky et al. | 128/401 |
| 4,739,771 | 4/1988 | Manwaring | 128/691 |
| 4,744,370 | 5/1988 | Harris | 128/786 |
| 4,776,086 | 10/1988 | Kasevich et al. | 128/784 |
| 4,791,934 | 12/1988 | Brunnett | 128/303 B |
| 4,800,899 | 1/1989 | Elliott | 128/736 |
| 4,947,842 | 8/1990 | Marchoski et al. | 128/401 |
| 4,961,422 | 10/1990 | Marchosky et al. | 128/399 |
| 4,989,601 | 2/1991 | Marchosky et al. | 128/399 |

OTHER PUBLICATIONS

Storm, F. Kristian, "Hyperthermia in Cancer Therapy," (G. K. Hall Medical Publishers, Boston, 1983), Table of Contents.

Nussbaum, Gilbert H., "Physical Aspects of Hyperthermia," (American Institute of Physics, New York, 1982), Table of Contents.

Parsonnet et al., "An Experimental Method for Thermal Control of Heart Rate: Work In Progress," *PACE*, Sep.-Oct., 1980.

Murawski et al., "An Externally Programmable, Implantable, Integrated Cerebellar Stimulator," *IEEE in Medicine & Biology Society*, 1982.

Taylor, "Brain Cancer Therapy Using an Implanted Microwave Radiator," *Microwave Journal*, 1981.

Sutton, Carl H., "Tumor Hyperthermia in the Treatment of Malignant Gliomas of the Brain," *Transactions of the American Neurological Association*, 96:195-199, 1971.

Anghileri, Leopold et al. [Eds.], *Hyperthermia in Cancer Treatment*, CRC Press, Inc., Boca Raton, Florida, 1986, vol. II, pp. 126, 136-138; vol. III, pp. 26, 44.

Pacela et al., "New Copolymer Will Administer Brain Cancer Drug," *Biomedical Technology*, vol. 14, No. 24, Nov. 15, 1987, p. 244.

Mulcahy, "Hyperthermia and Chemotherapy," *Syllabus: A Categorical Course in Radiator Therapy: Hyperthermia*, Radiological Society of North America, Nov. 29-Dec. 4, 1987, pp. 27-35.

Tamargo et al., "Growth Inhibition of the 9L Gliosarcoma by the Local Sustained Release of BCNU: A Comparison of Systemic versus Regional Chemotherapy," *Scientific Program: The Meeting of the American Association of Neurological Surgeons*, Apr. 24-28, 1988, Toronto, Ontario p. 212.

Brem et al., "A Biodegradable Polymer for Intracranial Drug Delivery: A Radiological Study in Primates," *Scientific Program: The Annual Meeting of the American Association of Neurological Surgeons*, Apr. 24-28, 1988, Toronto, Ontario, pp. 381-382.

Brem et al., "Biocompatibility of a BCNU-Loaded Biodegradable Polymer: A Toxicity Study in Primates," *Scientific Program: The Annual meeting of the American Association of Neurological Surgeons*, Apr. 24-28, 1988, Toronto, Ontario, pp. 381-382.

Tamargo et al., "Brain Biocompatibility of a Biodegradable Polymer Capable of Sustained Release of Macromolecules," *Scientific Program: The Annual Meeting of*

(List continued on next page.)

OTHER PUBLICATIONS the American Association of Neurological Surgeons, Apr. 24-28, 1988, Toronto, Ontario, pp. 399-400.

Yang et al., "Sustained Systemic Delivery of BCNU from an Intraperitoneal Polymer Implant," *Scientific Program: The Annual Meeting of the American Association of Neurological Surgeons*, Apr. 24-28, Toronto, Ontario, p. 414.

Leong et al., "Bioerodible polyanhydrides as drug-carrier matrices. II. Biocompatibility and chemical reactivity, *Journal of Biomedical Materials Research*, vol. 20, 1986, pp. 51-64.

Leong et al., "Bioerodible Polyanhydrides for Cancer Chemotherapy," *Proceed. Intern. Symp. Control. Bioact. Mater.*, 12, 1985, pp. 106-107.

Rosen et al., "Bioerodible Polyanhydrides for Controlled Drug Delivery," *Biomaterials*, 1983, vol. 4, Apr., pp. 131-133.

Leong et al., "Bioerodible polyanhydrides as drug-carrier matrices. I: Characterization, degradation, and release characteristics," *Journal of Biomedical Materials Research*, vol. 19, 1985, pp. 941-955.

Beck et al., "An Overview of the FDA Approved Controlled-Release Polymeric Materials," Proceed Intern. Symp. Control. Rel. Bioact. Mater., 12, 1985, p. 214.

Langer, Robert S., "New Drug Delivery Systems: What the Clinician Can Expect," *Drug Therapy*, Apr., 1983, pp. 217-231.

Langer, et al., "Biocompatibility of Polymeric Delivery Systems for Macromolecules," *Journal of Biomedical Materials Research*, vol. 15, 1981, pp. 267-277.

Kenealy, Dr. J., "Safety and Efficacy of BCNU Delivered From a Biodegradable, Surgically Implanted Polymer For the Treatment of Grade III or IV Astrocytoma, Protocol NPC8701, Nova Pharmaceutical Corp., pp. 1-15.

"Treatment of Grade III and IV Anaplastic Glioma By Means of Controlled Release of Carmustine (BCNU) from Biodel TM, a Biodegradable Polymer," Investigator's Brochure, Nova Pharmaceutical Corporation, Jul. 20, 1988, pp. 1-32.

Brem et al., "Biocompatibility of a Biodegradable, Controlled-Release Polymer in the Rabbit Brain," The John Hopkins University School of Medicine, Baltimore, Md., 1988.

Grossman et al., "The Intracerebral Delivery of BCNU with Surgically Implanted Biodegradable Polymers: A Quantitative Autoradiographic Study, Proceedings of ASCO, vol. 7, Mar., 1988, p. 84.

Weiss, Rick, "Delivering the Goods: Designing a New Drug is One Thing; Getting it to the Disease is Another," *Science News*, vol. 133, pp. 360-362.

Langer et al., "Controlled Release: Three Mechanisms," *Chemtech*, Feb., 1986, pp. 108-110.

Tamargo et al., Brain Biocompatibility of a Biodegradable Controlled-Release Polymer In Rats," *Journal of Biomedical Materials Research*, vol. 00, 1988, pp. 00-00.

Leong et al., "Polyanhydrides for Controlled Release of Bioactive Agents," *Biomaterial*, vol. 7, Sep. 1986, pp. 364-371.

Anghileri, Leopold et al. [Eds.], *Hyperthermia in Cancer Treatment*, (CRC Press, Boca Raton, Fla., 1986) vol. II:190-193, vol. III:25-45.

Hornback, Ned. B., "Hyperthermia and Cancer," (CRC Press, Inc., Boca Raton, Fla., 1984), vol. I, pp. 65-75, 95-107; vol. II, pp. 107-111, 131-133.

Storm, F. Kristian [Ed.], *Hyperthermia in Cancer Therapy*, (G. K. Hall Medical Publishers, Boston, 1983), Chapters 1, 2, 11 and 12.

Nussbaum, Gilbert H. [Ed.], *Physical Aspects of Hyperthermia*, (American Institute of Physics, New York, 1982), pp. 90-104, 280-356, 368-392, and 495-538.

Hornbeck, Ned B., *Hyperthermia and Cancer*, (CRC Press, Boca Raton, Fla., 1984), vol. II, pp. 4-5, 18-21, and 96-97.

Nussbaum, Gilbert H. [Ed.], *Physical Aspects of Hyperthermia* (American Institute of Physics, New York, 1982), pp. 287-293, 300-305, 340-342, 368-370, and 495-534.

Storm, F. Kristian [Ed.], *Hyperthermia in Cancer Therapy* (G. K. Hall Medical Publishers, Boston, 1983), pp. 270-274.

Moran, Christopher J. et al., "A Simple Stabilization Device for Intracranial Aspiration Procedures Guided by Computed Tomography," *Radiology*, 144(1):183-184, Jul. 1982.

Moran, Christopher J. et al., "CT-Guided Needle Placement in the Central Nervous System: Results in 146 Consecutive Patients," *American Journal of Neuroradiology*, 5:419-426, Jul./Aug. 1984.

(List continued on next page.)

OTHER PUBLICATIONS

Marchosky, J. Alexander et al., "A Simple Stereotaxic CT-Controlled Brain Biopsy System for General Neurosurgical Use," *Contemporary Neurosurgery*, 5(18):1-8, 1983.

Abrath, Fred G. et al., "Dosimetry of CT-Guided Volumetric IR-192 Brain Implant," *International Journal of Radiation Oncology, Biology, Physics*, 12(3):359-363, Mar. 1986.

Taylor, Leonard S., "Implantable Radiators for Cancer Therapy by Microwave Hyperthermia," *Proceedings of the IEEE*, 68(1):142-149, Jan. 1980.

Taylor, Leonard S., "Electromagnetic Syringe," *IEEE Transactions on Biomedical Engineering*, BME-25(3):303-304, May 1978.

Seegenschmiedt, M. H. et al., "Optimized Clinical Pre-treatment Planning of Interstitial Hyperthermia," North American Hyperthermia Group, Philadelphia, Apr. 16-21, 1988 (Abstract and handout).

Strohbehn, John W. et al., "Blood Flow Effects on the Temperature Distributions from an Invasive Microwave Antenna Array Used in Cancer Therapy," *IEEE Transactions on Biomedical Engineering*, BME-29(9):649-661, Sep. 1982.

Strohbehn, John W. et al., "Interstitial Microwave Antenna Array Systems for Hyperthermia," *Frontiers of Radiation Therapy & Oncology*, 18:70-74, 1984.

Lyons, Bernard E. et al., "Localized Hyperthermia in the Treatment of Malignant Brain Tumors Using an Interstitial Microwave Antenna Array," *IEEE Transactions on Biomedical Engineering*, BME-31(1):53-62, Jan. 1984.

Percy, J. F., "Heat in the Treatment of Carcinoma of the Uterus," Symposium on Cancer of the Uterus, Clinical Congress of Surgeons of North America, Boston, Oct. 25-30, 1915.

"Scientists Planting 'Seeds' in Tumors of Cancer Patients," *The Indianapolis Star*, Dec. 2, 1984.

McKinley, Edward, "Radioactive 'Seeds' Helping Methodist Fight Brain Tumors," *The Indianapolis Star*, p. 18, Mar. 28, 1985.

Robinson, Donald, "Are We Winning Against Cancer?" *Parade*, p. 17, Jun. 14, 1987.

"Heat: A Treatment Option for Some Cancers?" *New York Times News Service*, 1988.

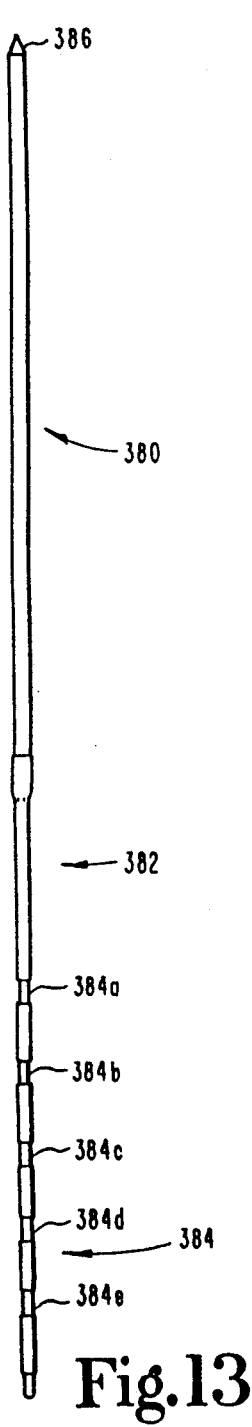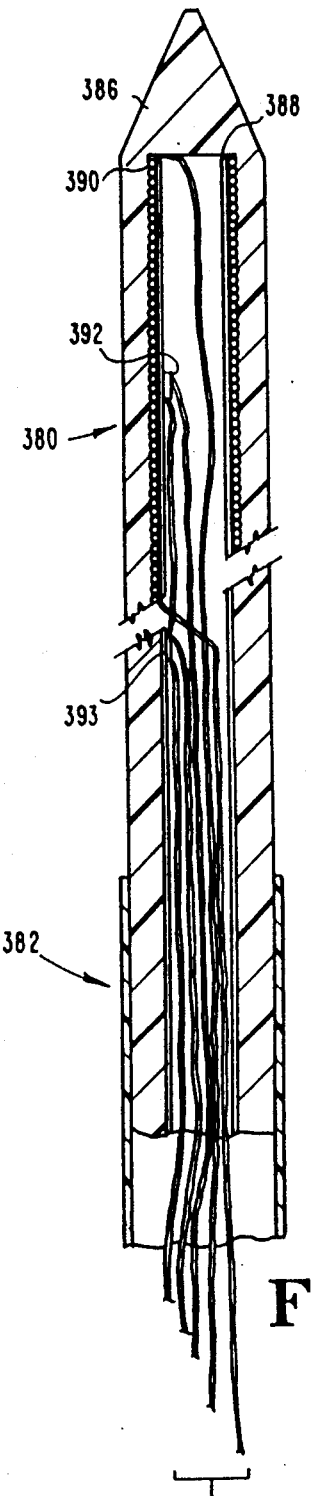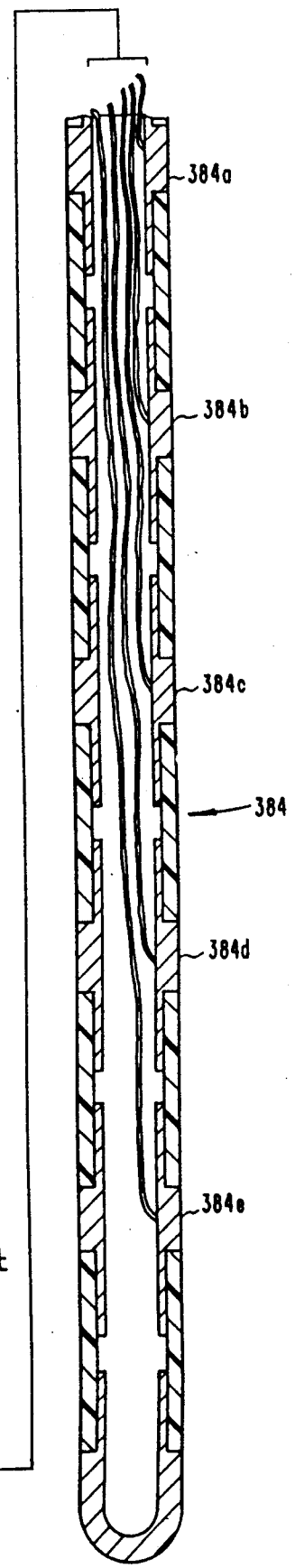
Fig.13
Fig.14

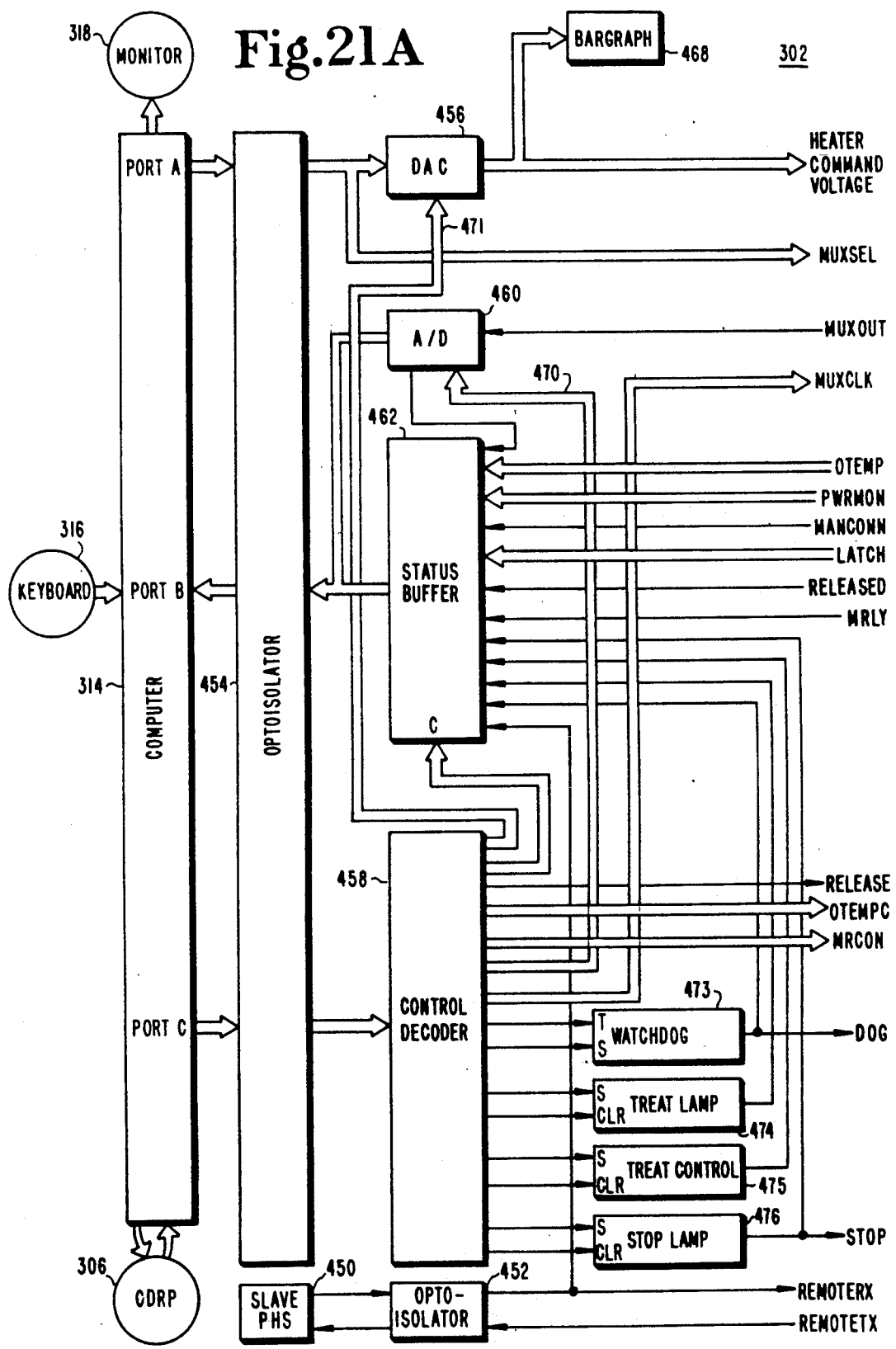

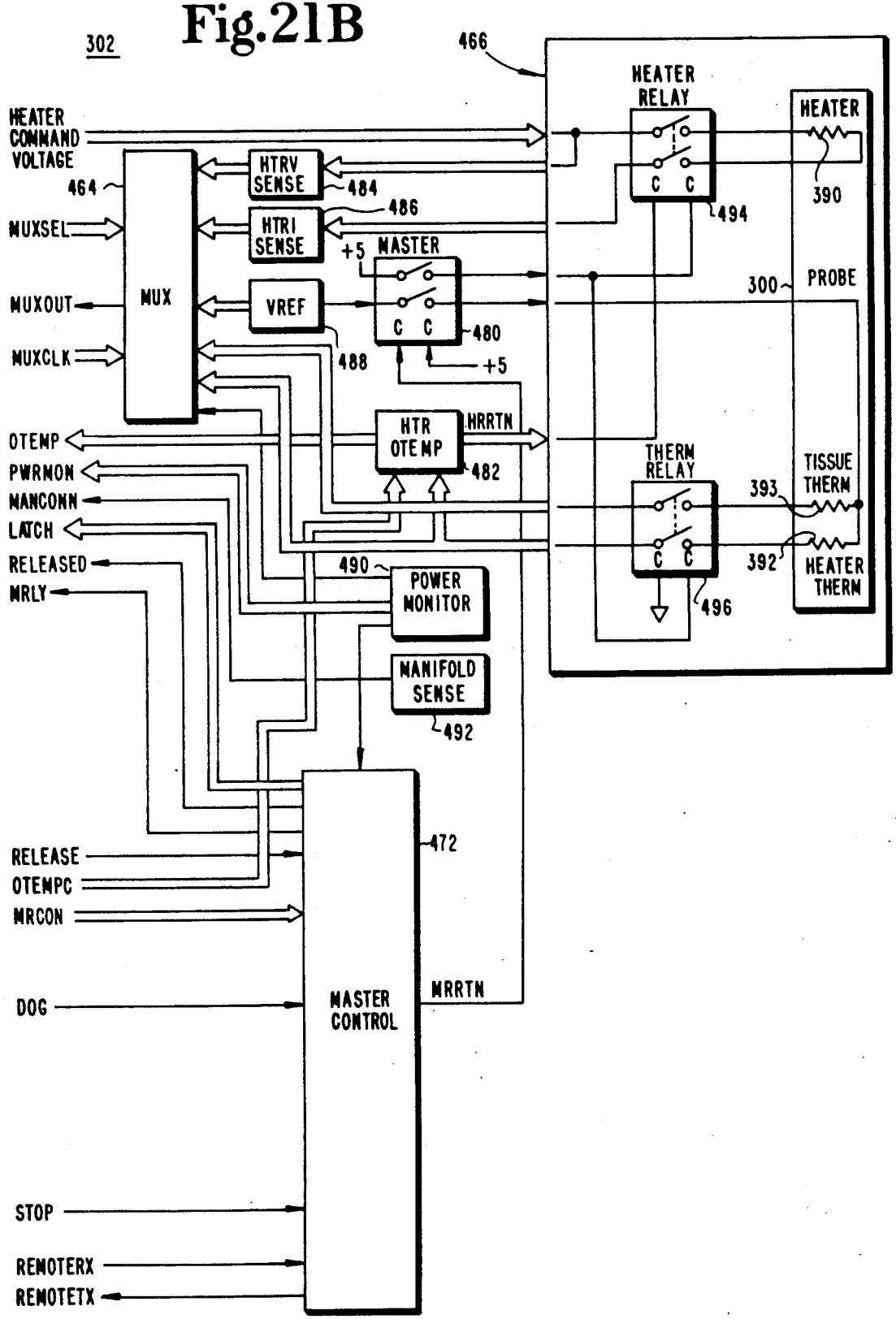

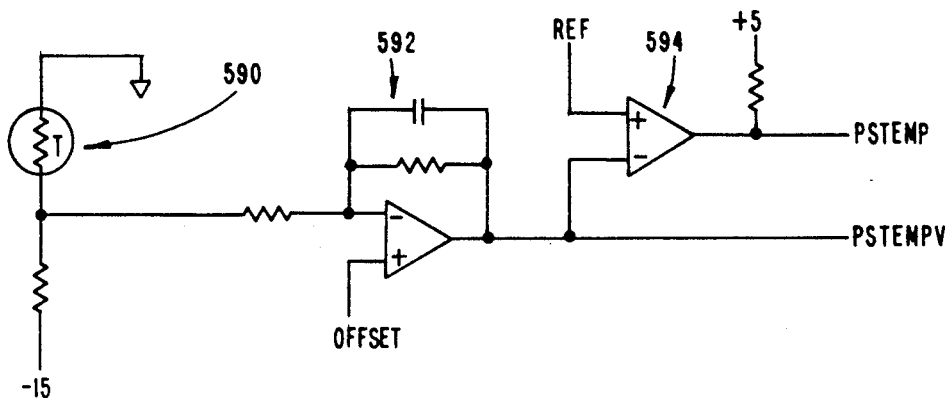
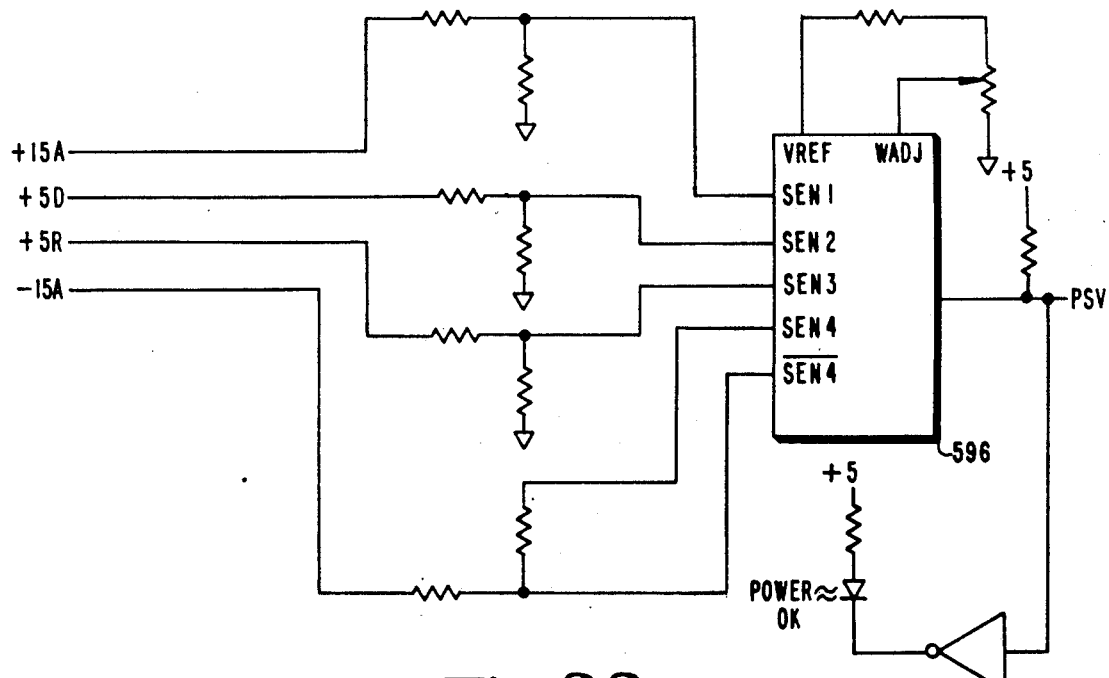
Fig.33

METHOD AND APPARATUS FOR VOLUMETRIC INTERSTITIAL CONDUCTIVE HYPERTHERMIA

CROSS REFERENCE TO RELATED APPLICATIONS

This application is a file wrapper divisional of copending application Ser. No. 07/593,103, filed Oct. 5, 1990, now abandoned, which is a divisional of copending application Ser.No. 07/193,167, now U.S. Pat.No. 4,961,422 filed May 2, 1988, which is a continuation of application Ser. No. 07/112,628, filed Oct. 22, 1987, now abandoned, which is a continuation-in-part of application Ser. No. 06/697,697, filed Feb. 4, 1985, now U.S. Pat. No. 4,719,919, which is a continuation of application Ser. No. 06/459,708, filed Jan. 21, 1983 and now abandoned.

BACKGROUND OF THE INVENTION

This invention relates to systems and methods for treatment of cancer, and particularly to the use of hyperthermia in cancer treatment.

Present modalities for treatment of malignant tumors include surgery, radiation therapy, chemotherapy, and immunotherapy which apply a physical or chemical force to alter the biological function of a tumor in order to affect its viability. Despite the medical advances that these modalities represent, most solid cancerous tumors carry with them a very poor prognosis for survival. Quality of life during and after treatment for survivors is often poor. The dismal prognosis for malignant solid tumors has led to continuing research for more effective treatment modalities with a lesser degree of disability and fewer side effects. In vitro and in vivo evidence indicates hyperthermia produces a significant anti-cancer activity through alteration of the physical environment of the tumor caused by increasing the temperature. Hyperthermia is more cytotoxic to tumor cells than normal cells because cancer cells are oxygen deprived, nutritionally deficient, and low in pH making them incapable of tolerating the stress imposed by elevated temperature. Tumor vasculature is immature, lacking the smooth muscle and vasoactivity which allows mature vessels to dilate, increasing blood flow to carry away heat, therefore intratumor temperatures exceed those in normal tissue. The mechanisms of selective cancer cell eradication by hyperthermia is not completely understood. However, four cellular effects of hyperthermia on cancerous tissue have been proposed: 1) changes in cell or nuclear membrane permeability or fluidity, 2) cytoplasmic lysomal disintegration, causing release of digestive enzymes, 3) protein thermal damage affecting cell respiration and the synthesis of DNA and RNA and 4) potential excitation of immunologic systems.

The major forms of energy for generating hyperthermia to date include microwaves, radio frequency induction, radio frequency localized current, and ultrasound. Most of the techniques used to dispense these are non-invasive, i.e,. the heat generating source is external to the body and does not invade the body. Consequently, the energy must pass through the skin surface and substantial power absorption by normal peripheral body tissue is unavoidable. Currently available external heating sources result in nonuniform temperature profiles throughout the tumor and increased temperatures in normal tissue. It is desirable to selectively heat tissues deep in a patient's body, i.e., to heat the tumor mass without heating cutaneous and normal tissue.

Others have attempted the use of interstitial techniques to obtain local hyperthermia, with limited success. Interstitial heating of brain tumors through an implantable microwave antenna has been investigated. However, microwave probes are ineffective in producing precisely controlled heating of tumors. Temperatures may deviate as much as 10 degrees Celcius from the desired target temperature. Besides, microwave activity adversely affects cellular structures and their integration, regardless of other thermal effects. The result is nonuniform temperatures throughout the tumor. Studies indicate that tumor mass reduction by hyperthermia is related to the thermal dose. Thermal dose is the minimum effective temperature applied throughout the tumor mass for a defined period of time. Hot spots and cold spots which occur with microwave hyperthermia may cause increased cell death at the hot spot, but ineffective treatment at cold spots resulting in future tumor growth. Such variations are a result of the microwave antenna's inability to evenly deposit energy throughout the tissue.

Since efferent blood flow is the major mechanism of heat loss for tumors being heated and blood flow varies throughout the tumor, more even heating of tumor tissue is needed to ensure more effective treatment.

To be effective, the application and deposition of thermal energy to the tumor must be precisely controlled to compensate for the variations in blood flow. In addition, the therapy itself will perturb the tumor's vascular system during treatment causing variations in local perfusion around the probe. Thus, heat loss from a tumor will be time dependent and affected by the hyperthermia treatment. This demonstrates the need to both monitor and control the temperature of the tumor throughout treatment.

SUMMARY OF THE INVENTION

The present invention teaches the details of a method for cancer treatment by means of interstitial conductive hyperthermia. The present invention also teaches the construction and operation of hyperthermia apparatus comprising a means for effectively achieving therapeutic heating of tumors deep in a patient's body by generation of heat within the tumor that has all of the desirable characteristics mentioned above. An embodiment of this invention provides for monitoring and control of tumor temperature to achieve a controlled pattern of energy deposition.

The method includes measurement and location of the tumor mass, implantation of an array of treatment probes in the tumor, and generation of volumetric hyperthermia through the implanted probes. Apparatus invented to facilitate this procedure includes an array of probes, a heat generating means for converting electrical energy into thermal energy, and a temperature sensing means. According to one embodiment of the invention, a template having an array of parallel apertures is affixed to a supporting structure on an imaging system for registration of probe position on an image generated by the imaging system.

It is accordingly an object of this invention to provide a safer and more effective means for treating cancerous tumors using a system for interstitial application of hyperthermia to the tumor with a multitude of implantable probes which conductively heat the tumor with precisely controlled temperature.

Another object is to locate a heater element at a location within the tumor to be treated so that heat generated thereby emanates outwardly into the surrounding tumor.

Another object is to minimize the surgical procedures necessary in the treatment of cancerous tumors.

Another object is to teach the construction and operation of a novel probe assembly capable of being implanted through tissues extending into a cancerous tumor with the least of a surgical procedure and damage to the patient.

Another object is to minimize the surgical procedures necessary to implant and maintain a heat generating device in a tumor.

A further object of this invention is to provide controlled therapeutic temperature fields in malignant structures using an array of interstitial, surgically implanted, heater/temperature sensitive probes to maintain tissue above a minimum cell death temperature throughout the tumor mass for a defined time.

These and other objects of the invention will become more readily apparent after considering the following detailed specification covering preferred embodiments thereof in conjunction with the accompanying drawings.

BRIEF DESCRIPTION OF THE DRAWINGS

FIGS. 13 and 14 are side view of a probe.

FIGS. 21a and 21b are block diagrams of an external control system according to the preferred embodiment of the present invention.

FIG. 33 is an electrical schematic of the power monitor shown in FIG. 21.

DESCRIPTION OF THE PREFERRED EMBODIMENT

Figure 1:
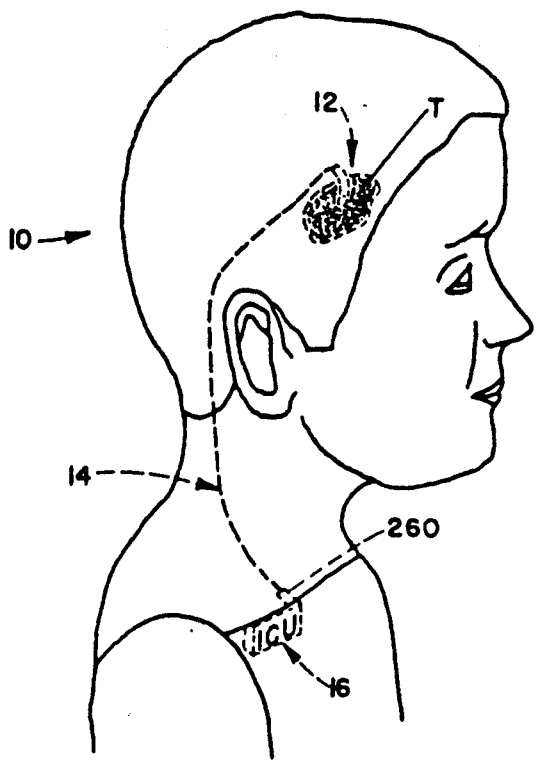
FIG. 1 is a side view of the head and upper body portion of a person equipped with an implanted hyperthermia system constructed according to the one embodiment of the present invention.

Referring to the drawings more particularly by reference numbers, number 10 in FIG. 1 refers to the head and upper body portion of a patient equipped with an implantable system constructed according to one embodiment of the present invention. The system includes a probe 12 which is shown imbedded in the head of the patient in position to extend from the surface of cranium of the head inwardly into a tumor T to be treated. A cable 14 is connected between the probe 12 and the internal control unit 16. The probe 12, the cable 14, and the internal control unit 16 are all surgically implanted in the body of the patient beneath the surface of the skin so that there is no protruding portion of the system which extends through or pierces the skin surface. This is useful in that it substantially reduces or eliminates the chances for infection and it is therefore expected that the internal system can remain in place for an extended period of time without any further surgical procedure being required. The details of the probe 12 and the internal control unit 16 will be described more in detail in connection with FIGS. 2A and 3.

Figure 2A:
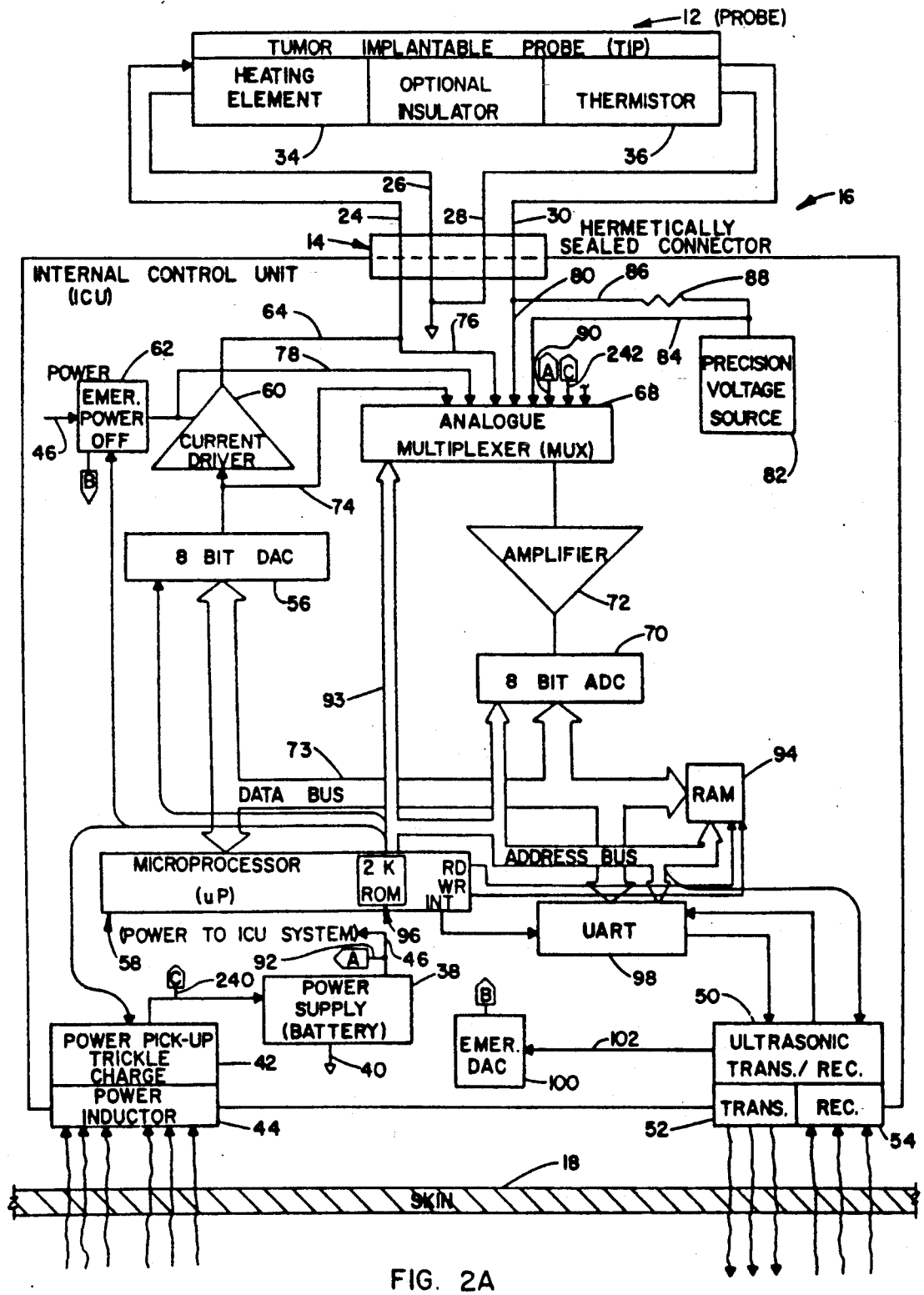
FIGS. 2A and 2B together are a schematic diagram of a control circuit for an implantable hyperthermia system including an internal or implanted system portion and the external portion for coupling to the internal portion.
Figure 2B:
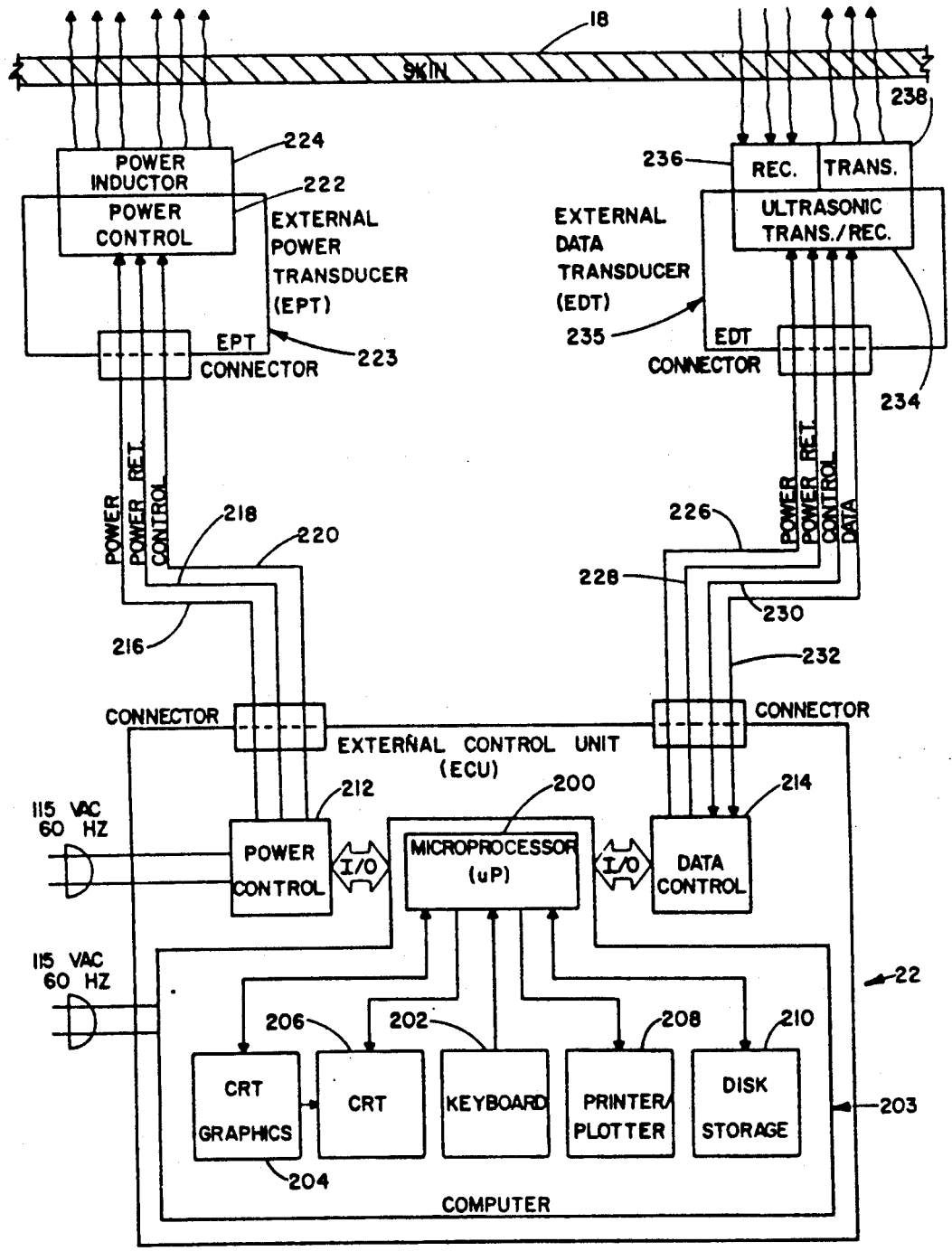

In FIGS. 2A and 2B, the skin 18 of the patient is shown positioned between the internal control unit 16 and an external control unit 22. The internal control unit 16 is shown coupled by leads 24, 26, 28 and 30 which are in the cable 14 to control elements located in the probe 12 including one or more heater elements 34 and one or more heat sensitive elements or thermistors 36. The probe 12, including the elements 34 and 36, and the internal control unit 16, are all surgically implanted under the skin of the patient so that nothing pierces or extends through the skin to cause infection or other problems. As stated, this is an important advantage of the present system. The internal control unit 16 includes means for controlling the application of electrical energy to the heater element or elements 34 according to according to some predetermined program or instructions established in the internal control unit and changed from time to time by the external unit 22 as will be described. The internal control unit 16 also has connections with the thermistor or thermistors 36 located on or adjacent to the probe at locations such that the thermistors are able to sense the temperature in the treatment area or tumor and provide outputs which can be used to evaluate and assess the effect of the treatment to enable modifying the treatment including the amount of heat generated by the heater element 34 as required to maintain some internal temperature condition for treatment purposes. For example, if the temperature of the tumor as sensed decreases then additional energy may need to be applied to the heater element 34 to maintain the temperature in the tumor at some desired level and for some desired time period or periods.

The heater elements 34 are preferably selected to be non-inductive, to have relatively low temperature coefficients and to be resistive type elements. The heaters should be able to increase the temperature of the surrounding tissue from normal body temperature of about 37° C. to a maximum temperature adjacent thereto of about 45° C. The heater 34 should also be able to withstand repeated exposure to radiation without any degradation in performance characteristics such as degradation in resistance, temperature coefficient, heat capacity and/or heat dissipation constant. For a typical probe construction the heater elements should also be as small as practical, and a typical size is in the order of 2 millimeters in diameter and 6 millimeters in length. Such devices are available commercially.

Referring to FIG. 2A the internal control unit 16 includes a power supply 38, grounded at 40 and shown connected to a power pick-up trickle charge circuit 42 which in turn is connected to a power inductor coil 44. The inductor coil 44 is preferably located on the unit 16 as near as possible to the surface of the skin 18 so that external means can be closely coupled thereto when it is necessary to recharge or trickle charge the power supply 38. The power supply 38 may include a rechargeable battery or some other similar rechargeable energy source. The power supply 38 has an output connection 46 which is the main power lead used to supply energy for the internal control unit including for operating the heater and thermistor elements 34 and 36.

The internal control unit (ICU) 16 is the portion of the system that controls the temperature generated by the heater element 34 as programmed internally by means of the external control unit (ECU) 22. The internal control unit 16 also includes ultrasonic transmit/receive means (transceiver) 50 which include transmitting portion 52 used to transmit information for receipt by the external control unit 22, and a receiver portion 54 which receives information transmitted by the external control unit 22 for various purposes including programming and reprogramming the internal control unit and controlling the transmissions of information between the units. The internal control unit includes a digital to analogue converter (DAC) circuit 56 which converts 8-bit binary parallel words from the output of an internal microprocessor ($\mu$P) 58 to current outputs which are used to energize the heater 34 to produce the amount of heat that is desired. The output of the 8-bit DAC 56 is applied through a current driver circuit 60 which may be an emitter follower circuit that receives power from the power supply 38 by way of emergency power-off circuit 62 connected thereto, as shown. The output of the current driver circuit 60 is a voltage that is applied to the non-grounded side of the heater element 34 by leads 64 and 24. The same output applied to the heater 34 is also applied as an input to an analogue multiplexer (MUX) circuit 68. The analogue multiplexer 68, under control of the microprocessor 58, is constructed and connected so as to be able to select and monitor various conditions throughout the internal control unit including the voltage on the heater element 34, the voltage on the thermistor or heat sensor 36, as well as other circuit conditions, and it converts the signals or responses being monitored to a digital format by means of an 8-bit analogue to digital converter (ADC) 70 by way of amplifier circuit 72. The signals thus converted are applied to the data bus 73 for entry into the microprocessor 58 and other circuit components. The analogue multiplexer 68 has other input connections from various locations in the circuit including an input connection from the output of the 8-bit digital to analogue converter 56 on lead 74, an input from the output of the current driver 60 on leads 64 and 76, an input from the output of the emergency power-off component 62 on lead 78, an input from the non-grounded side of the thermistor 36 on leads 30 and 80, and inputs from a precision voltage source 82 on leads 84, 86 and 80. The precision voltage source 82 is used in connection with the calibration of the thermistor 36. The lead 86 from the source 82 includes a biasing resistor 88. The analogue multiplexer 68 also has a power input connection on lead 90 which is connected to output lead 92 on the power supply 38. The analogue multiplexer 68 is controlled from the microprocessor 58 and from other circuit connections by signals present on address bus 93 whereby the analogue multiplexer 68 can, among other things, maintain accuracy of the system even if some of the circuit parameters drift out of specification by automatically compensating for such errors. As a result the need for further surgery to manually adjust or replace implanted components is substantially reduced.

The microprocessor 58, as indicated, is the portion of the internal control unit 16 that controls all of the various functions thereof including also the functions of communicating with the external control unit 22. The microprocessor 58 has control and other connections including data and address connections to a 1024 bit random access memory (RAM) 94 which memory is programmable from the external control unit 22. When programmed the RAM 94 will enable a patient equipped with the subject internal control unit 16 to be able to undergo hyperthermia treatment while away from or out of communication with the external control unit 22. This is an important feature of the present device because it means that therapy can proceed continuously, reliably, safely, and in a precisely controllable manner for extended periods of time without constant attention thereby enabling the patient to maintain a fairly normal lifestyle even while undergoing treatment. The RAM 94 also converts data from the MUX 68 for subsequent transmittal to the external control unit.

Other portions of the internal control unit include a 2-K read only memory (ROM) 96 which is shown as part of the microprocessor 58 itself, an universal asynchronous receive/transmit circuit (UART) 98 which is provided to couple the microprocessor 58 as well as other portions of the internal control unit 16 to the ultrasonic transmit/receive circuit 50 which converts signals between the internal and external control units.

The internal control unit 16 may include an emergency digital to analogue converter (DAC) 100 which can be connected to the ultrasonic transceiver 50 by lead 102 and connected to the power supply by way of the emergency power-off circuit 62. In addition, the internal control circuit 16 includes various circuit connections including the data bus 73 described above which has connections between the 8-bit DAC 56, the microprocessor 58, the 8-bit analogue to digital converter (ADC) 70, the RAM 94, and the UART 98. A second group of interconnections identified as the address bus 93 which provides other connections between the microprocessor 58, the analogue multiplexer (MUX) 68, the 8-bit (ADC) 70, the RAM 94, the UART 8, the 8-bit (DAC) 56, the emergency power-off circuit 62 and the trickle charge circuit 42. The circuit elements included in the internal control unit 16 may be constructed using conventional technology, and their operations will be described more in detail in connection with the flow charts shown in FIGS. 7A and 7B. In general, however, the internal control unit operates to regulate the amount, frequency, and time duration of the heat applied by the heater element 34 to establish and maintain a desired tumor temperature all of which functions depend upon the programming of the internal control unit as controlled and modified by the external controls and the tumor temperature as sensed by the temperature sensors or thermistors 36. If it is desired to maintain a predetermined temperature in the tumor the circuit will be programmed to energize the heater element 34 to some desired level to produce sufficient heat to reach the desired tumor treatment temperature. Thereafter, the amount of heat generated is determined by the voltage across the heater element 34 and will be adjusted manually or automatically. The amount of adjustment necessary will depend on the difference between normal body temperature and the desired temperature, the duration of time heat is applied, the frequency of the application of heat, changes in the temperature of the tumor as sensed by the thermistor 36, and changes that may occur in the tumor itself as the treatment proceeds. All of these and other factors can be programmed into the circuit. The amount of heat generated by the heater at any time will depend on the output word of the 8-bit DAC 56 operating through the current driver 60 as this output controls the voltage across the heater element and therefore the current flow therethrough.

The external control unit 22 shown in FIG. 2B includes the hardware and associated software necessary to effect clinical analysis of the data received from the internal control unit 16 and data from other sources that may be required. The external control unit has its own microprocessor (μP) 200 which is programmed from keyboard 202 and is part of an associated computer 203. The microprocessor 200 has outputs that feed a cathode ray tube graphics circuit 204, a cathode ray tube 206 which may have a connection from the graphics circuit 204, a printer/plotter 208 if need be and possibly a disc storage device 210. The elements 204, 206, 208 and 210 are optional depending upon the needs and sophistication of the system with which the subject device is to be used and the needs of the operator. The microprocessor 200 also has input/output connections to a power control circuit 212 and to a data control circuit 214. The main external power control circuit 212 has output leads 216, 218 and 220 which are connected to another power control circuit 222 which is part of an external power transducer (EPT) 223 and is connected to an external power inductor 224 which when used is positioned against the skin 18 adjacent to the internal power inductor 44. This is done when it is desired to trickle charge the internal power supply 38 as aforesaid. The lead 216 is the power lead, the lead 218 is the power return lead, and the lead 220 is the power control lead on which signals appear which control the charging of the power supply 38. The main external power control circuit 212 receives input power from a conventional source such as through a wall outlet and supplies power to the power control 222 and from there to the inductor 224 which is coupled to the inductor 44 to recharge the power supply battery 38 in the internal control unit 16. The use of electromagnetic coupling between an implanted power source 38 and an external power transducer through the skin as a means for maintaining energy for operating an implanted system such as disclosed herein has not been used before so far as known. Such a rechargeable supply is very important to the present system because not only is it expected that relatively large amounts of power may be required to generate the heat necessary to raise and maintain the tumor temperature at some desired level but it may be necessary to maintain these conditions for protracted periods to meet the needs of the treatment. A rechargeable power supply affords this possibility. It is also possible and contemplated to couple the external power transducer 223 to the internal power means during treatment so that at least some of the power to operate the internal control unit will be maintained and supported more directly by the external power supply particularly during periods of greatest demand. In some cases the required power may come through coupling means directly from the external power source to the heater or through some combination of external and internal power.

In like manner, the data control circuit 214 has connections on lead 226 which is a power lead, lead 228 which is a power return lead, lead 230 which is an input/output control lead, and lead 232 which is an input/output data lead to an ultrasonic transmitter/receiver means 234. The means 234 are included in an external data transducer 235 which is connected to external receiver 236 for coupling to the internal transmitter 52 of the internal unit 16, and to external transmitter 238 for coupling to the internal receiver 54. It can therefore be seen that the external power control portion 222 can be coupled to the internal power pick-up 42 through inductors 224 and 44 for charging and recharging the internal power supply 38, and simultaneously the ultrasonic transmit/receive means 234 including the associated receiver means 236 and transmitter means 238 can be coupled to the internal transmit/receive means 50 which includes transmitting portion 52 and receiving portion 54. These latter means, when coupled, can exchange data and other information between the internal and external units. In this way the internal unit can be programmed from time to time as desired, and the information gathered by the internal unit can be evaluated from time to time in the external control unit by computer means connected thereto and controlled by suitable software. The computer, using updated information from the patient as the treatment proceeds, or from time to time based on the patient's particular treatment program, can reprogram the internal control unit according to the changing needs of the patient. When exchanging data between the units, and especially when charging the power supply, it is greatly preferred that the distance between the power inductors 44 and 224 be as close as possible to minimize power loss. It is also preferred that the location of the internal and external transmission and receiving means associated with the transfer of data be relatively close to avoid transmission loss and errors. It may be desirable in some cases to mark the skin at the locations of the means 44, 52, and 54 as an aid in more accurately locating the corresponding external members to be coupled thereto especially if the units are to be separated from each other. This can also be done automatically using the computer program in the EUC in conjunction with monitoring the trickle charge circuit by way of the analogue multiplexer 68, see connection leads 240 and 242 in FIG. 2A. To this end it is preferred that all of the internal and all of the external coupling means be mounted on respective housings that facilitate proper orientation during use.

Figure 3:
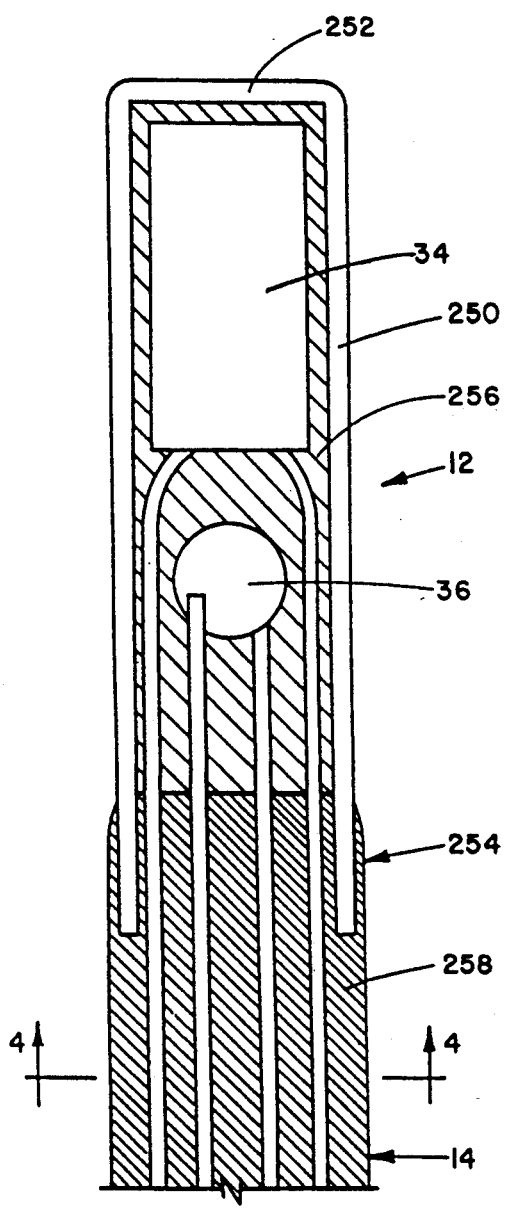
FIG. 3 is an enlarged cross-sectional view through a single element probe with a portion of cable attached thereto for use with the present device.

FIG. 3 is an enlarged cross-sectional view of a typical probe 12 of the type that might be used to treat a brain tumor using the present invention. The probe 12 is shown including an elongated tubular wall 250 closed by wall portion 252 at one end and constructed of a relatively thin inert substance such as 316L, FDA Approved stainless steel, certain plastics or glass. The diameter of the tube 12 should be as small as practical to accommodate whatever number of heater elements 34 and sensors 36 are required and the wall 250 should also be as thin as possible. A probe diameter in the range of about 1/10 of an inch or 2 millimeters is a good choice and the thickness of the wall 250 should be in a range of about 1/100 of an inch. These ranges can vary as much as several hundred percent or more. The length of the probe selected for a particular application should be selected to be long enough to extend from the cranium to the tumor treatment area. The inserted end portion of the probe may optionally be tapered at its end to facilitate its insertion in place with minimal damage to the surrounding tissue and with minimal surgical preparation. The inserted probe end wall 252 is shown as being integral with the side wall 250 and the probe edges are preferably rounded as shown. The opposite end of the probe 12 is shown connected to the cable 14 at 254 such that the cable forms a flexible continuation of the probe. The cable is preferably formed of a material such as an elastomer, and the cable 14 should be flexible enough so that it can be laid along the outer surface of the cranium, under the skin, without producing an unsightly or irritating surface condition. The heater 34 and the sensor 36 are shown embedded in a thermo-conductive electrically insulative material 256 such as a highly thermo-conductive epoxy and the cable 14 is formed of an elastomer material 258. A good selection of a highly thermo-conductive epoxy for the heat conductive material is Castall 343AB, and a typical elastomer for the cable material 258 is Dow Corning elastomer MDX-4-4210.

The internal control unit will typically be implanted under the clavicle or collar bone where there is sufficient space and where there is least discomfort to the patient. The probe 12 should be constructed to thermally and electrically isolate the heater element 34 from the heat sensor 36, and this can be done by separating them from each other as much as possible and by providing insulation therebetween, if desired. The material 256 serves this purpose to a limited extent, and it is contemplated to include other means to thermally insulate the members 34 and 36 from direct or close exposure to each other.

As indicated above, the heater element 34 and the thermistor 36 should be as small as practicable, and the selection of the thermistor for use on the subject device should take into account its impedance which should be relatively high, and it should have high stability characteristics with a negative temperature coefficient. Known glass bead type thermistors have these characteristics. A typical thermistor for use on the subject device will be approximately 2 millimeters in diameter and can have a length that may vary from a few millimeters to a centimeter or longer.

Figure 4:
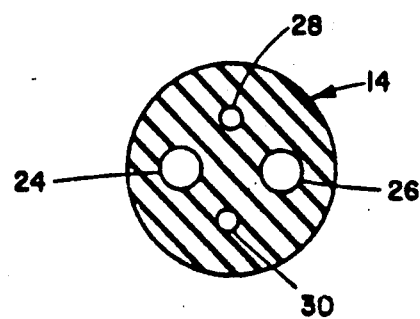
FIG. 4 is a cross-sectional view taken on line 4—4 of FIG. 3.

The cable 14 which is connected between the probe 12 including the heater element, the thermistor and the internal control unit should be as small in diameter as possible and preferably should be relatively flexible so that it will not interfere with normal body movements and will not be uncomfortable or unsightly to the patient even when implanted under the skin on the skull. The cable 14 will contain a connector 260 (FIG. 1) or plug at the end opposite from the probe 12 which mates with and makes a sealed attachment with plug means on the housing of the internal control unit. A typical cable for use on the present device is shown in cross-section in FIG. 4 and includes the two heater wires 24 and 26 and the two thermistor wires 28 and 30. The wires 24 and 26 are larger in diameter than the wires 28 and 30 because they must be able to carry sufficient current to produce the amount of heat required and programmed into the system. A typical wire size for the heater wires 24 and 26 is approximately 26 AWG solid, possibly silver wire, and a typical wire size for the thermistor wires 28 and 30 is 32 AWG solid wire. The four wires 24–30 will be insulated and will be separated from each other and from the body environment by being positioned in the single molded plastic flexible cable formed of an elastomer 258 or like material, as stated. A cable having a diameter typically in a range around approximately 1.5 millimeters is preferred. FIG. 4 shows one preferred arrangement for the wires 24–30 in the four wire cable 14. The particular arrangement of the wires 24–30 in FIG. 4 are for illustrative purposes and may be differently located in the cable 14 depending on their number and size.

The connections between the cable 14, the probe 12 and the internal control unit 16 should be made by hermetically sealed locking members or connections to prevent the intrusion of corrosive body fluids. The connections will usually be made during surgery when the system is implanted although in some situations if the cable length can be accurately determined in advance of surgery the connections can be made ahead of time to save the time and effort of the surgeon. If the connections are made ahead of time they can also be further protected by heat treating or the application of an additional sealer.

Figure 5:
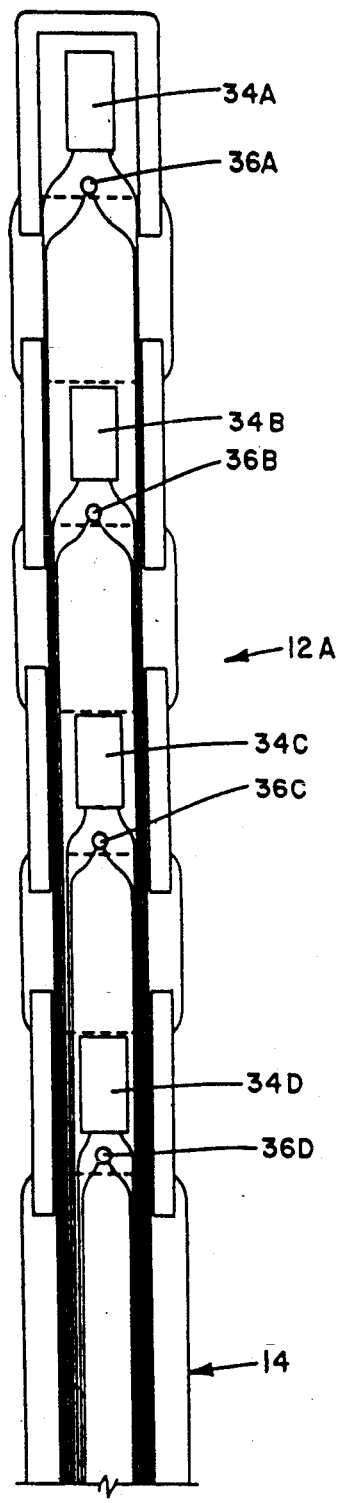
FIG. 5 is an enlarged cross-sectional view through a multiple element probe with a portion of cable attached thereto for use with the present device.

The preferred form of the probe 12 is the form 12A shown in FIG. 5 wherein the probe is an elongated member and has a plurality of spaced heater elements 34A–D and a plurality of spaced sensor elements 36A–D. In the preferred form the heater elements and sensors are alternately spaced along the device and the number of heater elements and sensors can be varied as required depending upon circumstances such as the size of the tumor and the distance over which heat is to be applied and over which the sensors are to monitor the tissue temperature. Each of the heaters 34A–D has a pair of electric connections to it as does each of the sensors 36A–D. However, because of the arrangement of the elements in the probe 12A it is necessary to have the connections for most, if not all, of the elements extend adjacent to the periphery of the probe in order to pass by the other elements. In the construction as shown this means there must be provisions for 16 wires extending between the elements and the internal control unit. This also means that the internal control unit may have separate means to power each of the different heaters and separate means to receive and store the different sensor readings.

In the usual situation only a selected one of the heater elements 34A–D will be energized at one time for treatment purposes, and selected ones of the sensors will provide temperature outputs for evaluation and other purposes. This means that there will be a relatively large space between the sensors that are being read and the heater that is being energized and the sensors being read will be relatively little affected by direct heat from the energized heater elements. This also means that the sensor temperatures being monitored or read will be more influenced by the temperature of the tissue adjacent the sensors than by the heater. Which of the heater elements is to be energized and which of the sensors are to be monitored for outputs will depend upon the programming of the systems, and the programming, which is done externally by the external computer 203, can selectively energize the several different heater elements in any desired order to generate heat at different locations along the probe, and in some cases it may even be desirable to energize more than one heater element at the same time although this is usually avoided to minimize the current drainage of the internal battery source. In one experimental application wherein a probe was placed in a rabbit's brain the current required to operate the one heater was on the order of 43.0 milliamps. If more than one heater is energized obviously the current requirements will increase correspondingly. It is also possible to use a probe having one heater element and one sensor as shown in FIG. 3, but this is usually not desired since in such a construction the sensor element or thermistor may be unduly influenced by the temperature generated by the heater element in relation to the temperature of the surrounding tissue.

It is also contemplated for experimental purposes to implant a probe extending into the tumor to be treated, as aforesaid, but to have the cable 14 extend through the patient's skin to the external control unit thereby making it possible to combine the internal and external control means into one unit. This will afford an easier way to operate the system and will reduce the surgical procedures necessary and obviate other needs for an internal power source. Such a system may afford an easier and possibly more reliable way to apply treatments, although it ties the patient to the controls for a treatment session.

Figure 6:
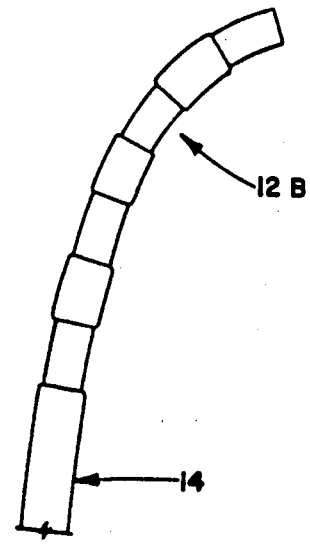
FIG. 6 is a side view of the probe and cable portion of FIG. 5 but shown in a non-linear configuration.

In addition, it is contemplated to connect and control the heaters and sensors in more than one probe from the same control unit as in a situation where it is desired to generate heat in more than one tumor or tumor location at the same time. Furthermore, the probe 12A can be formed to be other than straight as shown by the probe 12B in FIG. 6. There are thus many arrangements, shapes, and styles of probes that can be used, including more than one type of probe on a single patient, and the present invention offers the possibility of selecting different probes and probe arrangements to treat different tumors. This gives the doctor many more options for tumor treatment of cancer patients, and it does so using a device that produces minimal surgical damage to the patient as when the probe is inserted and removed. The path for inserting the probe can be prepared in advance if desired using a relatively pointed surgical instrument and the depth of penetration of the probe can be determined from data obtained using known means to accurately locate the tumor.

The ultrasonic data transceivers 50 and 234 provide the data link between the internal control unit and the external control unit. For example, the transceiver 234 in the external control unit can convert incoming serial digital data from the data control circuit 214 into bursts of ultrasonic energy to be transmitted through the skin to the transceiver 50 in the internal control unit. The transceiver 50 will then convert the data back to serial digital data that is compatible with the UART 98 in the internal control unit for use by the internal microprocessor 58 to control the various functions of the internal control unit including the programming. The RAM 94, as stated, is programmable in this fashion by the external control unit and is the portion of the internal control unit that will enable a patient to undergo hyperthermia treatment while away from the external control unit. This is an important advantage of the present system. In a similar manner, the transceiver 50 in the internal control unit can convert incoming serial data from the UART 98 into bursts of ultrasonic energy that will be received by the transceiver 234 in the external control unit and there converted back to serial digital data that will be sent to the data control circuit 214 for processing by the computer.

The external control unit, as explained, is that portion of the system that contains the operational program including the keyboard and the software for the entire system. The external control unit generally will also include a computer such as the personal computer 203, a power control circuit portion 212, a data control portion 214, an external power transducer 223 and an external data transducer 235 all connected as shown in FIG. 2B. The hardware and software in the external control unit will effect all the clinical analysis of the data including clinical analysis of information and data received from the internal control unit, and depending on the program and ata available, will make decisions as to how the therapy will proceed. The computer 203 is part of the external control unit 22 and includes the microprocessor 200 and the keyboard 202 and may also include the graphics module 204, the cathode ray tube 206, the printer/plotter 208, and the disc storage 210. These may all be off-the-shelf items. In addition to the features indicated, the computer will also contain the necessary peripherals and software to effect any clinical analyses that may be required. The external power control circuit 212 interfaces with the computer 203 and contains the necessary decoding circuitry so that the current flow in the power inductor 224 will be turned on and off under control of the operation program contained in the computer and this will also enable the operator to start and stop the trickle charge or power transfer from the external to the internal units without removing and/or repositioning the power inductor 224 and the members 236 and 238 even during prolonged periods of clinical testing. The external control circuit will also contain the necessary decoding circuitry to control the mode of operation and the sequence of the transmissions and receptions between the internal and external control units. Necessary buffer circuitry may also be required to enable receipt and transmittal of serial digital data from one unit to the other.

The external power transducer 223 which includes the power control 222 and is provided to induce current flow into the power pick-up 42 by coupling through the skin should preferably be as light weight as possible and should be easily positioned against the outside surface of the skin so that the inductor 224 will be closely adjacent to the internal inductor 44. It may be desirable to provide a monitoring routine as an aid to properly positioning the external power inductor 224 to maximize the current flow into the power pick-up 42 by maximizing the coupling to increase the power transfer efficiency.

The external data transducer 235 which includes the ultrasonic transmit/receive means 234 is the portion of the external control unit that converts incoming serial digital data from the computer 203 into bursts of ultrasonic energy for transmission to the ultrasonic receiver 54. The external data transducer 235 operates to convert signals received from the internal control unit to serial digital form for sending to the computer 203. The ultrasonic transceiver 50 serves somewhat similar functions in the internal control unit 16.

A description of the software is also necessary to a complete understanding of the present invention. The software is associated with the computer means in the external control portion of the subject device and is used to analyze information received from the internal control unit and to provide information for programming the internal control unit according to its analysis and assessment and according to the instructions it receives by operation of the keyboard. The information gathered can also be used for diagnostic purposes independently of the heater means if desired. For example, the data available from the sensors can be used to evaluate a condition prior to or following a treatment to determine if treatment is necessary or if a treatment has been successful. The various functions of the software will be described in connection with a typical treatment situation and reference should be made during this description to the flow charts shown in FIGS. 7A and 7B. It will also be assumed in this description that the internal control unit has been implanted in the patient and is working properly. Under these circumstances when power is first applied to the external control unit, the software will immediately go into an initialization testing routine. The purpose of this routine is to verify the proper operation of the system and to perform some basic testing before reaching a safe-to-continue condition. If, during this period, any failure is detected, indicating a dangerous condition to the patient as determined by monitoring certain circuits, all power will be removed from the system immediately. Such failures typically include such things as runaway or excessive heater current, an open sensor circuit, a shorted power supply, a failure of the transmission or receiver means, a failure of the data handling means, or a failure of the power coupling means. Under these conditions no application of current will be applied to the heater element 34. On the other hand, if the tests indicate that the system is operating normally, a System Normal condition will be reached and it will then be necessary for the operator to select between the automatic or the manual mode of operation. The selection made will determine the course of future operations.

If the operator selects a manual mode of operation by operating an appropriate key on the keyboard, all operations and functions of the system will be under control of the operator and the operator will then have to constantly monitor all activity occurring within the system. The operator will be aided in this by a display on the cathode ray tube 206 and/or by other means in the computer. A record of the operations may be made on the printer 208 and stored in the disc storage 210. If the manual mode of operation is selected the operator must then select the following 7 parameters before proceeding, namely;

1. An 8-bit digital to analogue converter (DAC) word. The selection of this binary word will determine the temperature that will be generated in the heater element 34 and hence in the tumor being treated. The selection of a particular 8-bit word will cause a search operation to take place in a look-up table in order to produce an appropriate temperature representation or constant. The system will stay at the constant selected to represent the desired temperature for the duration of the test.

2. The operator will select a time for the temperature that has been selected to be applied. This time will be selected by operating the appropriate key on the keyboard 202 associated with the computer 203.

3. The operator will select an address for applying to the analogue multiplexer 68 by operating another key on the keyboard 202, and this will allow the operator to monitor any or all of the connected internal test points in the internal control circuit to assure proper operation. The multiplexer 68 is shown having 8 such input connections which are connected to various portions of the circuit. Some of these 8 connections are not used in the embodiment shown in FIG. 2A.

4. The operator will operate another key which will determine the frequency that sample data will be read from the analogue multiplexer 68.

5. Another key on the keyboard 202 will be depressed to cause a trickle charge to be applied to the internal power supply or battery 38 as required. The frequency at which this is necessary will depend upon how much heat is generated by the heater element and the characteristics of the battery in the internal control unit. It is also contemplated that the internal control unit may include means for responding to the charge remaining on the battery 38 which, depending on the type of battery used, may include means to tell when the battery charge has fallen far enough to indicate a potentially dangerous condition or a condition that indicates recharging is necessary.

6. Another required input is produced by operation of a key on the keyboard 202 to enable the internal RAM 94 to store data it receives from the analogue multiplexer 68. The data thus stored can be later transmitted back to the external control unit for evaluation.

7. The operator must also determine where he wants certain of the data being monitored to go. For example, he may feed the data to the disc 210 for storage, he may feed it to the printer 208, he may feed it to the graphics display 204, and he may instruct the unit to display the information on the cathode ray tube 206. This will depend upon the available equipment in the computer portions of the external control unit.

All of the above operations and selections are made in the manual mode and when the internal and external units are coupled together as described above with the inductors 44 and 224 adjacent on another, and with the transmitter and receiver portions 52 and 54 adjacent to the receiver and transmitter portions 236 and 238 respectively.

After the above selections have been made and the operator is satisfied with the results and tests, the system will require a start command to begin actual execution of a treatment. When the RAM 94 is enabled, a command will be sent from the external control unit 22 to divert all of the analogue multiplexer 68 outputs for entry into the internal control unit RAM 94. If a trickle charge operation is required a command will also be sent to the external power transducer 223 to initiate that operation. Also, if treatment is called for, the selected 8-bit binary word or byte will be sent to the digital to analogue converter 56 for applying the appropriate voltage across the heater element or elements 34. The analogue multiplexer 68 sample rate will also be checked to see if a polling sequence is required, and if not a countdown will take place and a check made to see if the allotted time has expired. If the allotted time has expired the DAC 56 input is removed and a Time Expired display will appear on the cathode ray tube 206. The system will then await further inputs from the operator. If the allotted treatment time has not expired the program will loop and continue to see if a polling sequence should be initiated. When this happens a polling routine will read in those multiplexer inputs that were initially selected by the operator as aforesaid. The 8-bit output of the analogue to digital converter 70 will be sent to the external control unit 22 (or to the RAM 94) to be stored and/or displayed to the operator. This process will continue to repeat itself until the time has expired. This will be apparent by referring to the flow charts in FIGS. 7A and 7B.

If the operator selected the Automatic Mode instead of the manual mode he must then select 6 parameters rather than 7 before proceeding. The parameters that must be selected in the automatic mode are:

1. Final Temperature—this parameter may be specified in ° C. or any other desired temperature and is the tumor temperature that is desired to be reached as determined by the output of the sensor or sensors 36.
2. Time To Reach—this input parameter forces the software to select the proper algorithm required to raise the temperature of the heater element 34 sufficiently to reach the required tumor temperature in the requested time.
3. Time Applied—once the desired temperature in the tumor has been reached this parameter, as selected, establishes the length of time that the desired tumor temperature will be maintained.
4. Number of Cycles Required—this parameter will establish and control whether more than one cycle of treatment is required and will further specify and control the number of treatment cycles that will be produced.
5. Time Between Cycles—this parameter allows for more treatment periods during which the heater elements are deenergized and a return toward ambient conditions in the tumor will results.
6. Data Peripherals—this parameter controls what data will be stored in and/or displayed for the operator.

After the selection parameters for the automatic mode have been completed, a start command is required to begin the execution. The algorithm routine that was selected will then take over and determine how much power is to be applied to the heater element to produce the desired tumor temperature. This decision will be based mainly on the desired temperature to be reached as indicated by the sensor and on the rate of heat application required to achieve the desired temperature. Other factors affecting this include the characteristics of the tumor and the ability of the body to dissipate heat from the tumor. Once this decision is made in the algorithm routine an appropriate 8-bit command will be sent to the digital to analogue converter 56 for application of voltage to the heater element 34. The analogue multiplexer 68 will then be polled at appropriate time or times and data will be gathered, stored and analyzed, and this procedure will continue until the desired temperature as determined by the sensor or sensors 36 is reached. Once the desired tumor temperature is reached a countdown cycle may begin based on the desired time of application of heat and changes that will be made to the output of the digital to analogue converter 56 word to maintain a constant temperature condition as determined by the sensors 36. If more than one sensor 36 is used this may involve averging the outputs of the sensors to determine the heater voltage to be applied. Once the time has expired for the application of heat treatment, the cycle parameters will be checked and if the cycle is finished a display indicating that the cycle is over will appear and the operator must then initiate further actions if more cycles are required or the treatment cycle can be terminated at that point. If more cycles are required a delay period will be counted down, the parameters will be reinitialized and another status display will be put on the cathode ray tube 206 to indicate the present condition to the operator. If called for, the complete cycle or a modified cycle of treatment will be restarted.

It is also possible using the present device to store instruction commands in the RAM 94 using the external control unit 22. If this is done the external control unit can be decoupled from the internal control unit 16 and the system can operate on its own internal power supply for an extended period of time depending upon the power storage capacity of the power supply 38 and the need to recheck the circuit parameters and introduce changes in the therapy, as required.

Figure 7A:
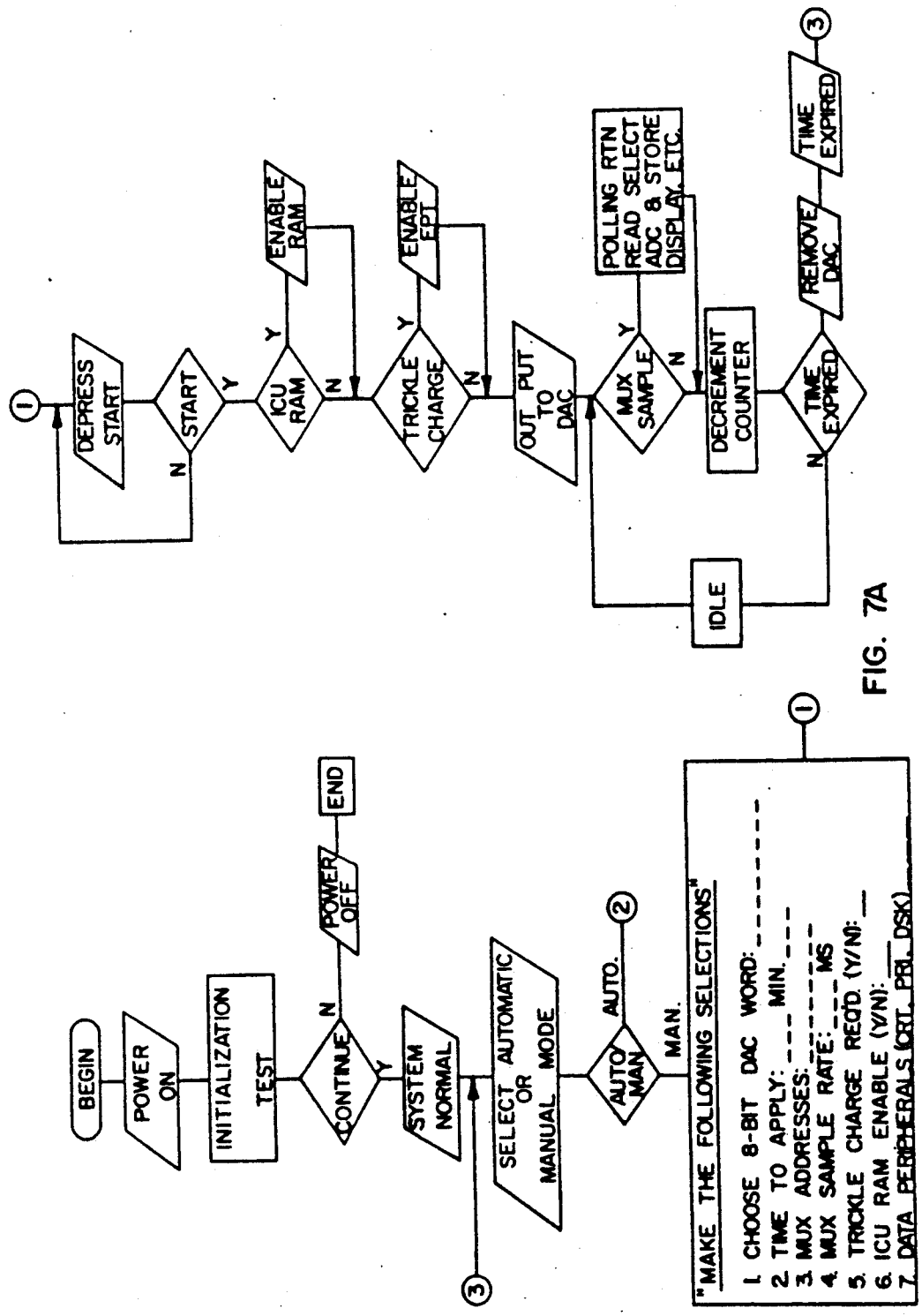
FIGS. 7A and 7B together are a flow chart for the systems shown in FIGS. 2A and 2B.
Figure 7B:
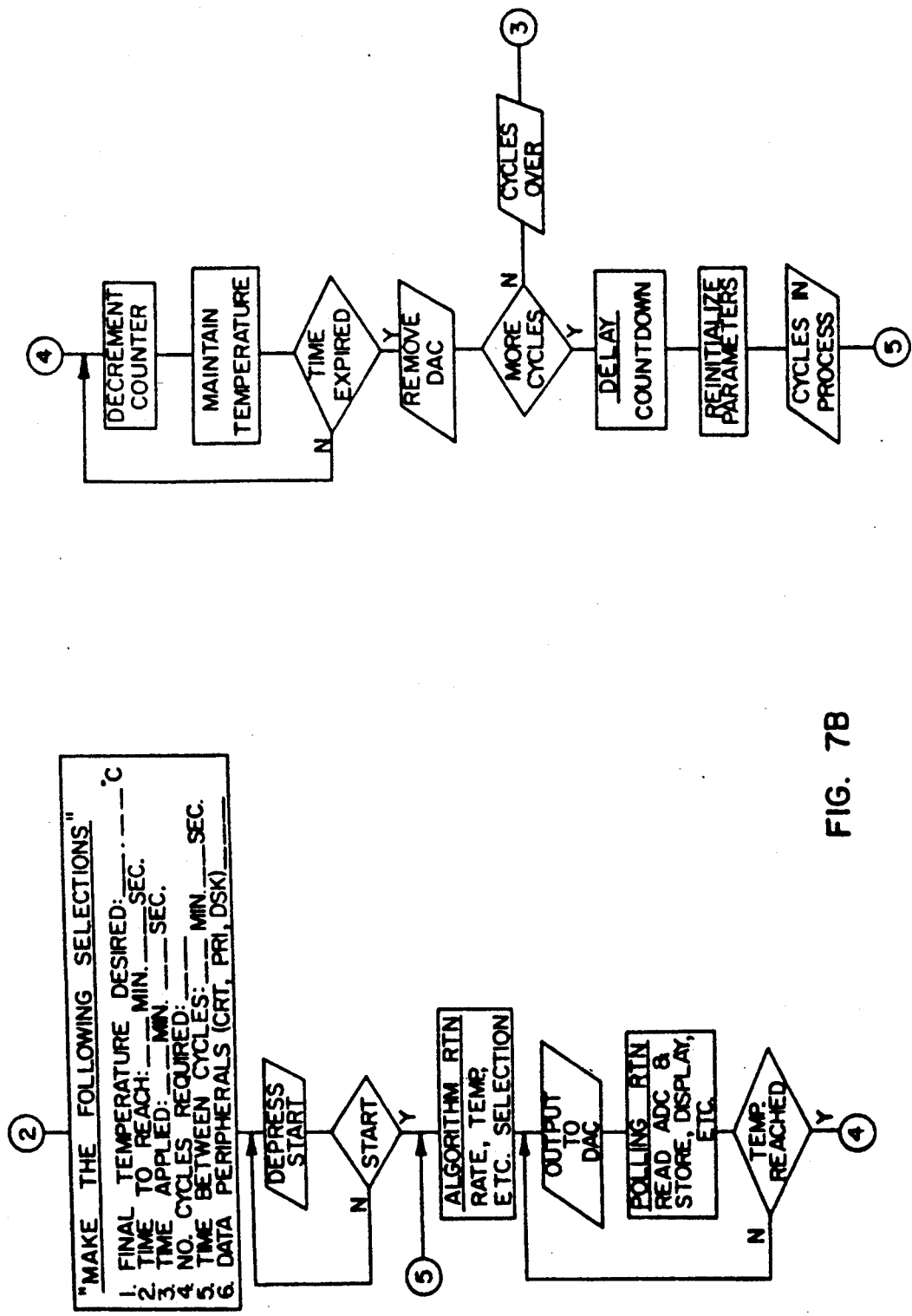

FIGS. 7A and 7B together form a flow chart for the subject device and should be considered in conjunction with the description of the manual and automatic operation as set forth above. The flow charts contain blocks which identify the various options available to the operator in the manual and automatic modes and it is believed that the above description will enable one skilled in the art to understand the flow charts.

The inputs to the multiplexer 68 may include various circuit connections including the circuit connections shown. These are used for test purposes and to verify certain circuit conditions as stated above. For example, such connections can be made to the ultrasonic transmit/receive means 50 to check the operating characteristics thereof. Similar connections could also be made to respond to the strength of the transmissions and receptions of information and this in turn could be used as a means for indicating whether the coupling between the internal and external units are properly made and are sufficient to support the necessary communications therebetween.

One of the most important aspects of the present invention resides in the fact that is provides means for introducing heat at a location that is within the tumor being treated and in such a way that all or substantially all of the heat that is generated in the heater element is generated in the tumor and radiates outwardly through the tumor and through the adjacent body portions from the heat source or heater element, and none or substantially none of the heat generated is therefore lost or ineffective. This means that the heat will be placed where it is most needed with little or no chance for damage to the surrounding tissue. This is not the case when radiation treatments are applied because the surrounding tissue and organs are exposed to the radiant energy which can cause damage thereto. In the case of brain tumors, radiation therapy frequently results in damage to brain tissue adjacent to the treatment area and this damage generally cannot be restored medically. This is not the case with the present device which does not produce any damaging radiation and concentrates the heat that is produced in the area where it is most needed. Furthermore, with the present system any desired number or probes with associated heaters and sensors can be used, the limiting factor usually being the capacity of the power supply to provide sufficient energy for all of the heaters. If a rechargeable internal power supply is used then the length of time that the device can be used when not coupled to an external source may be somewhat restricted. On the other hand, if power can be supplied to the heater elements by direct coupling with the external source then it may be possible to use any number of probes and associated heaters even for prolonged treatments. This can be an advantage in the treatment of large tumors and the treatment of more than one tumor at the same time using the same control units.

The present device can also be used with any number of heat sensors, and the sensors can be located at various positions in the tumor and if desired in the surrounding flesh and at various distances from the heater elements. This provides the possibility for determining the effectiveness of the heater element and the heat gradient in the areas being heated and it also provides the opportunity for observing the actual data changes in the heat dissipation rate which may take place as the treatment proceeds. For example, it is anticipated that the heat dissipation rate of a tumor will change as the treatment proceeds, and the ability of the circulatory system of the patient to carry away the heat during treatment may also change and this can be detected especially if multiple sensors are used. Also, if more than one sensor is used some formula or algorithm may be necessary to determine a mean average tumor temperature for control and evaluation purposes and also for the purposes of determining the temperature to be applied to the tumor by the heater elements. It can therefore be seen that the present device provides a powerful new modality or option for the treatment of body tumor and other organs, and particularly for the treatment of brain tumors which are difficult and dangerous to treat by other known means and which can be treated by the subject device with minimum damage and injury to the patient.

Figure 8:
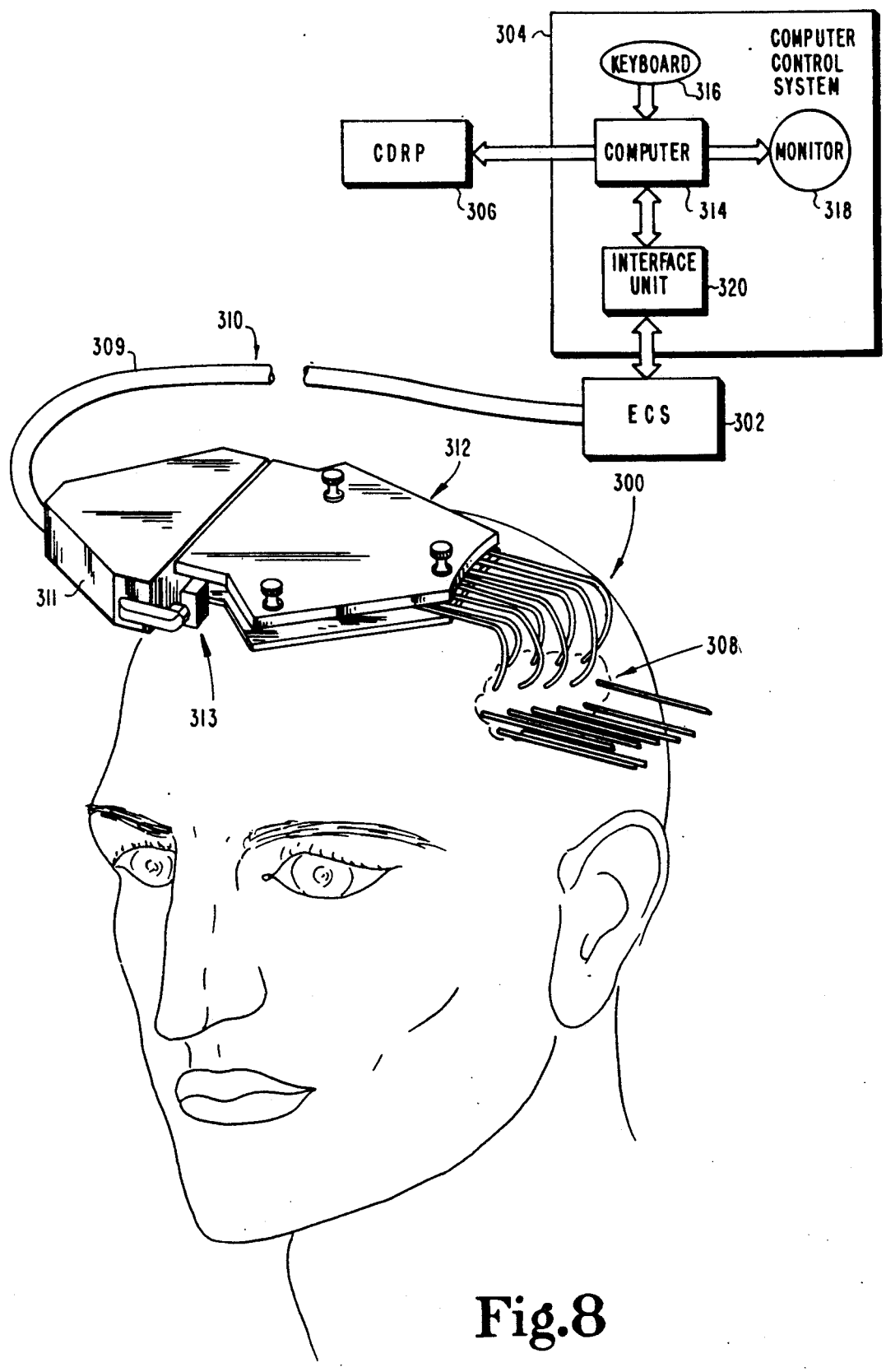
FIG. 8 is a block diagram of another embodiment of a hyperthermia system according to the present invention.

Another embodiment of the invention is shown in FIG. 8 in a typical operating environment. This embodiment is principally designed for percutaneous hyperthermia, and will therefore be referred to herein as a percutaneous hyperthermia system (PHS), although the central teachings of the invention as embodied in this system are equally applicable to other hyperthermia systems and techniques, such as the implantable system described above. In its preferred form, the PHS is composed of four major subsystems: an implantable set of probes 300, an external control system (ECS) 302, a computer control system 304, and clinical data recording peripherals (CDRP) 306. Multiple probes 300, each including a heat-emitting source, are interstitially implantable in a tumor in a predetermined pattern 308 (also shown in FIG. 10) for volumetric heating of the tumor. As will be described later in greater detail, ECS 302 is removably connected to an associated array of probes through a cable assembly 310 and a manifold connector 312, thereby enhancing patient mobility between treatment sessions.

In conjunction with a temperature control program in computer control system 304, ECS 302 controls the energizing and deenergizing of the heat-emitting elements in the probes in response to temperature sensed by thermistors in the tumor environment. The ECS contains analog and digital communication and control circuits for the above-mentioned temperature control function and for built-in-test, safety check, and automatic calibration, as will be described. The computer control system includes a computer 314, preferably an IBM PC, equipped with keyboard 316 and cathode ray tube (CRT) monitor 318 and programmed with all the operational programs for the ECS and for the CDRP. An interface unit 320 is provided for communications between the computer and ECS. Under control of a built-in-test program in computer 314, the PHS continuously monitors and tests all critical parameters of the ECS circuitry. A hard disk, printer, strip-chart recorder, and color CRT are provided in CDRP 306 to enable recording and storage of various treatment parameters for medical and technical analysis.

Figure 10:
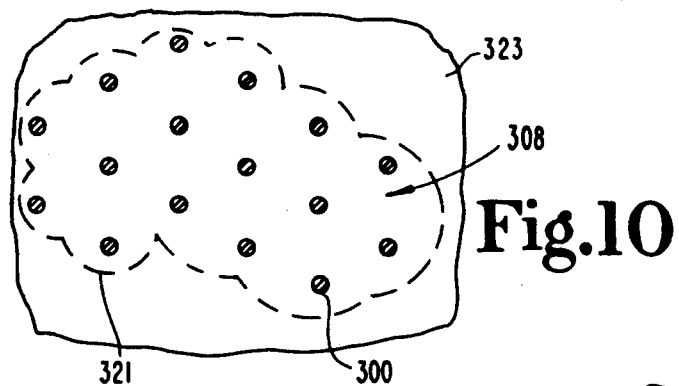
FIG. 10 is a sectional view taken along lines 10—10 of FIG. 9.
Figure 9:
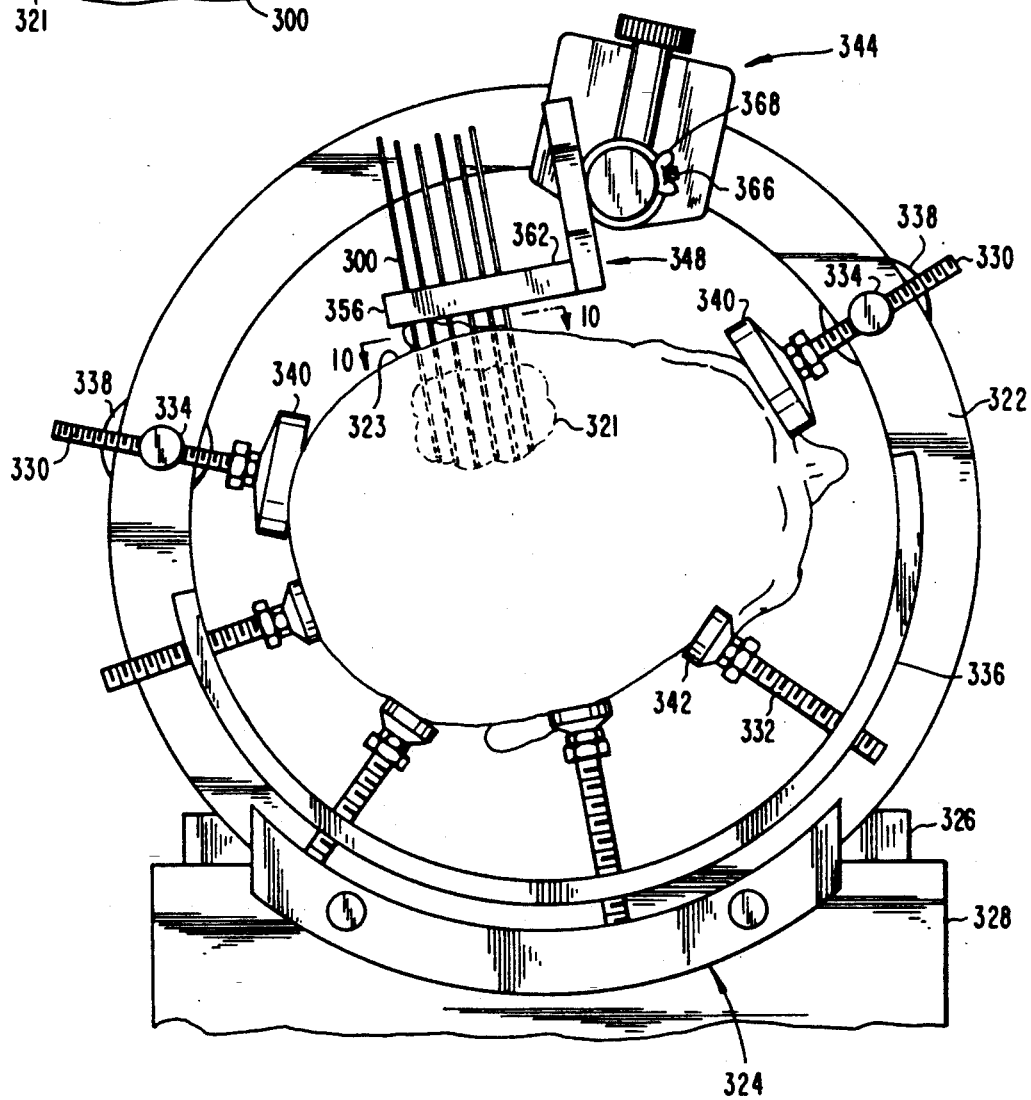
FIG. 9 shows a head end view of a patient lying on a patient cradle with a support frame in place for use in stereotaxic placement of probes according to the preferred embodiment of the present invention.

The probes are stereotaxically placed in the tumor in a predetermined pattern for volumetric heating, with an imaging system being used for guidance in the placement of probes. In this regard it should be noted that the preferred embodiment of the present invention is described herein in terms of a method and apparatus for producing hyperthermia within the brain, but that the invention may also be applicable to the neck, the chest cavity, the long bones of the body, or to other points of interest, including those not easily accessible because of overlying bones or delicate organs. Image-based stereotaxic placement of the probes is performed with an imaging system of the type having a gantry with a horizontal, cylindrical throat axially aligned with a movable patient cradle. A computerized tomography (CT) scanner is a well known form of such an imaging system and will therefore be used as a reference herein for the description of the preferred embodiment, although other imaging systems and techniques may be used, such as X-ray film, X-ray fluoroscopy, magnetic resonance imaging, electromagnetic imaging and ultrasound. FIG. 9 shows a head end view of a patient lying on a patient cradle with a support frame in place for use in stereotaxic placement of probes according to the present invention. In the illustrated view, six probes 300 are visible extending into a brain tumor 321. Ten other probes are hidden from view in the background of FIG. 9, for a total of 16 probes in this example, as shown in FIG. 10, which is a sectional view taken along lines 10—10 of FIG. 9, i.e., an axial view of the array of probes 300. Only the skull portion 323 immediately surrounding the tumor mass 321 is shown, and the foreground of FIG. 9 is shown at the top of the drawing. FIG. 10 illustrates the preferred probe pattern for volumetric heating of the illustrated tumor 321. As used herein, volumetric heating means heating an entire volume of a target mass above a minimum temperature. The resulting temperature distributions in planes perpendicular to the probes are of the type shown in FIG. 12, as will be further explained later.

The support frame for the patient's head includes a ring-like member or ring 322 encircling the head and clamped on its lower end to a ring mount generally designated 324. An adapter 326 mounts ring mount 324 to the head end 328 of the patient cradle. The details of the structure for mounting the ring frame to the patient cradle are disclosed in U.S. Pat. No. 4,360,028 to Barbier et al., which patent is hereby incorporated by reference. With combined reference to FIG. 9 and to FIG. 11, which shows a perspective view of the support frame, the support frame includes upper support rods 330 and lower support rods 332 mounted to ring 322 by spacers 334 and plastic shell 336, respectively. Upper support rods 330 are threadably engaged in spacers 334 which are mechanically linked to knobs 338. Each upper support rod 330 has a plastic cushion 340 pivotably mounted on one end. Patient support rods 332 each have a threaded shaft threadably engaged in shell 336 and a cone-shaped cushion 342 mounted on one end as shown.

The support frame also includes a template carriage 344 slidably mounted on ring 322. Two tension knobs 346 are provided for clamping carriage 344 in a desired position on ring 322. A template 348 is mounted on a tubular extension arm 350 rotatably and slidably mounted in a bore 352 extending through template carriage 344 in a direction perpendicular to the plane of ring 322. Tension knob 354 is provided to lock extension arm 350 in a desired position within bore 352.

Template 348 includes a main template block 356 formed of a radiolucent material and provided with an array of holes 358 for probe guidance and a set of holes 360 for optically coded identification of the orientation of the template in any particular image produced by the imaging system. Holes 358 and 360 all extend through template block 356 in a direction perpendicular to the top surface 362 thereof. Template 348 further includes a pair of slots 364 for vertical movement of template 348 with respect to tubular extension arm 350, the template being secured to extension arm 350 with a pair of bolts 366 and a pair of wing nuts 368 attached respectively thereto, each of the slots being provided with a seat 370 to restrain the head of bolt 366. In operation, after a patient has been placed on the patient cradle in a desired position with the head oriented, supported and restrained in a desired manner in the support frame, template 348 is moved into a desired position and orientation with respect to a tumor by adjustment of template carriage 344 on ring 322 and of tubular extension arm 350 within bore 352 of template carriage 344 and adjustment of the position of bolts 366 in slots 364 of the template. As will be described later in greater detail, once the template is positioned it is used as a guide for drilling entry holes through the patient's skull in line with predetermined locations in the tumor to be treated, and then a probe is interstitially implanted by insertion through each of the drilled holes.

The percutaneous hyperthermia system described above is preferably used with an array of probes of the type shown in FIGS. 13 and 14. The implantable probe consists of a semi-rigid portion 380 which is directly implanted into the tumor, a flexible portion 382 which remains outside the body, and a connector portion 384 for releasably mating to a manifold connector. The semi-rigid portion 380 has been designed to give the proper rigidity for insertion balanced with the desired flexibility for implantation. The flexible portion 382 prevents injury to the tissue adjacent to the probe by minimizing torque transmission from the manifold connection. The probe has been designed with the smallest possible diameter to minimize disturbance of tissue, displacement of destruction of important structures, and injury to blood vessels and yet large enough to adequately conduct heat with acceptable surface temperatures. The tip 386 of the probe has been tapered so that the tip selects a point of penetration of tissue and the rest of the probe follows the same path, minimizing distortion of tissue and injury to blood vessels.

The probe provides the medium to introduce heat energy into the tumor environment. Within the semi-rigid portion 380 of the probe is a cylindrical, thermally conductive plastic (preferably polycarbonate) tube 388 around which a resistive heating wire 390 is wound and in which an accurate thermistor 392 is positioned. The resistive heating element directly heats the thermistor through the conductive material of tube 388. The heating element and thermistors are connected to the external control system circuitry by insulated electrical wires which extend through the semi-rigid and flexible portions to the end connector portion 384. More specifically, heater 390 has one end connected to connector terminal 384$a$ and another end connected to terminal 384$b$, thermistor 392 has one lead connected to terminal 384$c$ and another lead connected to terminal 384$d$, and thermistor 393 has one lead connected to terminal 384$d$ and another lead connected to terminal 384$e$. Approximate typical probe dimensions which have been found useful in brain tissue are as follows: 9-12 cm for the semi-rigid portion, 5 cm for the flexible portion, 1-10 cm for the heater coil, and 2.2 mm for probe outer diameter.

The semi-rigid outersheath portion 380 of the probe is constructed of high-density polyethylene material or other suitably conductive material because of the need for heat transfer and temperature response. The semi-rigid portion also buffers the heat passing through allowing a more uniform heat distribution across the outer surface to reduce the effects of wirewound heaters. The thermal buffer effect of the outer sheath further protects blood vessels and tissue from high temperatures. As the heat transfer away from the outer sheath increases, the temperature of the outer surface decreases with respect to the heater temperature. In such case as a major blood vessel is adjacent to the probes, excessive heat will not be conducted to the flowing blood because the heat transfer will be limited by the outer sheath. However, within normally perfused or typical tumor tissue the surface temperature is elevated and can be carefully controlled. The surface temperature can be calculated from the power delivered and the physical properties of the probe.

Alternatively, the probes are configured as heater probes and remote sensor probes, the heater probes each having a heater and heater thermistor, and the sensor probes each having only a tissue thermistor. Whereas, in the embodiment of FIG. 14, the tissue thermistor is located relatively remote from the heater coil, the tissue thermistor in a sensor probe is located at the distal end of the central lumen, adjacent the probe tip, and is centered on the longitudinal axis of the probe.

The internal wiring is similar to that described above for the probe having two thermistors, except that in the heater probe four separate terminals are provided, one for each lead of the heater coil and heater thermistor, and that in the sensor probe only two terminals are provided, one for each lead of the tissue thermistor. The sensor probes are preferably implanted in locations equally spaced from three heater probes equally spaced from each other, for purposes of measuring the intermediate temperature.

Figure 15:
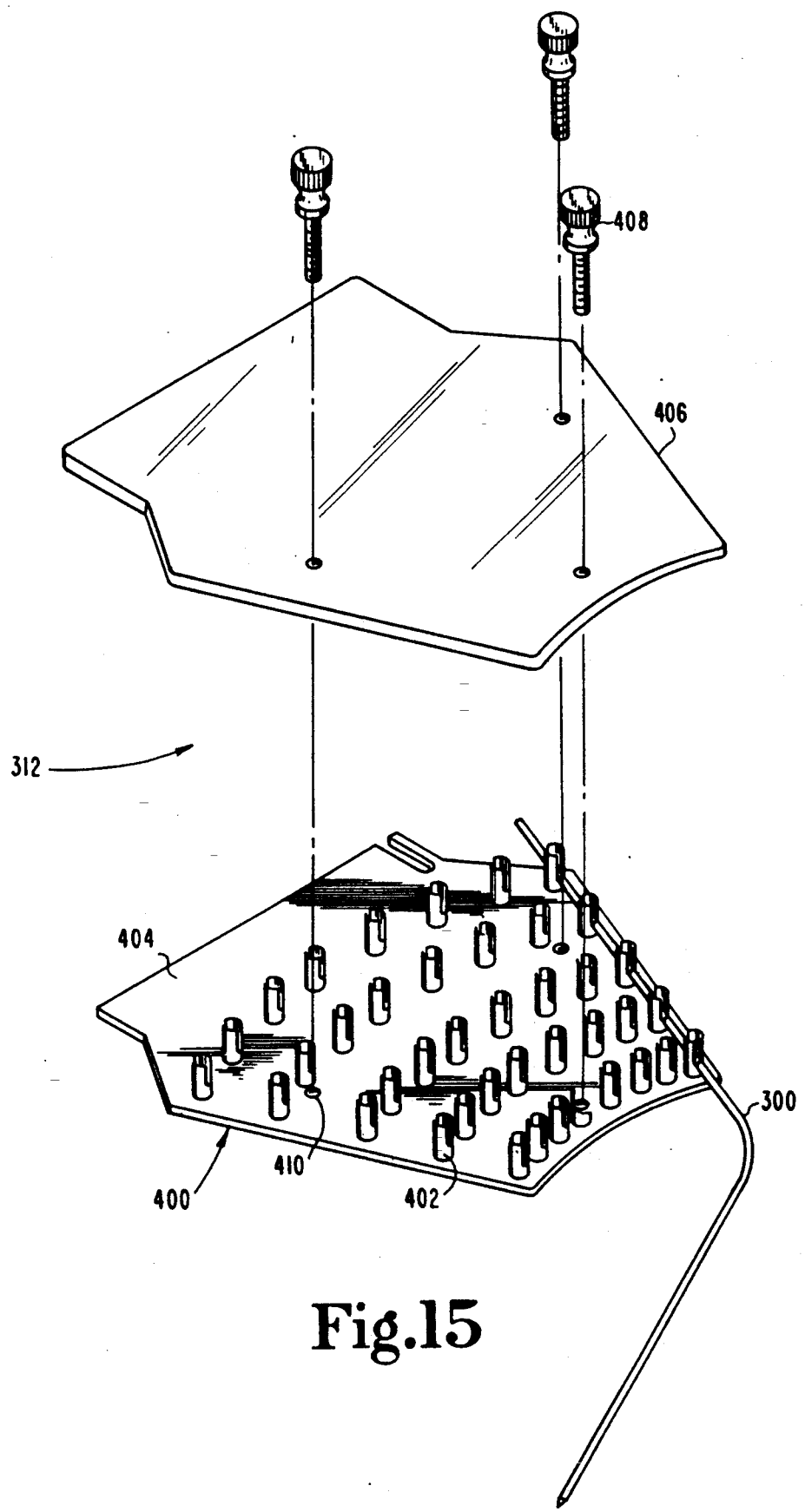
FIG. 15 is an exploded view of the manifold connector.

After implantation the probes are secured by means of an external structure to prevent migration or movement during treatment. One implementation is the attachment of a sheet material to the skin through which the probes are placed and to which the probes are then secured, such as by a mechanical securing bracket or a chemical cement which affixes the probes to the sheet. Alternatively, a casting material such as plaster of paris or water-activated polyurethane is placed around the probes and activated after all probes are in place. With reference once again to FIG. 8, the probes are then connected in groups to manifold connectors such as connector 312, each of which is connected to an individual ECS which is in turn coupled to computer 314 through a separate interface unit. In the disclosed embodiment each ECS and its associated manifold connector are associated with up to eight probes, and consequently multiple external control systems and manifold connectors are employed in cases requiring treatment with more than eight probes. The systems are preferably arranged in combinations of master and slave or slaves, and reference will be made herein to alternative configurations of an ECS with associated probes as a master PHS and a slave PHS. Each slave is connected to its associated master and also, like every ECS, to a computer interface. Unless otherwise indicated, the description herein applies equally to master and slave. Cable assembly 310 interconnecting ECS 302 and manifold connector 312 includes a cable 309 connected via an intermediate coupler 311 to a zero-insertion-force (ZIF) card-edge connector 313 which provides releasable connections to manifold 312. As shown in an exploded view in FIG. 15, each manifold connector has a substrate 400 having 40 slotted terminals 402 mounted on one surface thereof in eight angularly spaced rows of five terminals each, one row for each probe, as illustrated by the placement of probe 300. Substrate 400 is provided with a two-sided printed circuit (not shown) with a separate trace from each terminal 402 to a respective terminal of printed-circuit edge connector 404 which is adapted to mate mechanically and electrically with ZIF connector 313. The probes are held in place in the slotted terminals of the connector circuit board with a Plexiglas ® cover 406 secured to the tops of the slotted terminals by three nylon bolts 408 engaged in three threaded holes 410 provided in the substrate for this purpose.

Alternatively, separate manifold connectors are used for heater and sensor probes, each heater probe connector having 16 slotted terminals of the type described above, arranged in four parallel lines of four terminals each, one line for each of four probes. Similarly, each sensor probe connector has eight slotted terminals arranged in four parallel lines of two terminals each, one line for each of four probes. Two heater probes and two sensor probes can be connected to each ECS, and the cable assembly for each ECS accordingly includes a four-way coupler connected to the ECS by a single multiconductor cable and individually removably connected to four multiconductor cables running to the four manifold connectors. To facilitate manual connection of implanted probes into manifold connectors without interference from attached electrical cables, an additional electrical connector is provided on the manifold end of each of the latter four cables.

Figure 16:
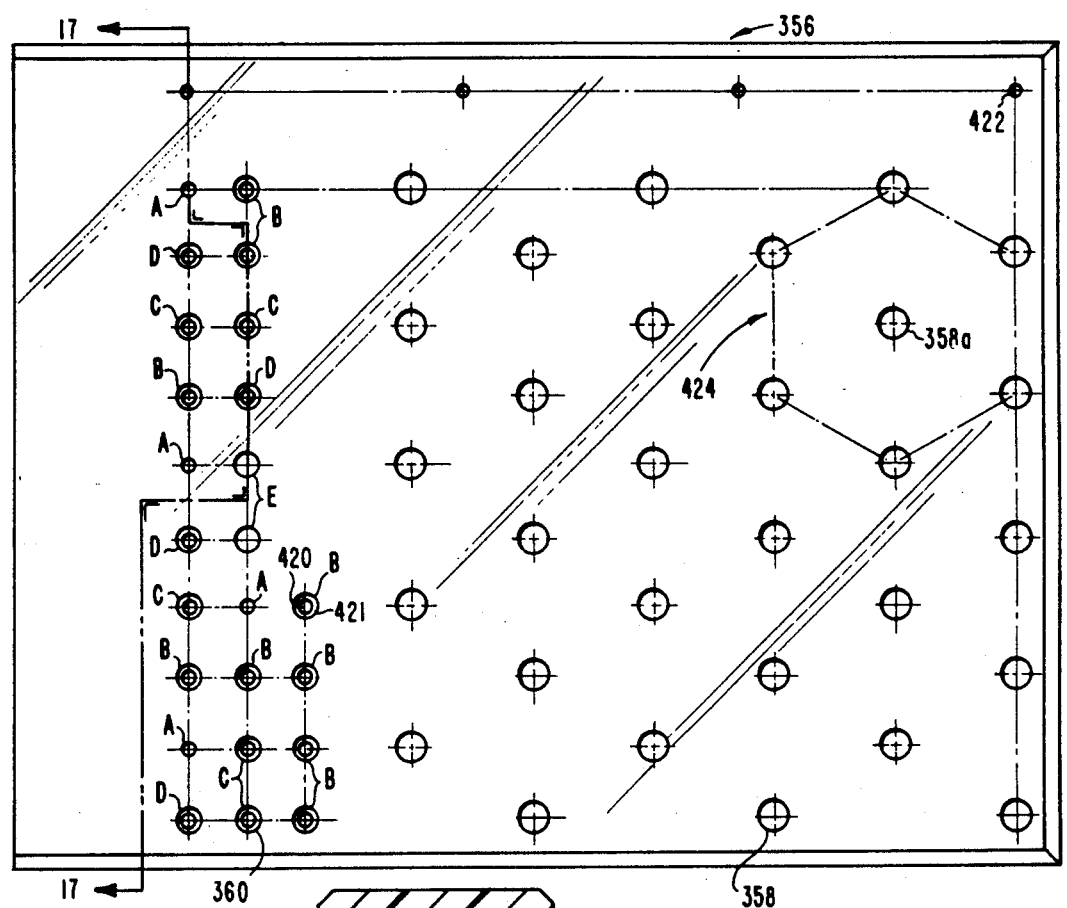
FIGS. 16-20 illustrate templates according to the preferred embodiment of the present invention.
Figure 17:
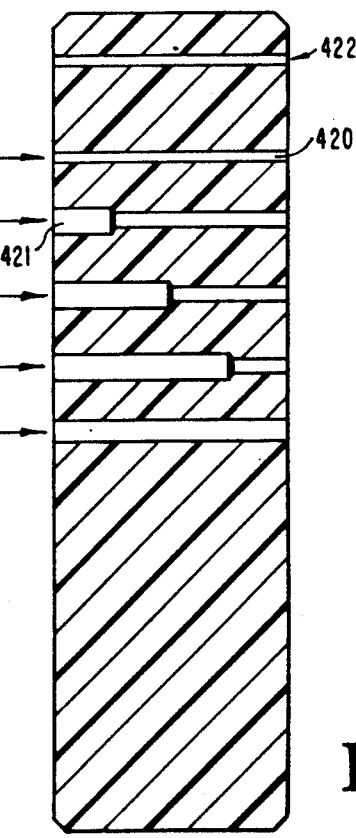

The main template block 356 of template 348 is shown in greater detail in FIG. 16, which is a top view of the template block drawn to scale, and in FIG. 17, which is a cross-sectional view of the template block taken along lines 17—17 in FIG. 16. Template block 356 is preferably approximately 4.4 inches long, 3.4 inches wide and 1 inch thick. Drill holes 358 are arranged in a predetermined pattern to facilitate volumetric heating. More specifically, the holes are arranged in a pattern of contiguous equilateral triangles, or, in other words, a hexagonal pattern with a center hole 358a in the center of each complete hexagon 424. This particular hole pattern has been found particularly desirable for volumetric heating of tumors. Five types of guide holes 360 (types A-E as shown in FIG. 16) are provided as an optical code for identifying specific rows of the template in CT images generated during probe implantation. As shown in FIG. 17, the guide holes are coded by combinations of a base hole diameter 420 (approximately 0.06 inches) and a counterbore 421 (approximately 0.1 inches in diameter), as set forth below in terms of counterbore depth:

| Hole Type | Counterbore |
| --- | --- |
| A | None |
| B | 0.250 inches |
| C | 0.500 inches |
| D | 0.750 inches |
| E | Through-hole |

Figure 11:
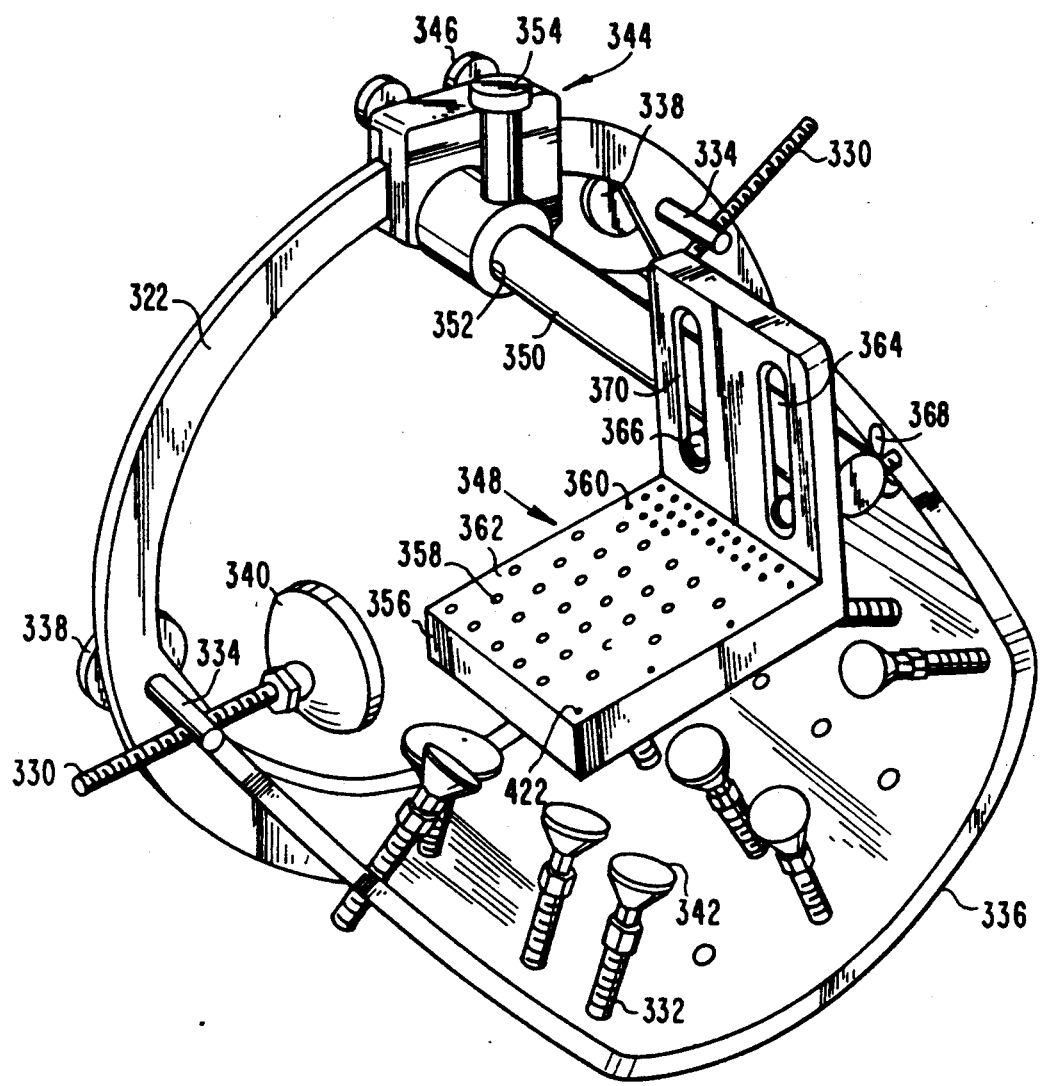
FIG. 11 is a perspective view of the support frame shown in FIG. 9.

As seen at the top of FIG. 16, the template also includes four alignment holes 422 arranged in a row. These alignment holes are threaded to receive screws which are used to fasten a laser-alignment strip (not shown) on each side of the template. The pattern of drill holes 358 includes ten rows parallel to the row alignment holes 422, each row of drill holes 358 having a set of guide holes 360 aligned therewith. When mounted on the support frames as shown in FIGS. 9 and 11, each row is parallel to the plane of ring 322 and is thereby parallel to the scan plane of the CT during use. The template is positioned such that a row of holes is visible in each CT slice, and the individual slices are distinguished with the aid of the coded holes 360. The CT is used to measure the required depth of penetration, with respect to the template, for production of hyperthermia only in the desired treatment volume, and the template is used to guide a drill bit used to drill a small entry aperture in the skull. The probes are then placed through the template into the brain tumor, constrained to the separation of apertures in the template and resulting in a parallel arrangement of implanted probes. In an application involving solid tissue resistant to penetration, a trocar is used to develop a tract for placement of a probe. The trocar preferably includes a tube for supporting the probe, an index to insure correct penetration depth and a fixture to retain probe placement while the probe supporting tube is retracted.

Figure 18:
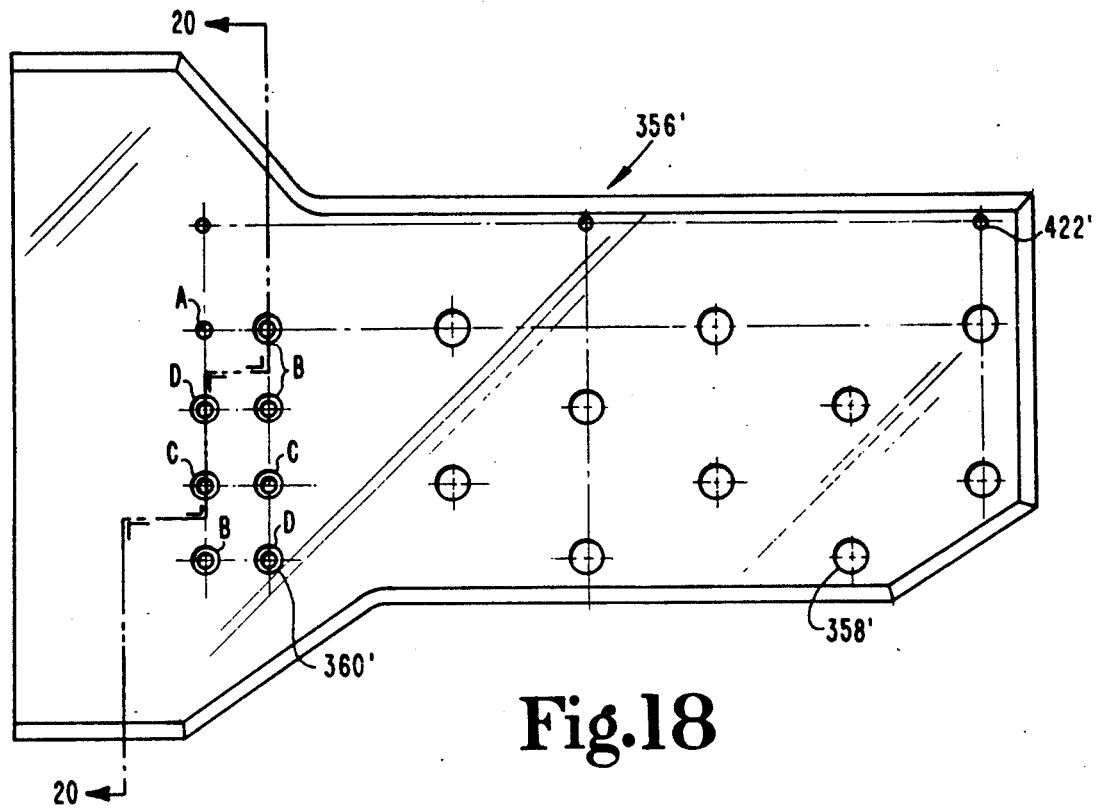
Figure 19:
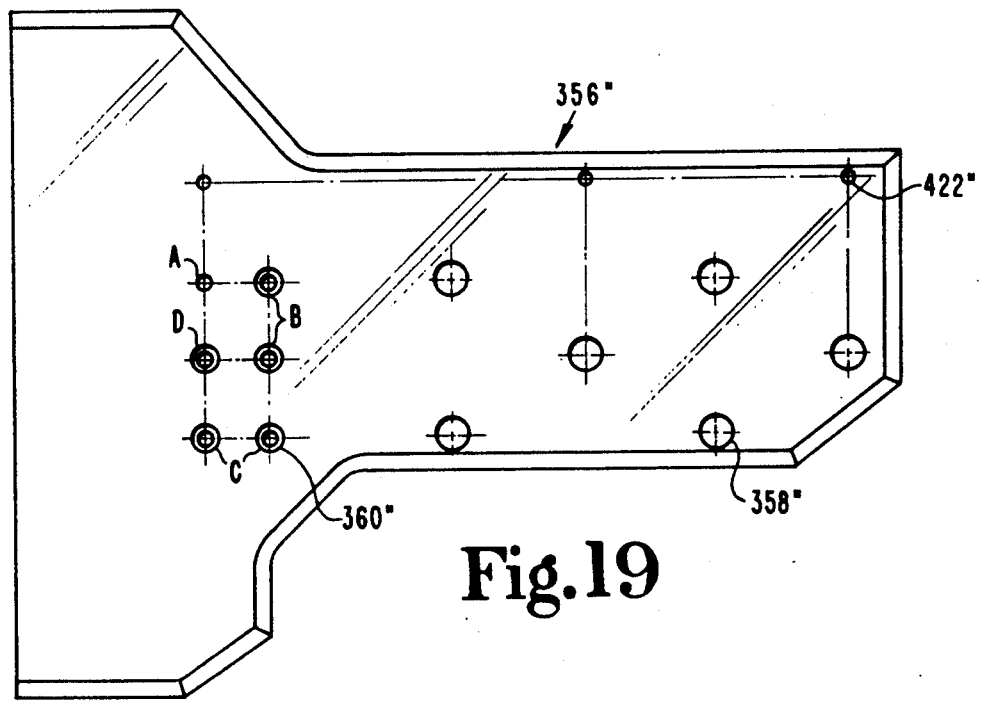
Figure 20:
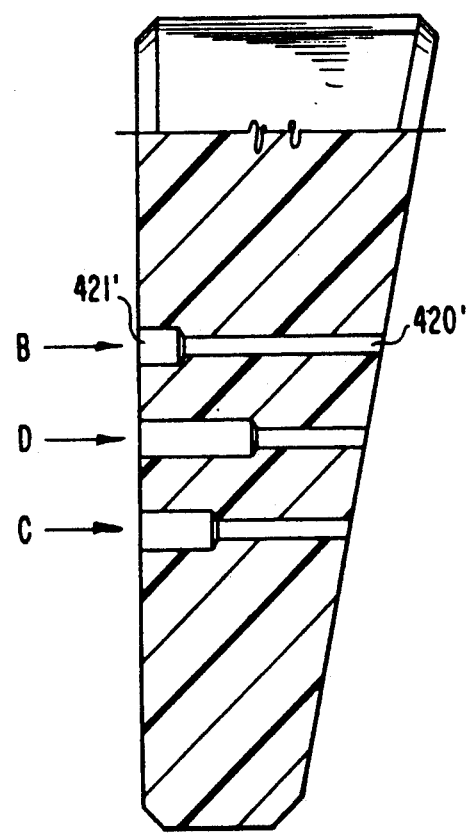

For tumors of smaller size, smaller template blocks such as those shown in FIGS. 18-20, also drawn to scale, may be used. Template 356' and 356" have maximum lengths of approximately 3.9 and 3.4 inches, respectively, and a maximum width of approximately 2.6 inches each. Both template blocks 356' and 356" are tapered as shown in the cross-sectional view of FIG. 20 and have a maximum thickness of approximately 1 inch. These template blocks have abbreviated forms of the hole pattern of template block 356 (FIG. 16) and use the same coding scheme for row identification, although with fewer holes, as illustrated. There are four types of holes 360' and 360", coded by combinations of the same base and counterbore diameters mentioned above, as set forth below in terms of counterbore depth:

| Hole Type | Counterbore |
|---|---|
| A | None |
| B | 0.125 inches |
| C | 0.250 inches |
| D | 0.375 inches |

The tapered cross-section of the template block facilitates positioning with respect to a sloped surface such as is encountered on a patient's skull. It is also contemplated that template block 356 may have a wedge portion on its underside tapering downwardly away from the center of the template block. The wedge may extend either partially or all the way across the underside of the template block, either longitudinally or laterally, and the bottom edge of the wedge may be in the plane of one of the sides of the template block or may lie in some other vertical plane through the template block.

ECS 302 will now be described in further detail, with reference to FIGS. 21A and 21B, which combine to form an electrical schematic of the system shown in FIG. 8, including probes 300, computer 314, keyboard 316, monitor 318 and CDRP 306, and additionally including a slave PHS 450 which, through an associated optoisolator 452, is controlled by ECS 302 operating as a master PHS in a manner which will be described. Command and control signals for the ECS are supplied from ports A and C of the computer through an optoisolator 454 to a digital-to-analog converter (DAC) circuit 456 and a control decoder 458, respectively, while feedback and status signals are coupled from an analog-to-digital (A/D) converter 460 and a status buffer 462 through optoisolator 454 to port B of the computer. As will be described later, five out of eight output lines from port A are also connected to an analog multiplexer (MUX) 464 on the MUXSEL lines, for selection of the input to A/D converter 460. DAC circuit 456 contains an eight-bit DAC, preferably a Datel UP8B, and output power amplifier for each heater 390, for generation of individual heater command voltages. The data inputs of the DACs are connected in parallel to the data bus from port A, and individual DAC loading is enabled through the control decoder. The heater command voltage lines are separate but are depicted collectively as a bus in FIG. 21B to simplify the drawing, and, correspondingly, block 466 depicts a single circuit of the type which is separately provided for each line in the bus. Single line connections to circuit block 466 represent common connections to all circuits therein. An individual bar graph, preferably type TSM3915 available from III V Semiconductor, Inc., is provided in a bar graph circuit 468 for each heater command voltage output line from DAC circuit 456.

Various parameters associated with the treatment are monitored by the PHS, including individual heater voltages (HTRV), heater currents (HTRI), and heater and tissue temperatures as measured by heater thermistor (HEATER THERM) 392 and tissue thermistor (TISSUE THERM) 393, respectively. HTRV sense circuit 484 is an attenuator having one voltage divider for each heater command voltage line. Heater current sensing is provided by HTRI sense circuit 486 which has a one-ohm current-sense resistor for each heater as a terminating resistance to analog ground, and a buffer amplifier having its input connected to the current-sense resistor and its output connected to MUX 464. For calibration purposes, three reference voltages are derived from a single ten-volt reference in voltage reference (VREF) circuit 488 and supplied therefrom to MUX 464. The ECS includes a power supply (not shown) for generation of all the necessary DC voltages as described herein, and also includes a power monitor 490 for monitoring various conditions in the power supply. For one of these conditions, power supply temperature, the power monitor generates both analog and digital indications, and the analog value is supplied to MUX 464. Periodically, each of the above-identified parameters is selected through MUX 464, and the selected value is converted to a digital value in A/D converter 460 and coupled to port B of the computer through optoisolator 454. Parameter selection is made using the MUXSEL and MUXCLK control lines to MUX 464. A/D converter 460 is preferably an eight-bit, three-state device, such as Datel ADC-ET8B, connected in parallel with status buffer 462, which is also preferably an eight-bit, three-state device. A/D converter 460 is controlled through control decoder 458 via two control lines 470, one connected to a start input for initiating conversion and the other connected to an enable input for control of the converter output. Busy status of the A/D converter is conveyed by a single output line to status buffer 462.

Status buffer 462 is a set of three octal buffers with three-state outputs and separate buffer enable inputs. The data inputs to the status buffer enable inputs. The data inputs to the status buffer are as depicted in FIG. 21A, with buses used as appropriate to depict multiple signal lines. The OTEMP signals are alarm signals which are individually generated in response to heater overtemperature (HTR OTEMP) conditions. The PWRMON status signals represent the conditions of temperature and voltage in the power supply, and manifold connection (MANCONN) status is indicated by the MANCONN signal. The LATCH signals are latched samples of other status signals, as will be described. The RELEASED and MRLY status signals indicate particular conditions in a master control circuit 472 which provides a master control for all probes and also generates a control signal (REMOTETX) for control of slave PHS 450. The return signal (REMOTERX) from slave PHS 450 through optoisolator 452 is coupled to the master control circuit and is also supplied to the status buffer. The status buffer also receives status signals from a watchdog timer 473, a treatment lamp (TREAT LAMP) circuit 474, a treatment control (TREAT CONTROL) circuit 475, and a stop lamp circuit 476, as illustrated in FIG. 21A. The watchdog timer is used to ensure against uncontrolled ECS operation: a system shutdown occurs in the event that necessary periodic inputs from the computer are not received. Treatment lamp circuit 474, treatment control circuit 475, and stop lamp circuit 476 have control switches and indicator lamps which are used for initiating, terminating and monitoring ECS operation.

The majority of the control signals for the ECS are coupled through control decoder 458, as shown in FIG. 21A. The control lines for DAC circuit 456 and status buffer 462 have already been explained. A RELEASE line and two master relay control (MRCON) lines are directly connected to master control circuit 472 for purposes of enabling, setting and clearing particular logic circuits in the master control circuit, as will be explained. Control and indicator circuits 473, 474, 475 and 476 all have outputs connected to status buffer 462, as has already been explained, and additionally have control inputs connected to control decoder 458. Watchdog timer 473 receives a trigger (T or DOG-TRIG) signal and a set (S or DOGSET) signal, and each of the other control and indicator circuits has a set (S) input and a clear (CLR) input. The DOG and STOP lines are additionally coupled to the master control circuit as additional control lines, as will be explained. Additional control lines provided by control decoder 458 include the MUXCLK lines, for parameter selection in MUX 464, and the overtemp control (OTEMPC) lines provided for control of HTR OTEMP circuit 482.

Master relay 480 is provided as a common control for all electrical connections to the probes. It enables complete electrical isolation of a patient without disconnecting any manifold connectors, and thereby provides an added margin of safety. As shown in FIG. 21B, both ends of each heater 390 are connected to a heater relay 494, one end of each thermistor is connected to a thermistor relay 496, and the other end of each thermistor is connected to one terminal of the master relay. Each thermistor relay terminal has an individual connection to an input of MUX 464 and also (not shown) a terminating resistance to ground for the associated thermistor. Although not shown in the drawing, a manifold connector is electrically located between each probe 300 and the ECS circuitry, as has already been described. Both coils (C) of the heater relay are connected to control circuitry in the ECS. Thus, the heater relay for any heater opens when either the master relay opens or the heater relay return (HRRTN) line assumes a high (logic 1) state as determined by HTR OTEMP circuit 482 in response to an overtemperature condition in the heater. The thermistor relays are controlled only by the master relay, one end of each thermistor relay coil being grounded. The master relay itself has one coil end connected to +5 volts DC, and is controlled by the master control circuit through the master relay return (MRRTN) line. With the master relay closed and with no overtemperature conditions, each heater is connected to its respective heater command voltage line and HTRI sense line, each thermistor common connection is connected to VREF circuit 488, and the other end of each thermistor is connected to its respective multiplexer input.

Temperature and voltage conditions in the ECS power supply are monitored by power monitor 490 which generates the analog and digital signals indicated above. Manifold sense circuit 492 senses the state of the manifold connector and generates the MANCONN signal indicated above.

Figure 22:
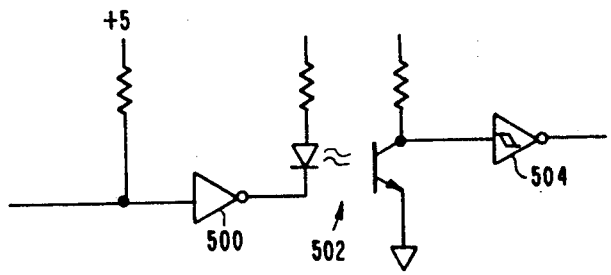
FIGS. 22-24 are electrical schematics of the optoisolator shown in FIG. 21.
Figure 23:
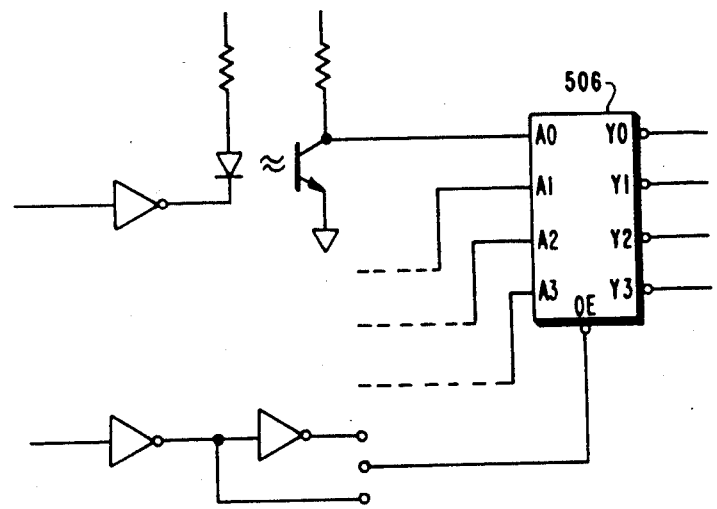
Figure 24:
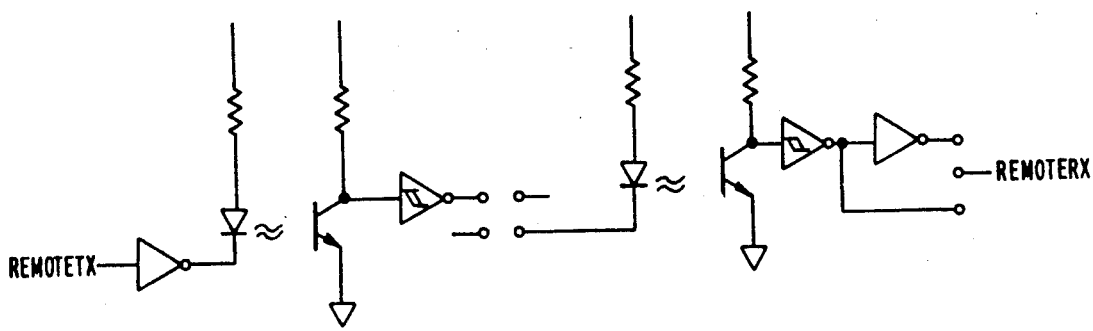

The optoisolator provides complete optical isolation between the computer control system and the ECS. FIG. 22 shows the basic building block for the optical isolation circuitry provided for outgoing signals from ports A and C of the computer. The circuit includes a 74HC04 inverter 500 connected to an ILQ2 optoisolator 502 which is in turn connected to a 74HC14 Schmitt trigger 504, and additionally includes appropriate pull-up resistors as shown. Except as indicated, all digital logic in the ECS is HCMOS. Sixteen of these circuits are provided in each ECS, one for each of pins 0-7 of port A and pins 0-7 of port C. A similar isolation circuit is provided for incoming signals to port B, as shown in FIG. 23. This circuit includes the same type of inverters and optoisolators as those shown in FIG. 22, and additionally includes two four-bit latches 506, one of which is shown in FIG. 23 with one of its four inputs from an optoisolator, the other three inputs being identical to the first and consequently not shown for simplicity of illustration. The state of the latch is controlled by pin 6 of port C of the computer, which is connected through a pair of inverters and a configuration jumper to the enable line (OE) of each latch. One jumper connection is made for a master PHS, and the opposite jumper connection is made for a slave PHS, thereby enabling selectable communication from computer port B under control of pin 6 of computer port C. A total of eight latched output lines are provided, one for each of input terminals 0-7 of port B. Optical isolation is also provided between ECS 302, which is the master PHS, and slave PHS 450, as shown in block diagram form in FIG. 21 and schematically in FIG. 24. The REMOTETX line is isolated from the input line to the slave PHS by an inverter, optoisolator, and Schmitt trigger of the type shown in FIG. 22, and similarly the REMOTERX line is isolated from the output line of the slave PHS by an optoisolator coupled to a Schmitt trigger having one output connected directly to a jumper line and another output connected through an inverter to another terminal of that jumper line. It should be noted that FIG. 24 also illustrates the internal circuitry of optoisolator 452, which, along with circuitry of the type shown in FIGS. 22 and 23, makes up the optoisolator circuit of the slave PHS.

Figure 25:
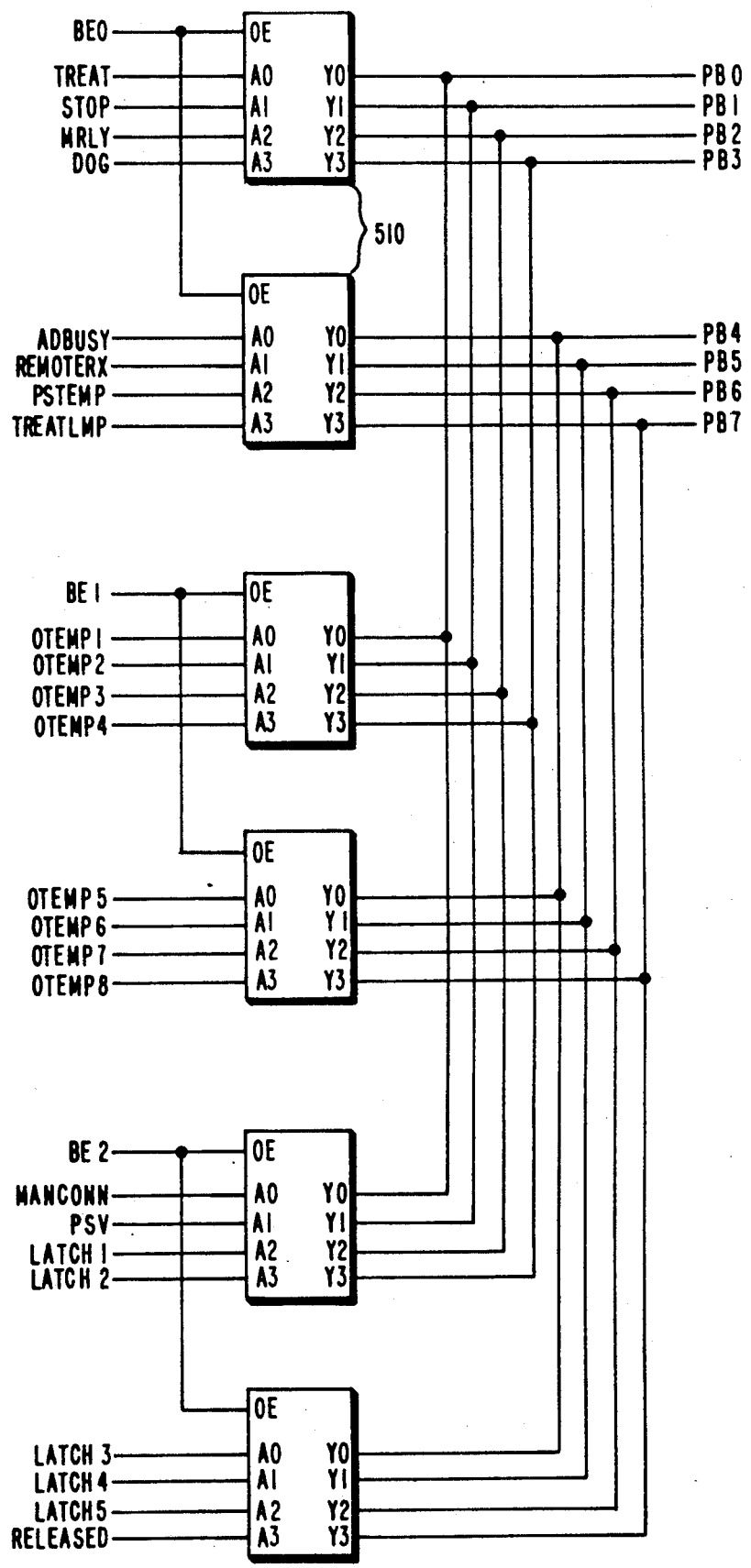
FIG. 25 is an electrical schematic of the status buffer shown in FIG. 21.

Status buffer 462 consists of three 74HC244 octal buffers 510 with three-state outputs connected in parallel as shown in FIG. 25. The status buffer control input (C) shown in FIG. 21A has three buffer-enable lines 0, 1 and 2 (BE0, BE1 AND BE2) connected to respective outputs of control decoder 458 for individual buffer enabling. It will be appreciated that the TREAT signal is the output of treatment control circuit 475, the TREATLMP signal is from treatment lamp circuit 474, the ADBUSY signal is from A/D converter 460, the PSTEMP and PSV signals are the PWRMON signals referred to in FIG. 21A, and the OTEMP signals 1-8 and LATCH signals 1-5 are the OTEMP and LATCH signals, respectively, of FIG. 21A.

Figure 26:
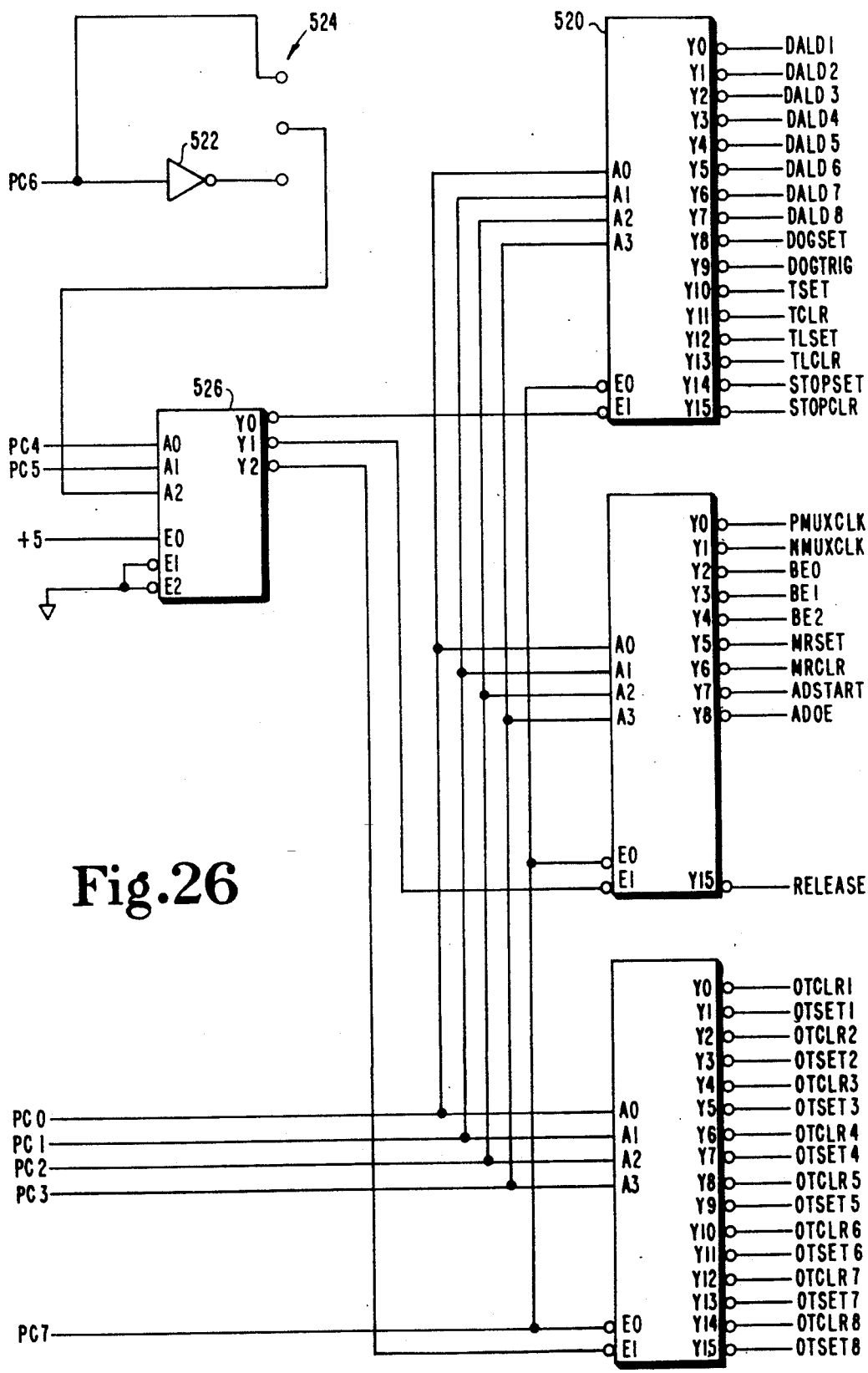
FIG. 26 is an electrical schematic of the control decoder shown in FIG. 21.

With reference to FIG. 26, control decoder 458 includes three 74HC154 4-to-16 decoders 520 with their address inputs connected in parallel to pins 0, 1, 2 and 3 of computer port C (through optoisolator 454). Pin 7 of computer port C is connected to one enable input of each of the decoders, and the other enable input of each decoder is separately controlled from another decoder circuit composed of an inverter 522, an option-select jumper 524, and a 3-to-8 decoder 526, type 74HC138. As shown in FIG. 26, two of the address inputs of 3-8 decoder 526 are connected to pins 4 and 5 of computer port C, and the third address input of the decoder is connected to pin 6 of computer port C, either directly or through inverter 522, depending upon whether the ECS is a master or slave. In this manner the port C outputs intended for control of a master PHS can be distinguished from those intended for control of a slave PHS. FIG. 26 shows the eight individual D/A load signals (DALD 1-8) which are supplied to DAC circuit 456 on control lines 471 of FIG. 21A. The TSET and TCLR output lines of the decoder are coupled to the S and CLR input lines, respectively, of treatment control circuit 475. Similarly, the TLSET and TLCLR lines are coupled to the S and CLR input lines, respectively, of treatment lamp circuit 474, and the STOPSET and STOPCLR output lines are connected to the S and CLR input lines, respectively, of stop lamp circuit 476. As indicated in FIG. 26, there are two MUXCLK output lines from the decoder: PMUXCLK and NMUXCLK. There are also two MRCON lines: master relay set (MRSET) and master relay clear (MRCLR). The A/D start (ADSTART) and A/D output enable (ADOE) signals are the signals supplied on control lines 470 to A/D converter 460. Finally, the OTEMPC output lines from control decoder 458 consist of eight overtemp clear (OTCLR) lines and eight overtemp set (OTSET) lines, paired as indicated in FIG. 26. Each pair of OTCLR and OTSET lines is connected to an individual overtemperature detector in HTR OTEMP circuit 482, as will be described.

Figure 27:
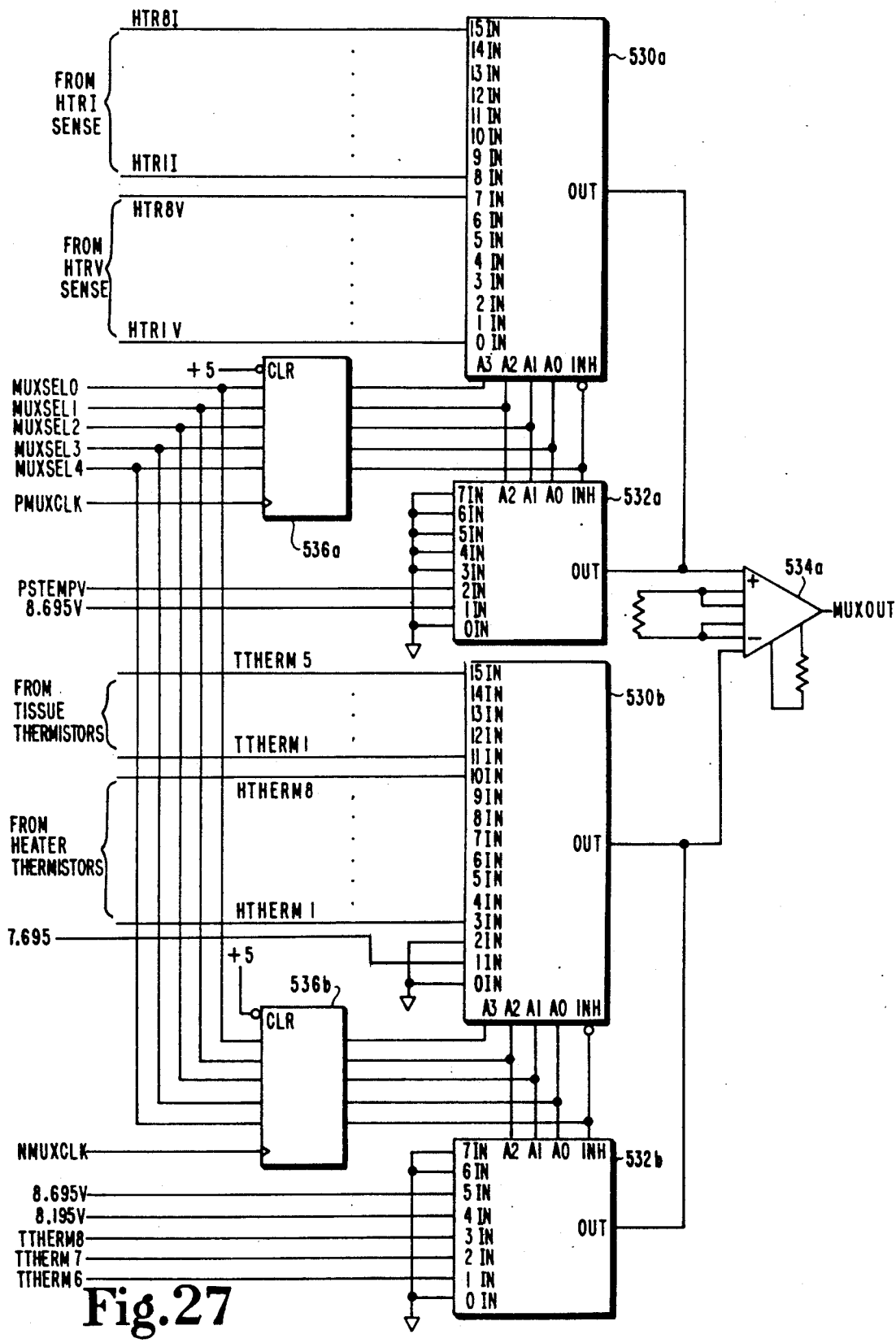
FIG. 27 is an electrical schematic of the multiplexer shown in FIG. 21.

FIG. 27 shows the individual connections for all the analog signal lines which are monitored by the system. The multiplexer includes two sixteen-bit analog multiplexers 530a and 530b, both Datel MV-1606, and two eight-bit analog multiplexers 532a and 532b, both Datel MV-808. Multiplexers 530a and 532a are commonly connected to the positive input of an instrumentation amplifier 534a, Burr-Brown INA101, and are therefore jointly referred to as the P MUX, while multiplexers 530b and 532b, commonly connected to the negative input of the same instrumentation amplifier, are jointly referred to as the N MUX. Data selection is performed by the multiplexers under control of MUX select (MUXSEL) signals 0-4 received from port A of the computer and separately clocked into 74HC273 octal D-type flip-flops 536a and 536b using respective PMUXCLK and NMUXCLK signals, the flip-flops being coupled to the address and inhibit inputs of the analog multiplexers as shown in FIG. 27. With this circuitry a set of MUXSEL signals can be clocked into a selected one of the MUX control latches and a corresponding analog multiplexer input line selected, under computer control. The selected analog signal is supplied on the MUXOUT line to the A/D converter where it is converted to a digital value for input to computer port B through the optoisolator.

Figure 28A:
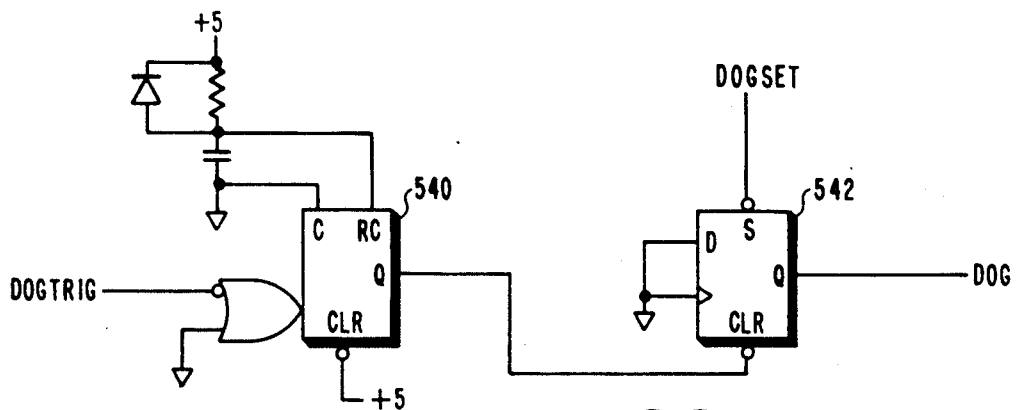
FIGS. 28A-28D are electrical schematics of circuits 473-476 shown in FIG. 21.

The watchdog, treatment lamp, treatment control, and stop lamp circuits depicted as blocks in FIG. 21A are shown in greater detail in FIGS. 28A, 28B, 28C and 28D, respectively. With reference to FIG. 28A, the watchdog timer is composed of a retriggerable one-shot 540, type 74HC4538, the output of which is supplied to the clear input of a 74HC74 D flip-flop 542 having its D and clock inputs tied to digital ground. The inverting, gated trigger input of the one-shot is connected to the DOGTRIG line for control of one-shot operation, the non-inverting, gated trigger input being disabled by connection to digital ground. The Q output of the one-shot is kept in a high state by a periodic retriggering via the DOGTRIG line. The watchdog timer is intended to detect loss of communication from the computer, and to shut down the ECS in the absence of computer control. For this purpose, the one-shot in the watchdog timer is provided with a resistor and capacitor having values appropriate to produce a nominal timing interval of ten seconds, and pulses are supplied on the DOGTRIG line with sufficient frequency to repetitively retrigger the one-shot and thereby prevent it from timing out. In the event of a lapse of trigger pulses sufficient to allow one-shot 540 to time out, the CLR input of D flip-flop 542 and, consequently, the DOG output line go low (logic 0). As will be described, the master control circuit responds to this condition by opening the master relay. The watchdog timer is not automatically reset; instead, a DOGSET signal must be sent from the control decoder, under computer control, to perform this function and thereby enable resumption of operations after a shutdown. The DOGSET line is also used for hardware initialization.

Figure 28B:
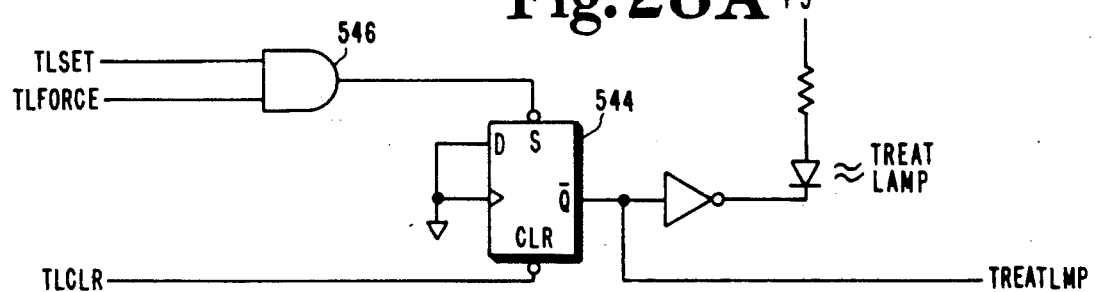

The treatment lamp circuit includes a D-type flip-flop 544 which, through an inverting buffer, drives an LED which serves as the treatment (TREAT) lamp, as shown in FIG. 28B. The treatment lamp is turned on by clearing the flip-flop, and thereby causing the treatment lamp (TREATLMP) output line to go high, with a low pulse on the TLCLR line. The treatment lamp is turned off by setting the flip-flop, which occurs whenever either of the TLSET or TLFORCE inputs to AND gate 546 is low. The TLFORCE line is from master control circuit 472, and is used to force the treatment lamp off in the event of a fault condition resulting in termination of treatment. The TLSET line is provided for computer control of the treatment lamp circuit, specifically, for exercising the circuit and for hardware initialization.

Figure 28C:
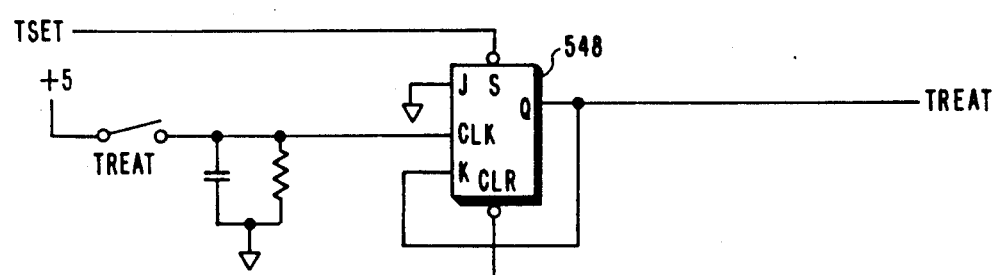

The treatment control circuit, as shown in FIG. 28C, is composed of a JK flip-flop 548 having its clock input connected to the treatment control (TREAT) switch. The state of the JK flip-flop, and consequently the state of operation of the ECS, can be controlled manually with the treatment control switch or under computer control using the TSET and TCLR lines.

Figure 28D:
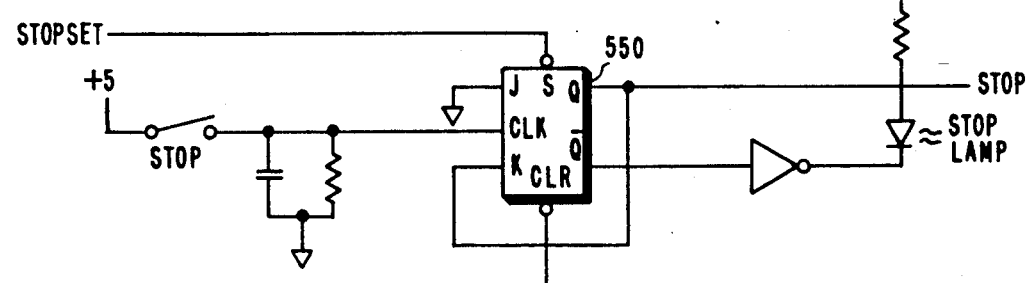

The stop lamp circuit of FIG. 28D has the same type of circuitry as that for the treatment control circuit just described, and additionally has an LED circuit of the type used in the treatment lamp circuit. Flip-flop 550 is controlled by the stop switch manually or, under computer control, by the STOPSET and STOPCLR lines, and the status of the flip-flop is indicated with the stop lamp which is on whenever ECS operations are stopped and which is otherwise off.

Figure 29:
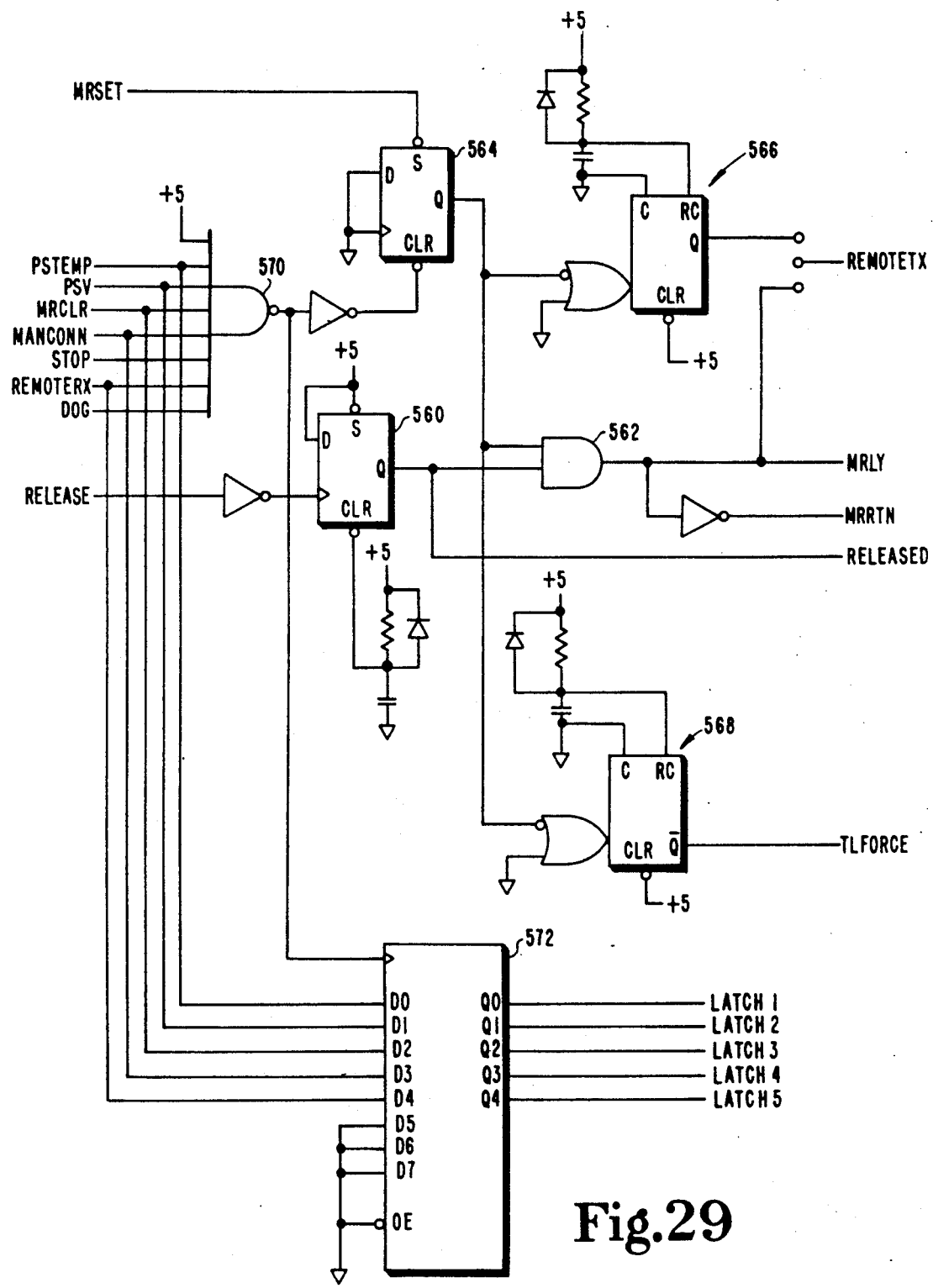
FIG. 29 is an electrical schematic of the master control circuit shown in FIG. 21.

The master control circuit shown in block diagram form in FIG. 21B is shown in greater detail in FIG. 29. The primary function of the master control circuit is to control the master relay. As previously mentioned and as will be more apparent from FIG. 32, the master relay is controlled by the voltage across its coil terminals C, one of which is connected to +5 volts DC, and the other of which is connected to the master relay return (MRRTN) output of the master control circuit. The MRRTN line must be low for the master relay to be energized and thereby supply relay power to all heater and thermistor relay coils and connect VREF to all thermistor common terminals. The master control circuit includes a power-on-reset (POR) latch which insures that the master relay starts out deenergized when system power is turned on, and until a RELEASE signal is sent from the computer. Specifically, D flip-flop 560 is cleared on power-up by an RC POR circuit, whereby its Q output is low disabling AND gate 562 and thereby preventing the MRRTN line from going low. The master relay cannot be energized until the latch is released, which is accomplished under computer control by coupling a low pulse on the RELEASE input to the master control circuit. With the D input of the D flip-flop tied high as shown in FIG. 29, a high-to-low transition of the RELEASE line causes the clock input of the flip-flop to be triggered, whereupon the Q output goes high and enables gate 562. The software-controlled POR latch in the master control circuit eliminates the need for POR circuitry elsewhere in the ECS and thereby simplifies the hardware design. Other logic circuits are initialized as desired under software control after power-up, and then the RELEASE line is pulsed to release the POR latch and thereby enable operation of the master relay. The status of the latch is returned via the RELEASED line and the status buffer to the computer. With gate 562 thus enabled, a low pulse on the MRSET input line sets D flip-flop 564, in response to which the MRRTN line goes low and the master relay closes. Status of the master relay is returned to the computer via the MRLY line coupled to the status buffer.

As will be apparent from FIG. 29 to those skilled in the art, the master relay is disabled whenever any one of the following input signal lines is low: PSTEMP, PSV, MRCLR, MANCONN, STOP, REMOTERX, and DOG. As a result, the master relay opens to fully isolate the patient in response to excessive temperature (PSTEMP) or improper voltage (PSV) in the power supply, a command (MRCLR) from the computer to open, disconnection of the manifold (MANCONN), closing of the stop switch or a stop command from the computer (STOP), a fault condition in the slave PHS (REMOTERX), or loss of computer control as detected by the watchdog timer (DOG).

In a master PHS, the REMOTETX output line is connected to stop-slave pulser 566, whereas, in a remote, or slave, PHS, it is connected to the MRLY line. The stop-slave pulser is a one-shot of the type described above with respect to the watchdog timer, and its function is to generate a pulse to stop the slave PHS whenever master relay latch 564 clears. This routinely occurs when an operator closes the stop switch, which, like the treatment lamp, is provided only for a master PHS. Conversely, the slave PHS can cause the master PHS to shut down in the event of a fault condition causing the master relay in the slave unit to open. In such a case the REMOTETX output of the slave unit, connected to the REMOTERX input of the master unit, goes low and clears flip-flop 564, thereby opening the master unit master relay. Direct master-slave communication ensures fast response to fault conditions, avoiding a delay on the order of several seconds represented by the processing loop cycle time, as will be described later. The master control circuit in the slave unit generates The master control circuit includes a second one-shot 568 the function of which is to generate a low pulse to force the treatment lamp off whenever the master relay latch clears, i.e., whenever the master relay opens, so as to indicate visually that a treatment is not underway. The pulse is coupled via the TLFORCE line from the master control circuit to the treatment lamp circuit. Whenever the master relay latch is cleared, the low-to-high transition of NAND gate 570 causes the states of the PSTEMP, PSV, MRCLR, MANCONN and REMOTERX lines to be latched into a 74HC374 latch 572, for subsequent communication to the computer through the status buffer.

Figure 30:
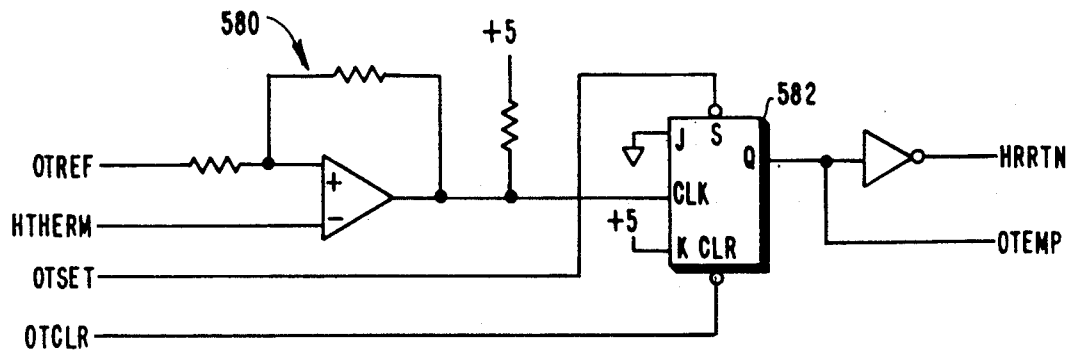
FIG. 30 is an electrical schematic of the heater over-temperature circuit shown in FIG. 21.

The heater overtemp (HTR OTEMP) circuit shown in block diagram form in FIG. 21B includes eight of the circuits shown in FIG. 30, one for each of eight probes whose heater temperature is to be monitored. A given heater thermistor is connected to the inverting input of a comparator 580 provided with hysteresis, as shown, and with a variable reference voltage (OTREF). A given comparator switches to a low output state when its associated heater thermistor (HTHERM) voltage exceeds the predetermined reference voltage. In response, the Q output of a 74HC76 JK flip-flop 582 is clocked low whereby the heater relay return (HRRTN) line is switched high. This disables the associated heater. An indication of this condition is applied to the status buffer via the OTEMP line. The JK flip-flop is also provided with OTSET and OTCLR lines for control thereof by the computer.

Figure 31:
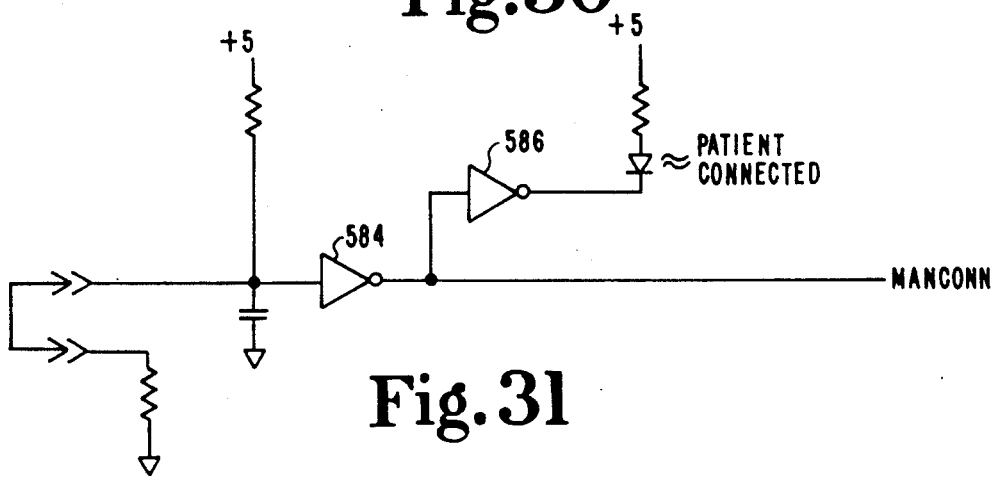
FIG. 31 is an electrical schematic of the manifold sense circuit shown in FIG. 21.

With reference to FIG. 31, the MANIFOLD SENSE circuit includes a cascade-connected pair of inverters 584 and 586 connected to an LED for indication that a patient is connected whenever a circuit between two input terminals is closed. The manifold connector is provided with two corresponding terminals connected by a short circuit for this purpose, and accordingly the PATIENT CONNECTED lamp is on whenever the manifold connector is connected to the ECS. The state of connection of the manifold connector is conveyed to the computer via the MANCONN line.

Figure 32:
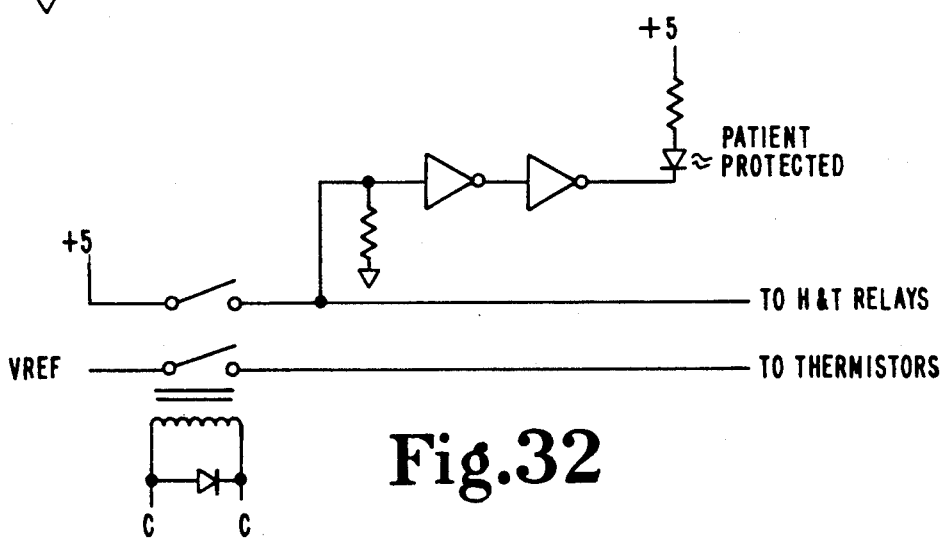
FIG. 32 is an electrical schematic of the master relay circuit shown in FIG. 21.

With reference to FIG. 32, the master relay circuit includes the master relay itself, discussed above, and also includes a buffered LED circuit of the type discussed above with reference to FIG. 31. As will be apparent, the PATIENT PROTECTED lamp is on when the master relay is deenergized. The patient is protected at such times by virtue of complete electrical isolation from the ECS.

With reference to FIG. 33, the power monitor circuit shown in block diagram form in FIG. 21B is shown in further detail. A thermistor circuit 590 is provided to sense the power supply temperature and, through amplifier 592 and comparator 594, generate analog signal PSTEMPV and digital signal PSTEMP corresponding thereto. The offset input to amplifier 592 and the reference (REF) input to comparator 594 are preferably variable. The power supply voltages for the analog (A), digital (D), and relay (R) circuits in the ECS are monitored by a multiple-input comparator 596, Unitrode UC3903, which produces another power monitor status signal, PSV, indicative of power supply voltage. This signal is coupled to the status buffer along with the PSTEMP signal, while the PSTEMPV signal is coupled to MUX 464.

Virtually all the electrical energy delivered to the probe heater coil is converted directly into heat which is conductively transferred to the tumor. It is important to understand the following defined temperatures in relation to the process of heating the tumor with the present invention: internal probe control temperature, surface probe temperature, and minimum tumor tissue carry through temperature. The above-described construction of the probe provides a finely controlled temperature gradient throughout the outer sheath such that the probe surface temperature is determinably lower than the internal probe control temperature. The probe surface temperature, which represents maximum tissue temperature, can be determined from the internal probe temperature, the physical characteristics of the probe and the power applied to the probe:

$$T_s = T_i - PR$$

where
- $T_s$ = probe surface temperature,
- $T_i$ = probe internal temperature,
- P = power applied to probe, and
- R = probe thermal resistance based on probe heater length and characteristics.

Figure 12:
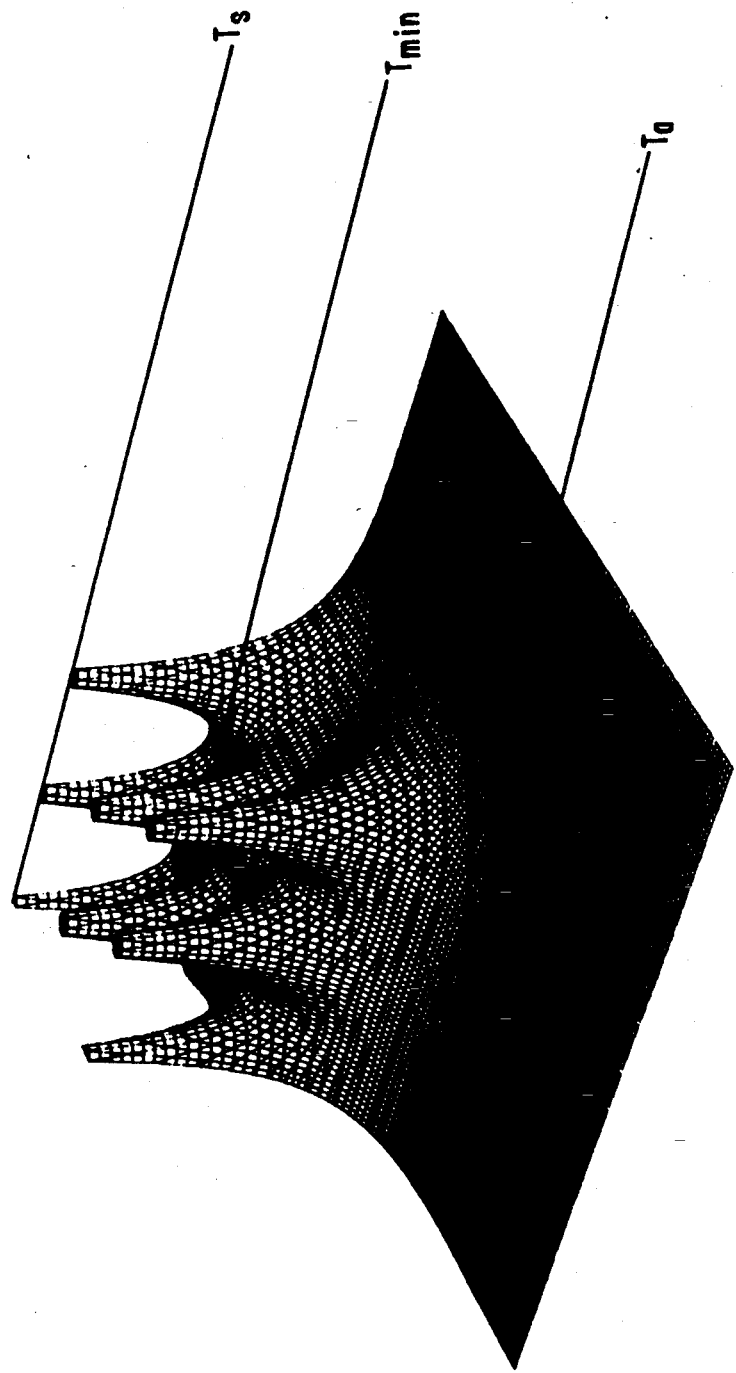
FIG. 12 illustrates temperature distributions in planes perpendicular to probes implanted according to the preferred embodiment of the present invention.

In order to effect precise control of the heating profile, the temperature of the heating coil is maintained at and limited to a prescription temperature via a feedback loop that responds to the temperature of the heater coil as measured by the closely coupled thermistor. To achieve therapeutic heating of tumors deep within a patient's body, a minimum effective temperature must be attained throughout the entire mass for a certain length of time, and this minimum temperature can be effected throughout the tumor mass with the present invention. Perfusion in the neighborhood of each probe can be determined by measuring the power, P, required to maintain each interior probe at the target temperature, $T_i$. The temperature distributions created by the conductive heater arrays in perfused tissues were characterized by computer simulations in order to relate power to blood flow and minimum therapeutic temperature. FIG. 12 illustrates the general features of temperature distributions produced by twenty-three conductive heating elements with the computer simulations. The temperature distributions are characterized by a regular series of peaks and high valleys. The peaks are of uniform height equal to the probe surface temperature ($T_s$). The altitude of the high valley floors is the minimum tissue temperature ($T_{min}$) achieved in the tumor. The floor of the simulation represents the arterial blood temperature ($T_a$). Since the only route for heat loss from the interior high valleys is via blood perfusion and minimally by conduction to adjacent tissues, changes in heater spacing or blood flow affect the minimum valley floor temperature without changing the general shape of the distributions in space. Thus, the conductive heating temperature distribution can be characterized by the target internal heater set point temperature and the minimal therapeutic temperature of the tumor.

Unlike other hyperthermia modalities, the location of maximum tissue temperature is known and precisely controllable in the present invention. In systems such as microwave, RF and ultrasound, heat is generated away from the energy-transmitting source, whereas in the present system the heater coil directly emits the heat and radiates it from the probe surface toward the tumor boundary and surrounding tissue. The temperature gradient decreases from the probe outward, thereby enhancing patient protection.

Figure 34A:
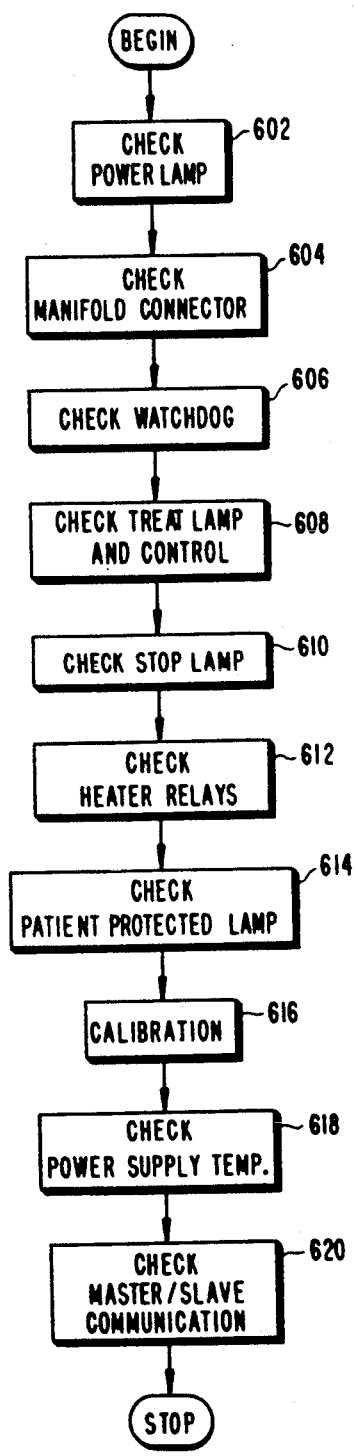
FIGS. 34A and 34B are flowcharts of the exercise and treatment routines executed by the system according to the preferred embodiment of the present invention.

There are four routines in the PHS application software package: hardware exercise (ex), prescription (rx), pre-treatment checkout (chkout), and treatment (tx). Briefly, the ex routine allows the operator to exercise the hardware outside the patient treatment environment; the rx routine is used for establishing a treatment prescription; the chkout routine verifies probe configuration and proper hardware performance prior to treatment; and the tx routine controls the treatment cycle according to the prescription established using the rx routine. The ex and tx routines will be described in a moment with reference to the flow charts of FIGS. 34A and 34B, respectively. First, a description will be provided for the rx routine, which along with the chkout routine, to be described later, is readily understood without the aid of a flowchart. The rx routine enables loading of prescription parameters into the computer for execution during the tx routine. These parameters include treatment temperature, duration, start time, and start date, as well as post-treatment monitor time, number of treatment sessions, time between treatment sessions, treatment probe configuration, identifying information for the treatment and patient, and an alarm high temperature. Values are entered via the computer keyboard in conformity with a menu displayed on the CRT monitor. As one example of a set of suitable time values, positive results have been achieved in brain hyperthermia with repetitive treatment sessions approximately three hours long, with approximately one hour between sessions, for approximately 72 hours. The system is preferably capable of generating treatment temperatures up to approximately 55° C., and the alarm high temperature is preferably set at least 0.5° C. above the prescribed treatment temperature. The rx routine includes two stages of error checking, one occurring automatically in response to keyboard entries, and the other occurring after the operator has completed definition of a new prescription and indicated the same to the computer via a function key on the keyboard. The first error check detects invalid keyboard entries related to improper data format or length. The computer beeps to inform the operator of any error detected during this threshold validation stage. A final set of error checks is performed after the new prescription is defined. This final validation stage involves various logical checks, such as a check that the specified treatment temperature is less than the alarm high temperature by a specified amount, that the time between treatment sessions is greater than the sum of the treatment time and the post-treatment monitor time, and that the specified probe configuration matches a known configuration. Any errors detected during this stage are displayed for correction by the operator, and correction is required before the operator is permitted to exit the rx routine.

The ex and tx routines are alternatively operable in an interactive, or prompted, mode and in a stand-alone mode, with the prompted mode as the default mode of operation. For the ex routine running in prompted mode, the first step after the routine begins is step 602, in which a question is displayed on the monitor to prompt the system operator to check the power lamp, which should be on at this time if the power supply voltages are within tolerance. The computer waits for entry of an answer via the computer keyboard, the answer is recorded, and the program proceeds to step 604 for a check of the manifold connector. At this point the operator is prompted to check the PATIENT CONNECTED lamp, and the operator's keyboard response is recorded. Steps 602 and 604 are not performed in stand-alone mode. In step 606, performed in prompted and stand-alone modes, a control signal is sent to the control decoder to trigger the watchdog timer, in response to which the DOG line should change states. Contemporaneously a control signal is sent through the control decoder to enable the buffer in status buffer 462 which has the DOG line as an input, and then the DOG line is read by the computer, which then records whether or not the watchdog timer is active as expected immediately after triggering. The timer is nominally set to time out after ten seconds, and this operation is automatically checked by the computer by monitoring the DOG line at seven and thirteen seconds after triggering and recording the results.

The next step, 608, is a check of the treatment lamp and treatment control circuits, with control signals sent through the control decoder to the status buffer as appropriate to enable monitoring of the desired signals. In both prompted and stand-alone modes the output of treatment control circuit 475, the TREAT line, is monitored to ensure that treatment flip-flop 548 is initially set, and then the flip-flop is cleared by the computer and checked again. In prompted mode the flip-flop is then set by the computer and checked once more. The operator is then prompted to close the treatment (TREAT) switch and indicate to the computer via the keyboard that the action has been taken. The computer responds by making another check of the treatment flip-flop and recording whether or not it is clear as expected. The treatment (TREAT) lamp should not be lit at this time, and the status of the TREATLMP line is monitored at this time to confirm that this is the case. As additional confirmation, the operator is prompted to visually check the treatment lamp, and the indicated result of the visual check is also recorded. Next a TLCLR signal is sent to flip-flop 544 in the treatment lamp circuit, and then the TREATLMP line is checked as an indication that the treatment lamp is on. As additional confirmation the operator is prompted to visually check the treatment lamp and confirm via the keyboard that the lamp is lit. The result is recorded, the treatment flip-flop is set to return it to its initial high state, and flip-flop 544 is set via the TLSET line to return the treatment lamp to its original off state, and the TREAT and TREATLMP lines are monitored as confirmation. In stand-alone mode, after checking the treatment flip-flop initially and then clearing it and checking it again, the treatment lamp is turned on and off by the computer, with the TREATLMP line being monitored before and after flip-flop 544 is cleared to turn the lamp on and after the flip-flop is set to turn the lamp off. The treatment flip-flop is then set to return it to its initial high state.

In step 610, the stop lamp circuit is checked in a manner similar to that described above with respect to the treatment lamp. In both modes the STOP line is monitored to ensure that stop flip-flop 550 is initially set, and then the flip-flop is cleared and set again, with the STOP line being monitored at each step. The stop lamp check is complete at this point for stand-alone mode, but in prompted mode the program goes on to prompt the operator to visually check the stop lamp, and the indicated result of the visual check is recorded. The operator is then prompted to close the stop switch, and this action is checked by monitoring the STOP line once again and also prompting the operator to confirm via the keyboard that the lamp is lit. Flip-flop 550 is then set to return it to its initial high state and to return the stop lamp to its initial off state.

The heater relays are exercised next, in step 612. Each heater relay is closed and opened and its status checked to confirm proper operation. Since the ECS is not necessarily connected to a probe at this time, the OTEMP lines are used as an indication of heater relay status. Each flip-flop 582 is sequentially set and reset, via the OTSET and OTCLR lines, and the results recorded.

In step 614, which is only performed in prompted mode, the PATIENT PROTECTED lamp is checked while the master relay is open, at which time the lamp should be on to indicate complete electrical isolation of the ECS circuitry from connector 313 (FIG. 8).

The calibration step (616) involves tests of the A/D and D/A converters and the reference voltages supplied to MUX 464. First, the MUX is set to sequentially output full-scale, mid-scale and zero-scale values based on the reference voltages supplied by VREF circuit 488. The computer determines and records whether the values are within an acceptable range. After this the DACs are checked by sequentially loading each one with a high value with all other DACs set to 0 and then, through HTRV sense circuit 484, MUX 464 and A/D converter 460, reading the resulting heater command voltages and determining whether they are in an acceptable range. In the final step of the sequence the voltages are read with all DACs set to 0. In the prompted mode, this step also involves a series of prompts for the operator to check for appropriate bar graph response at each step in the sequence.

Power supply temperature is checked in step 618. In this step MUX 464 is set to couple the PSTEMPV signal from power monitor 490 to the A/D converter for reading by the computer, which records whether or not the temperature reading is within an acceptable range.

A check of the master relay and a cursory check of master/slave communication are performed in step 620, the final step before the ex routine stops. In this step the MRLY signal is monitored by the computer as an indication of the status of the master relay. A control signal is sent through control decoder 458 to status buffer 462 to enable the appropriate buffer for reading the MRLY line. The MRLY line is read once initially as an indication that the master relay is open, then a MRSET pulse is sent to master control circuit 472 to set the master relay. If the manifold is not connected at this time, the MANCONN line and, consequently, the CLR input of flip-flop 564 (FIG. 29), are low, so the Q output of the flip-flop should be low following termination of the MRSET pulse. The MRLY line is checked at that point and its status is recorded. The MRLY line should not change state in response to the MRSET command if the manifold is not connected, and should change state if the manifold is connected. Next, a MRCLR signal is sent to master control circuit 472 as a command for the master relay to open, and the MRLY line is again checked to confirm that the relay is open as expected.

Opening of the master relay in a slave PHS can be detected by monitoring the REMOTERX line connected to the status buffer. It should be understood that each step of the ex routine as described above involves a check of all PHS units in the system, and that similar provisions are made for the other routines in the software package.

The chkout routine is an optional program provided for checking various system parameters prior to running the tx routine. This routine verifies the probe configuration as defined in the rx routine, checking each possible probe position and comparing the results of the check with the value required for that position by the rx routine. Inconsistencies are displayed along with suggested troubleshooting steps. Pertinent parameters of each probe, including heater and thermistor characteristics, are displayed, and in addition the computer indicates via the display whether all values match, a problem exists, or a reminder is in order. This last indication is useful where, for example, an unused part is detected. Function keys are provided for such functions as error and other status messages, a troubleshooting guide, retesting of individual heater and thermistor readings, and generating plots of readings. The chkout routine is intended to be run with a patient connected to the system.

Figure 34B:
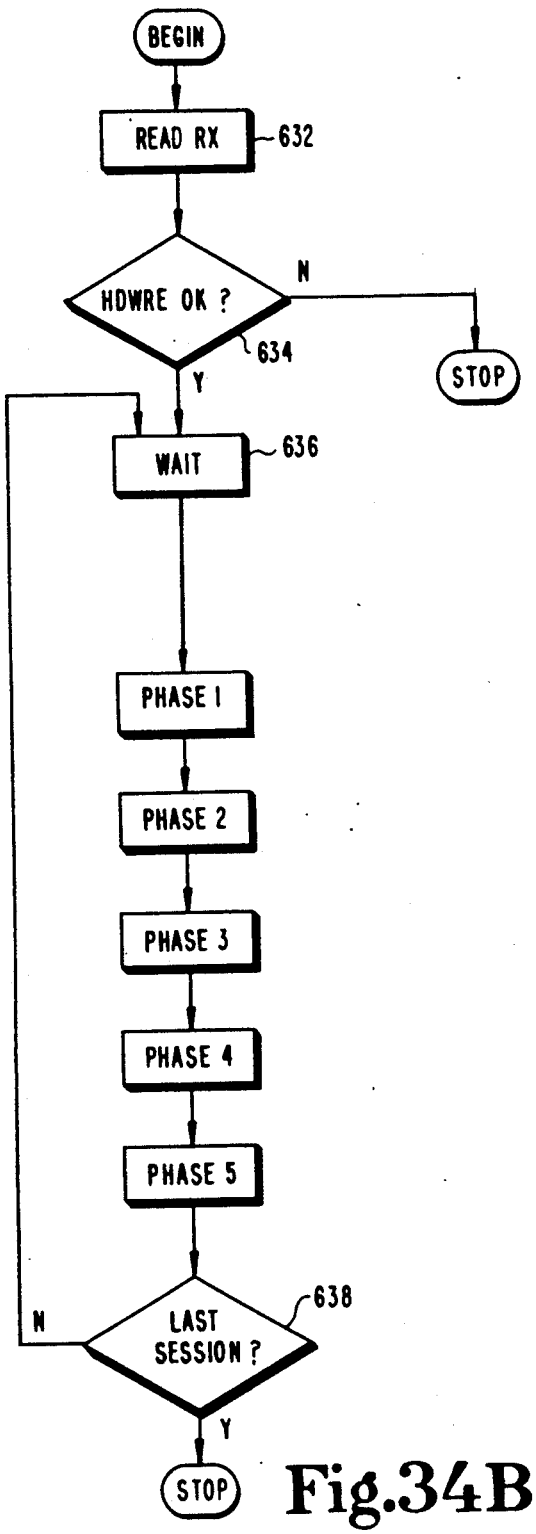

With reference to FIG. 34B, the tx routine will now be described. The first step after the program begins is step 632, in which a particular prescription specified by the operator is read from memory. If no prescription is specified by the operator, the program remains in an internal loop in 632 wherein the operator is prompted to enter identifying information. Next, in step 634, the computer performs a check of the hardware. Like the chkout routine described above, this check involves a comparison of actual probe types and positions with those specified in the pertinent prescription. Some measure of redundancy is thereby provided, although fewer error messages are provided and less operator interaction occurs. The program stops if any errors are detected, and otherwise proceeds to step 636 where it waits until the start time of the first treatment session. When that time comes, the computer initializes the hardware, printer and CRT screen for a new session, and then asks the operator to close the treatment switch to signal confirmation of the desire to begin the session. The hardware initialization includes closing the master relay whereby the patient is no longer electrically isolated from PHS hardware. The system then begins phase 1, in which the heater probes are heated to the target temperature defined in the prescription. In phase 2, the probes are maintained at the target temperature for the specified treatment time. The computer is programmed to provide proportional-integral-differential (PID) temperature control in both phases 1 and 2, with critically damped response during phase 1, for minimum rise time without overshoot, and overdamped response during phase 2 for greater stability. Temperature samples are taken from each heater probe each time through the processing loop, which has a nominal cycle time on the order of two to three seconds in a system with 1 slave PHS, and a new heater command voltage is calculated for each heater probe according to its individual temperature sample and the above-described loop control characteristics.

It should be noted here that different probes may reach the target temperature at different times and therefore may enter and leave phase 2 at different times. The system provides for maintaining each probe in phase 2 for the specified treatment time. An exception to this occurs in the case of a probe which, for example, is positioned in an environment of high heat loss, such as in the vicinity of an artery, where the probe is unable to reach the target temperature even with its DAC at full scale. Modified phase 2 operation is available upon operator election for such a probe. First, the DAC for the affected probe is set back to 0 if the probe fails to reach a predetermined temperature within a predetermined time interval, preferably three processing loop cycles. The operator is then prompted to elect modified phase 2 operation if desired. To minimize the risks of improper operation, the keyboard is not used for operator feedback at this time. Instead, the operator is prompted to close the treatment switch to make the election, and the TREAT line is accordingly monitored for approximately five seconds thereafter to receive the operator's response. If the operator closes the switch in the permitted time, phase 2 is modified for the affected probe as follows: The DAC is set to full scale, i.e., full power to the probe, and the time remaining in phase 2 for the affected probe is set equal to that of the last probe to enter phase 2 prior to the affected probe. Modified phase 2 operation is available for a limited number of heater probes; unless a predetermined number of probes, preferably at least half the total, perform satisfactorily, the system shuts down.

In phase 3, which different probes may enter at different times as explained above, the DACs are reset to 0 whereupon the probes immediately start to cool down. In phase 4, probe temperatures are monitored, with power to the probes still at 0, for the post-treatment monitor time interval defined by the prescription. Provision is also made for a false error condition causing the master relay to open improperly in phase 4. In such a case the computer sends one command pulse to master control circuit 472 to close the master relay. If the relay recloses, temperature is monitored for approximately one more minute and then the entire system proceeds to phase 5. If the relay does not close upon command, the tx routine stops. In phase 5 the system waits for all probes to leave phase 4, after which the program proceeds to decision step 638, from which it branches back to step 636 if another treatment session is specified. If no further treatment sessions are to be run, program execution stops after displaying a message indicating that the treatment session is complete.

As will be appreciated from the foregoing, the above phases of each treatment session involve repetitive processing of information from the various implanted probes. As part of the processing loop, the computer monitors and records all voltage and current readings and temperature readings as well as all hardware status bits. Unexpected occurrences are recorded in an error log, and, in response to certain conditions, such as a time-out of the watchdog timer or detection of closing of the stop switch, the computer terminates the treatment session and sounds an alarm. The elapsed time is recorded, and provision is made for re-entering the tx routine later if the operator desires to complete the treatment session after all fault conditions are eliminated. Individual heaters are disabled via their respective heater relays if they experience an overtemperature condition, but the treatment session continues unless a predetermined number of heater probes are disabled.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for producing volumetric, thermally conductive hyperthermia for the treatment of a tissue mass in a patient, comprising:
   an implantable, heat-emitting source responsive to power applied thereto for producing thermally conductive heat in a predetermined thermally conducted temperature distribution in said tissue mass when implanted in said tissue mass;
   temperature sensor means for measuring temperature thereabout when implanted in said tissue mass; and temperature sensor means for measuring temperature thereabout when implanted in said tissue mass; and control means responsive to the temperature measured about said sensor means and the power applied to said heat-emitting source for controlling the power applied to said heat-emitting source.

2. A system for producing volumetric, thermally conductive hyperthermia for the treatment of a tissue mass in a patient, comprising:

implantable, heat-emitting means responsive to power applied thereto for producing thermally conductive heat in a predetermined thermally conducted temperature distribution in said tissue mass when implanted in said tissue mass in a predetermined pattern;

temperature sensor means for measuring temperature thereabout when implanted in said tissue mass; and control means responsive to the temperature measured about said sensor means and the power applied to said heat-emitting means for controlling the power applied to said heat-emitting means.

3. The system of claim 2 further comprising means for implanting said heat-emitting means in said tissue mass in said predetermined pattern.

4. The system of claim 2 wherein said heat-emitting means includes a plurality of probes each including a heater element.

5. The system of claim 4 wherein each of said plurality of probes further includes a tapered tip for implanting the probe in said tissue mass.

6. The system of claim 4 wherein each of said probes includes a temperature sensor of said sensor means for measuring an internal temperature of the probe.

7. The system of claim 6 wherein said control means is responsive to the internal temperature of each of said probes for controlling the power applied to said heater elements.

8. The system of claim 7 wherein each of said probes includes an outer surface and wherein said control means is responsive to the internal temperature of each of said probes for controlling the power applied to each of said heater elements to produce at least a predetermined temperature along the outer surface of the probe contributing to said predetermined thermally conducted temperature distribution in said tissue mass.

9. The system of claim 8 wherein each of said heater elements includes a resistive heating wire wound in a cylindrical tubular form, the power applied to each of the resistive heating wires being controlled by said control means to produce said at least a predetermined temperature along the outer surface of the probe.

10. A system for producing volumetric, thermally conductive hyperthermia for the treatment of a tissue mass in a patient, comprising:

a plurality of implantable probes each including a heater element, each of said heater elements being responsive to power applied thereto for producing thermally conductive heat in an individual, predetermined, thermally conducted temperature distribution in said tissue mass;

said plurality of implantable probes also including a plurality of temperature sensors each for measuring temperature thereabout; and control means responsive to the temperature measured about each of said temperature sensors and the power applied to each of said heater elements when said plurality of probes are implanted in said tissue mass in a determinable pattern for controlling the power applied to each of said heater elements to produce a combinational, predetermined, thermally conducted temperature distribution in said tissue mass resulting from the individual temperature distributions.

11. The system of claim 9 further comprising template means for guiding said probes into said tissue mass.

12. The system of claim 9 wherein each of said heater elements includes a resistive heating wire wound in a cylindrical tubular form, the power applied to each of the resistive heating wires being controlled by said control means to produce at least a predetermined temperature along an outer surface of the probe.

13. A system for producing volumetric, thermally conductive hyperthermia for the treatment of a tissue mass in a patient, comprising:

a plurality of implantable probes each having an outer surface and including a heater element therein for producing thermally conductive heat;

each of said probes also including a temperature sensor for determining an outer surface temperature of the probe; and control means responsive to the outer surface temperature determined by each of said sensors and a thermal conduction property of said tissue mass for controlling the power applied to said heater elements to produce a predetermined minimum temperature throughout said tissue mass.

14. The system of claim 13 wherein said control means is responsive to thermal conductivity of said tissue mass for controlling the power applied to said heater elements.

15. The system of claim 13 wherein said control means is responsive to perfusion of said tissue mass for controlling the power applied to said heater elements.

16. The system of claim 13 wherein said control means is responsive to a minimum tissue carry through temperature of said tissue mass for controlling the power applied to said heater elements.

17. The system of claim 13 wherein said control means is responsive to thermal conductivity and perfusion of said tissue mass for controlling the power applied to said heater elements.

18. The system of claim 13 wherein each of said heater elements includes a cylindrical shape, the power applied to each of the heater elements being controlled by said control means to produce at least a predetermined temperature along the outer surface of the probe.

19. A system for producing volumetric, thermally conductive hyperthermia for the treatment of a tissue mass in a patient, comprising:

heat-emitting probe means shaped for interstitial implantation in said tissue mass and responsive to power applied thereto for radiating thermally conducted heat therefrom at a predetermined surface temperature;

temperature sensor means for determining surface temperature of said probe means when implanted in said tissue mass; and control means responsive to the surface temperature determined by said temperature sensor means for controlling the power applied to said heat-emitting probe means when interstitially implanted in said tissue mass in a predetermined pattern for producing a predetermined thermally conducted temperature distribution in said tissue mass.

20. The system of claim 19 further comprising template means for guiding said probe means into said tissue mass.

21. The system of claim 19 wherein each of said heat-emitting probe means includes a resistive heating wire wound in a cylindrical tubular form, the power applied to each of the resistive heating wires being controlled by said control means to produce at least a predetermined temperature along an outer surface of the probe means.

22. A system for producing volumetric, thermally conductive hyperthermia for the treatment of a tissue mass having a temperature distribution in a patient, comprising:
   interstitially implantable, heat-emitting probe means responsive to power applied thereto for producing thermally conductive heat to change said temperature distribution of said tissue mass;
   temperature sensor means for measuring temperature thereabout when implanted in said tissue mass; and
   control means responsive to the temperature measured about said sensor means and the power applied to said probe means for controlling the power applied to said interstitially implantable, heat-emitting probe means for producing thermally conductive heat to change said temperature distribution of said tissue mass.

23. The system of claim 22 wherein each of said heat-emitting probe means includes a resistive heating wire wound in a cylindrical tubular form, the power applied to each of the resistive heating wires being controlled by said control means to produce at least a predetermined temperature along an outer surface of the probe means.

24. A system for producing volumetric, thermally conductive hyperthermia for the treatment of a tissue mass in a patient, comprising:
   implantable, heat-emitting probe means responsive to energy applied thereto for producing thermally conductive heat in a predetermined thermally conducted temperature distribution in said tissue mass when interstitially implanted in said tissue mass in a predetermined pattern;
   temperature sensor means for measuring temperature thereabout when implanted in said tissue mass; and
   control means responsive to the temperature measured about said sensor means and the energy applied to said probe means for controlling the energy applied to said implantable, heat-emitting probe means to produce said predetermined thermally conducted temperature distribution in said tissue mass.

25. A system for producing volumetric, thermally conductive hyperthermia for the treatment of a tissue mass in a patient, comprising:
   a plurality of interstitially implantable probes each including a heat-emitting element, each of said heat-emitting elements being responsive to energy applied thereto for producing thermally conductive heat in an individual, predetermined, thermally conducted temperature distribution in said tissue mass;
   said plurality of interstitially implantable probes also including a plurality of temperature sensors each for measuring temperature thereabout;
   control means responsive to the temperature measured about each of said temperature sensors and the energy applied to each of said heat-emitting elements when said plurality of probes are interstitially implanted in said tissue mass in a determinable pattern for controlling the energy applied to each of said heat-emitting elements to produce a combinational, predetermined, thermally conducted temperature distribution in said tissue mass resulting from the individual temperature distributions.

26. A system for producing volumetric, thermally conductive hyperthermia for the treatment of a tissue mass in a patient, comprising:
   a plurality of interstitially implantable probes each having an outer surface and including a heat-emitting element therein for producing thermally conductive heat;
   each of said probes also including a temperature sensor for determining an outer surface temperature of the probe; and
   control means responsive to the outer surface temperature determined by each of said sensors and a thermally conducted temperature distribution of said tissue mass for controlling the energy applied to said heat-emitting elements to produce a predetermined minimum temperature throughout said tissue mass.

27. A system for producing volumetric, thermally conductive hyperthermia for the treatment of a tissue mass in a patient, comprising:
   heat-emitting probe means shaped for interstitial implantation in said tissue mass and responsive to energy applied thereto for radiating thermally conducted heat therefrom at a predetermined surface temperature;
   temperature sensor means for determining surface temperature of said probe means when implanted in said tissue mass; and
   control means responsive to the surface temperature determined by said temperature sensor means for controlling the energy applied to said heat-emitting probe means when interstitially implanted in said tissue mass in a predetermined pattern for producing a predetermined thermally conducted temperature distribution in said tissue mass.

28. A system for producing volumetric, thermally conductive hyperthermia for the treatment of a tissue mass having a temperature distribution in a patient, comprising:
   interstitially implantable, heat-emitting probe means responsive to energy applied thereto for producing thermally conductive heat to change said temperature distribution of said tissue mass;
   temperature sensor means for measuring temperature thereabout when implanted in said tissue mass; and
   control means responsive to the temperature measured about said sensor means and the energy applied to said probe means for controlling the energy applied to said interstitially implantable, heat-emitting probe means for producing thermally conductive heat to change said temperature distribution of said tissue mass.

29. A system for producing volumetric hyperthermia for the treatment of a tissue mass in a patient, comprising:
   a plurality of interstitially implantable probes responsive to power applied thereto for producing thermally conductive heat in said tissue mass;
   sensor means for determining the thermal conductivity of said tissue mass; and
   control means responsive to the power applied to said probes and the thermal conductivity of said tissue mass for controlling the power applied to said probes to produce a predetermined minimum temperature throughout said tissue mass.

* * * * *